(12) United States Patent
Miura et al.

(10) Patent No.: US 7,429,622 B2
(45) Date of Patent: Sep. 30, 2008

(54) ACTIVE RAY CURABLE INK-JET COMPOSITION, IMAGE FORMING METHOD USING THE SAME, INK-JET RECORDING APPARATUS, AND TRIARYLSULFONIUM SALT COMPOUND

(75) Inventors: Norio Miura, Sagamihara (JP); Masato Nishizeki, Hachioji (JP); Kimihiko Okubo, Hino (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 0 days.

(21) Appl. No.: 11/591,703

(22) Filed: Nov. 2, 2006

(65) Prior Publication Data

US 2007/0054974 A1 Mar. 8, 2007

Related U.S. Application Data

(62) Division of application No. 10/826,059, filed on Apr. 15, 2004, now Pat. No. 7,244,473.

(30) Foreign Application Priority Data

| Apr. 22, 2003 | (JP) | ............................. 2003-116933 |
| Jul. 14, 2003 | (JP) | ............................. 2003-196367 |
| Oct. 15, 2003 | (JP) | ............................. 2003-354742 |

(51) Int. Cl.
*C08F 2/50* (2006.01)
*C08F 2/46* (2006.01)

(52) U.S. Cl. .......................... 522/31; 522/168; 522/170
(58) Field of Classification Search .................. 522/31, 522/170, 181; 106/31.13
See application file for complete search history.

(56) References Cited

U.S. PATENT DOCUMENTS

| 6,306,555 | B1 | 10/2001 | Schulz et al. |
| 6,913,352 | B2 | 7/2005 | Yoshihiro et al. |
| 2004/0052968 | A1 | 3/2004 | Takabayashi |
| 2005/0064333 | A1 | 3/2005 | Crivello |
| 2006/0055088 | A1 | 3/2006 | Nakayashiki et al. |

FOREIGN PATENT DOCUMENTS

| JP | 60-119554 B2 | 6/1985 |
| JP | 06-200204 A | 7/1994 |
| JP | 2000-504778 A | 4/2000 |
| JP | 2001-220526 A | 8/2001 |
| JP | 2002-188025 A | 7/2002 |
| JP | 2000-241474 A | 8/2002 |
| JP | 2002-317139 A | 10/2002 |
| JP | 2004-91698 A | 3/2004 |

*Primary Examiner*—Sanza L McClendon
(74) *Attorney, Agent, or Firm*—Frishauf, Holtz, Goodman & Chick, P.C.

(57) ABSTRACT

An active ray curable ink-jet ink composition comprising a photo-induced acid generating agent containing an onium salt which does not generate benzene under active ray radiation, and a photopolymerizable compound containing a compound having an oxetane ring in the molecule.

9 Claims, 2 Drawing Sheets

ACTIVE RAY CURABLE INK-JET COMPOSITION, IMAGE FORMING METHOD USING THE SAME, INK-JET RECORDING APPARATUS, AND TRIARYLSULFONIUM SALT COMPOUND

This application is a divisional of application Ser. No. 10/826,059, filed Apr. 15, 2004, now U.S. Pat. No. 7,244,473 which is hereby incorporated in its entirety herein by this reference.

FIELD OF THE INVENTION

The present invention relates to a triarylsulfonium salt compound, an active ray curable ink-jet ink composition containing that compound, an active energy ray curable composition, and an image forming method and an ink-jet recording apparatus both using the same, which are stably capable of reproducing a high-definition image onto every kind of recording material under the various printing conditions without release of benzene, which is toxic to the human body.

BACKGROUND OF THE INVENTION

In recent years, ink-jet recording systems have been applied to various printing fields such as photography, various forms of printing, marking, and special printing such as color filters due to its capability of forming images simply and inexpensively. Specifically, it has become possible to achieve image quality comparable to that of silver salt photography, by employing recording apparatuses which eject minute dots under control, inks which exhibit an enhanced color reproduction range as well as enhanced durability, and improved ejection adaptability, and exclusive sheets which exhibit markedly improved ink absorbability, color forming properties of color materials and surface glossiness. Enhancement of image quality of the current ink-jet recording system is achievable only by simultaneous improvement of all the recording apparatuses, inks and exclusive sheets.

However, ink-jet systems, which require special recording sheets, result in problems such as limitations of recording media as well as a higher cost of the foregoing recording media. As a result, a number of experiments have been conducted in which recording is carried out on image receiving media differing from such exclusive sheets, while employing various ink-jet systems. Specific examples include a phase change ink-jet system using a wax based ink which is solid at room temperature, a solvent based ink-jet system using an ink comprised of rapid drying organic solvents as a main component, and a UV ink-jet system in which after image recording, crosslinking is carried out employing ultraviolet (UV) radiation.

Of these, in recent years, the UV ink-jet system has received much attention due to its relatively low generation of unpleasant odors, rapid drying properties, and recording capability onto recording media exhibiting no ink absorbability. Ultraviolet radiation curing ink-jet inks are disclosed, for example, in Japanese Patent Publication No. 5-054667, Unexamined Japanese Patent Application Publication No. 6-200204, and Unexamined Japanese Patent Application Publication (under PCT Application) No. 2000-504778.

However, even though these inks are employed, it is very difficult to form high-definition images on each of the recording materials due to large differences of ink dot diameter after the ink deposition, depending on the type of recording materials and operation environment.

Specifically, UV radiation curable inks using a cationic polymerizable compound have been proposed (for, example, Patent Documents 1-3), however, these UV radiation curable inks have drawbacks which tend to be affected by molecular level moisture and oxygen inhibition action, and release of benzene, being toxic to the human body. In other words, in many cases, an active ray curable ink-jet ink composition using cationic polymerizable compounds described in foregoing Patent Documents 1-3 contains UVR6110 and UVR6105 produced by Dow Chemical Company, or CEL-LOXIDE 2021 produced by DAI CEL CHEMICAL INDUSTRIES, LTD. as a photopolymerizable compound, and thus, these compounds have drawbacks such as releasing harmful benzene, large fluctuation of ejection stability and curability under varying printing conditions (such as temperature and humidity), and wrinkling due to shrinkage while curing.

Patent Document 1: Unexamined Japanese Patent Application Publication (hereinafter, referred to as JP-A) No. 2001-220526
Patent Document 2: JP-A 2002-188025
Patent Document 3: JP-A 2002-317139

SUMMARY OF THE INVENTION

From the viewpoint of the foregoing drawbacks, the present invention is offered. An object of the present invention is to provide a triarylsulfonium salt compound, an active ray curable ink-jet ink composition containing that compound, an active energy ray curable composition, and an image forming method and an ink-jet recording apparatus both using the same, which are stably capable of reproducing a high-definition image without color contamination onto most recording materials under various printing conditions, without releasing of benzene, being toxic to the human body.

The foregoing object of the present invention was achieved employing the embodiments described below.

Item 1. An active ray-curable ink-jet ink composition comprising:
an onium salt as a photo-induced acid generating agent, which does not generate benzene during active ray radiation, and
a photopolymerizable compound, which contains an oxetane ring.

Item 2. The active ray-curable ink-jet ink composition of Item 1 above, wherein the foregoing onium salt which does not generate benzene is a sulfonium salt.

Item 3. The active ray-curable ink-jet ink composition of Item 1 above, wherein the foregoing onium salt which does not generate benzene is an iodonium salt.

Item 4. An active ray-curable ink-jet ink composition containing an onium salt as a photo-induced acid generating agent, which does not generate benzene, wherein the onium salt is a sulfonium salt selected from following Formulas (1)-(4):

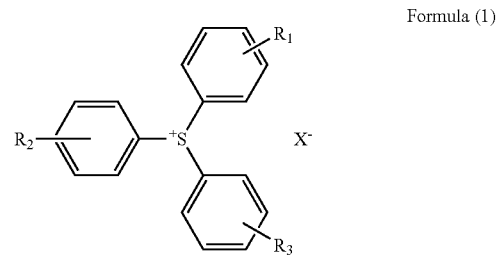

Formula (1)

Formula (2)

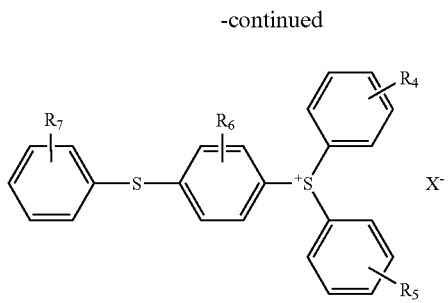

Formula (3)

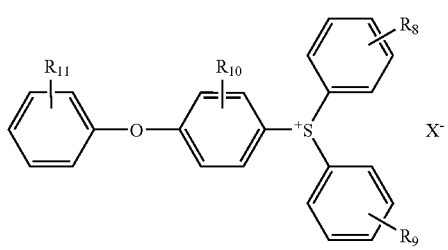

Formula (4)

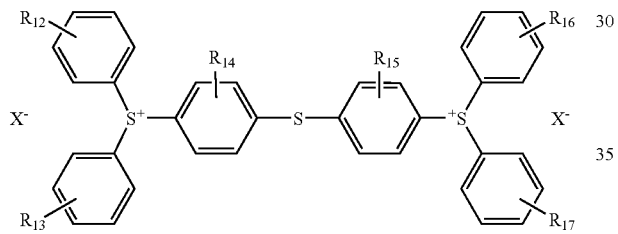

wherein $R_1$-$R_{17}$ are each a hydrogen atom or a substituted group, $R_1$-$R_3$ are not a hydrogen atom at the same time, $R_4$-$R_7$ are not a hydrogen atom at the same time, $R_8$-$R_{11}$ are not a hydrogen atom at the same time, and $R_{12}$-$R_{17}$ are not a hydrogen atom at the same time; while X is a non-nucleophillic anion residue; however, $R_1$-$R_3$ of Formula (1) are not a phenylthio group or a phenoxy group.

Item 5. The active ray-curable ink-jet ink composition of Item 4 above, wherein the sulfonium salt represented by foregoing Formulas (1)-(4) is at least a compound selected from sulfonium salts represented by following Formulas (5)-(13):

Formula (5)

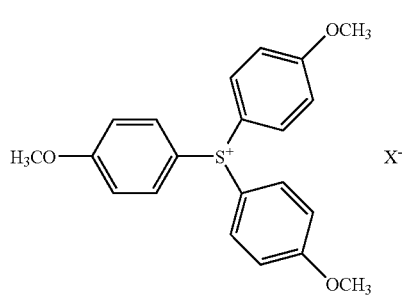

Formula (6)

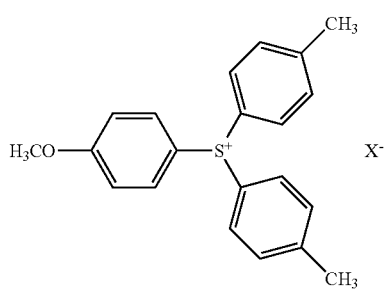

Formula (7)

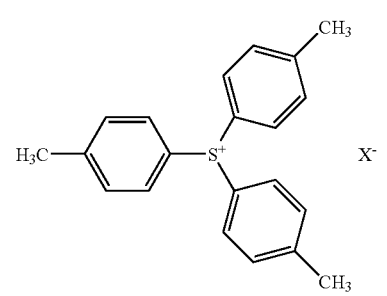

Formula (8)

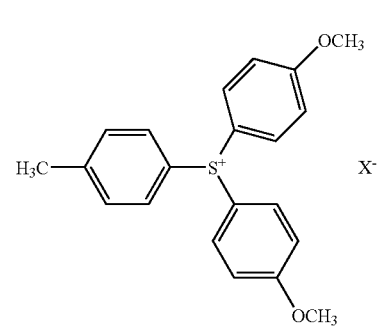

Formula (9)

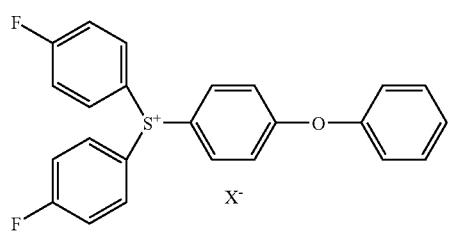

Formula (10)

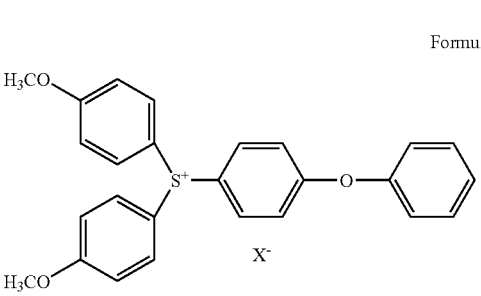

-continued

Formula (11)

[Chemical structure of triarylsulfonium salt with two H3C-substituted phenyl groups and a phenoxyphenyl group, X⁻ counterion]

Formula (12)

[Chemical structure of sulfonium salt with phenylthio-phenyl and two methylphenyl groups, X⁻ counterion]

Formula (13)

[Chemical structure of sulfonium salt with phenylthio(methylphenyl) and two methoxyphenyl groups, X⁻ counterion]

wherein X in each Formula is a non-nucleophillic anionic residue.

Item 6. The active ray-curable ink-jet ink composition of any one of Items 1-5, comprising a basic compound.

Item 7. The active ray-curable ink-jet ink composition of any one of Items 1-6, comprising a nonionic surface active agent.

Item 8. The active ray-curable ink-jet ink composition of any one of Items 1-7, comprising a photopolymerizable compound having an oxirane group in the molecule.

Item 9. The active ray-curable ink-jet ink composition of any one of Items 1-8, comprising the following photopolymerizable compounds:

(a) a compound having at least one oxetane ring in the molecule in an amount of 25-90 weight %;

(b) a compound having at least one oxirane group in the molecule in an amount of 10-70 weight %; and (c) a vinyl ether compound in an amount of 0-40 weight %, each weight % is based on the total weight of the composition.

Item 10. The active ray-curable ink-jet ink composition of any one of Items 1-9, wherein the foregoing compound which has an oxetane ring is represented by following Formula (E):

Formula (E)

[Oxetane ring structure with substituents $R_1$, $R_2$, $R_3$, $R_4$, $R_5$, $R_6$]

Wherein $R_1$-$R_6$ are each a hydrogen atom or a substituent group, but at least one group represented by $R_3$-$R_6$ is a substituent group.

Item 11. The active ray-curable ink-jet ink composition of any one of Items 1-10, exhibits a viscosity of 7-50 mPa·s at 25° C.

Item 12. An image forming method using the active ray-curable ink-jet ink composition of any one of Items 1-11, comprising the steps of:

(a) ejecting the ink from a nozzle of an ink-jet recording head to form an image on a recording material; and (b) irradiating the image with an active ray, wherein the irradiation step is carried out between 0.001-2.0 seconds after deposition of the ink composition.

Item 13. The image forming method using the active ray-curable ink-jet ink composition of any one of Items 1-11, comprising the steps of:

(a) ejecting the ink from a nozzle of an ink-jet recording head to form an image on a recording material; and (b) irradiating the image with an active ray, wherein after the irradiation step, the total ink thickness on the recording material is 2-20 μm.

Item 14. The image forming method using the active ray-curable ink-jet ink composition of any one of Items 1-11, comprising the steps of:

(a) ejecting the ink from a nozzle of an ink-jet recording head to form an image on a recording material; and (b) irradiating the image with an active ray, wherein the ink composition is ejected from an ink-jet recording head employing a line head method.

Item 15. The image forming method using the active ray-curable ink-jet ink composition of any one of Items 1-11, comprising the steps of:

(a) ejecting the ink from a nozzle of an ink-jet recording head to form an image on a recording material; and (b) irradiating the image with an active ray, wherein an image is formed by ejecting the ink composition from an ink-jet recording head of a line head method.

Item 16. An ink-jet recording apparatus which is employed in the image forming method described in any one of Items 12-15, wherein an active ray-curable ink-jet ink composition and an ink-jet recording head are heated to 35-100° C. before ejecting the ink composition.

Item 17. A triarylsulfonium salt comprising a compound represented by following Formula (T-1):

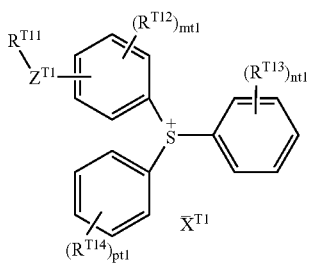

Formula (T-1)

wherein $R^{T11}$ and $R^{T12}$ are an alkyl group or an aromatic group, $Z^{T1}$ is an oxygen atom or a sulfur atom, $R^{T13}$ and $R^{T14}$ are each an alkyl group, an aromatic group, an alkoxy group, an aryloxy group, an alkylthio group or an arylthio group; mt1 is an integer of 0-4, nt1 and pt1 are each an integer of 1-5, and $X^{T1}$ is $PF_6$.

Item 18. The triarylsulfonium salt compound represented by foregoing Formula (T-1) of Item 17, is a compound represented by following Formula (T-2):

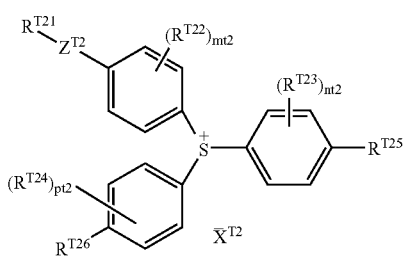

Formula (T-2)

wherein, $R^{T21}$, $R^{T22}$, $R^{T23}$ and $R^{T24}$ are each an alkyl group or an aromatic group; $Z^{T2}$ is an oxygen atom or a sulfur atom; $R^{T25}$ and $R^{T26}$ are each an alkyl group, a hydrocarbon fluoride group, an aromatic group, an alkoxy group, an aryloxy group, an alkylthio group or an arylthio group; mt2, nt2 and pt2 are each an integer of 0-4; and $X^{T2}$ is $PF_6$.

Item 19. The triarylsulfonium salt compound represented by foregoing Formula (T-2) of Item 18, is a compound represented by following Formula (T-3):

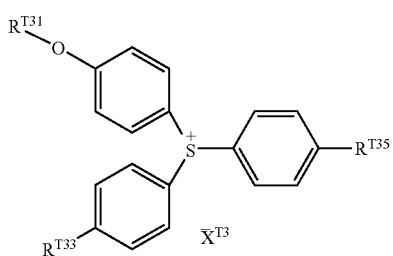

Formula (T-3)

wherein $R^{T31}$ is an alkyl group of 1-10 carbon atoms, $R^{T32}$ and $R^{T33}$ are each an alkyl group of 1-10 carbon atoms or an alkoxy group of 1-10 carbon atoms, and $X^{T3}$ is $PF_6$.

Item 20. The triarylsulfonium salt compound represented by foregoing Formula (T-2) of Item 18, is a compound represented by following Formula (T-4):

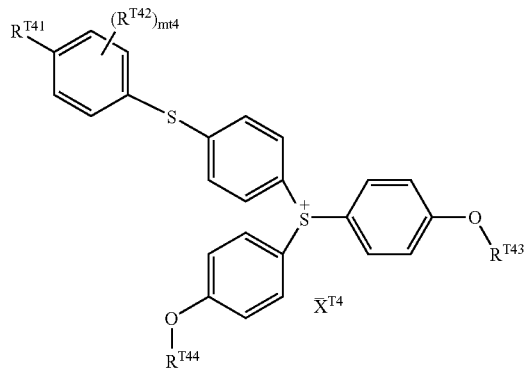

Formula (T-4)

wherein $R^{T41}$ is a hydrogen atom or an alkyl group of 1-10 carbon atoms, $R^{T42}$ is a substituent group, mt4 is an integer of 0-4, $R^{T43}$ and $R^{T44}$ are each an alkyl group of 1-10 carbon atoms, and $X^{T4}$ is $PF_6$.

Item 21. The triarylsulfonium salt compound represented by foregoing Formula (T-2) of Item 18, is a compound represented by following Formula (T-5):

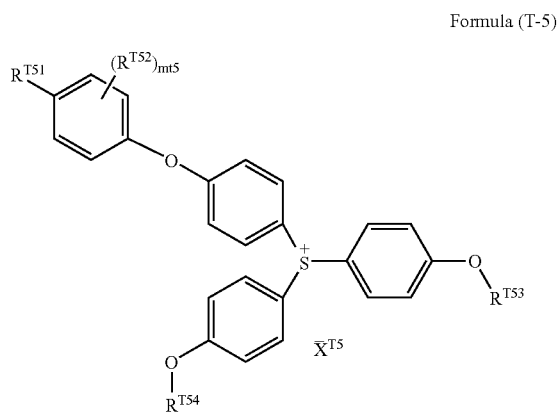

Formula (T-5)

wherein $R^{T51}$ is a hydrogen atom or an alkyl group of 1-10 carbon atoms, $R^{T52}$ is a substituent group, mt5 is an integer of 0-4, $R^{T53}$ and $R^{T54}$ are each an alkyl group of 1-10 carbon atoms, and $X^{T5}$ is $PF_6$.

Item 22. An active ray-curable composition comprising:

(a) a triarylsulfonium compound described in any one of Items 17-21; and (b) an epoxy compound.

Item 23. The active ray-curable composition of Item 22, wherein the foregoing epoxy compound is an alicyclic epoxy compound represented by following Formula (A):

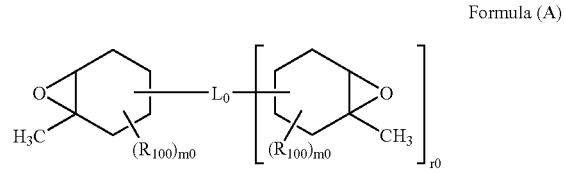

Formula (A)

wherein $R_{100}$ is a substituent group; m0 is an integer of 0-2; r0 is an integer of 1-3; $L_0$ is a r0+1 valent linking group of 1-15 carbon atoms, which may contain an oxygen atom or a sulfur atom in the principal chain, or a single bond.

Item 24. The active ray-curable composition of Item 22, wherein the foregoing epoxy compound is one selected from the alicyclic compounds represented by following Formulas (I)-(VI):

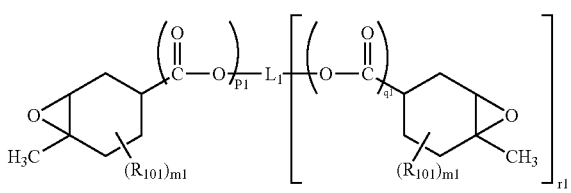

Formula (I)

wherein $R_{101}$ is a substituent group, m1 is an integer of 0-2, p1 and q1 are each 0 or 1, r1 is an integer of 1-3, and $L_1$ is a r1+1 valent linking group of 1-15 carbon atoms, which may contain an oxygen atom or a sulfur atom in the principal chain, or a single bond.

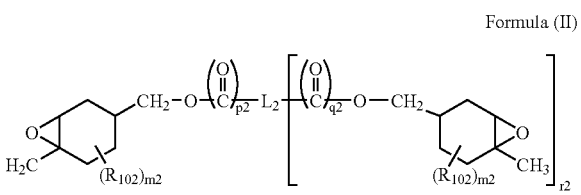

Formula (II)

wherein $R_{102}$ is a substituent group, m2 is an integer of 0-2, p2 and q2 are each 0 or 1, $L_2$ is a r2+1 valent linking group of 1-15 carbon atoms, which may contain an oxygen atom or a sulfur atom in the principal chain, or a single bond.

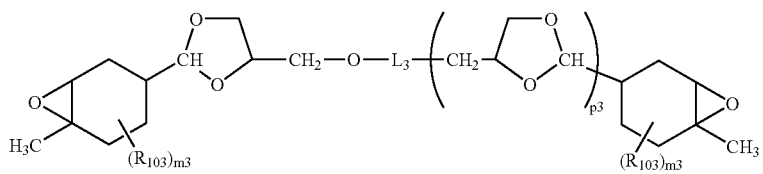

wherein $R_{103}$ is a substituent group, m3 is an integer of 0-2, p3 is 0 or 1, $L_3$ is a divalent linking group of 1-8 carbon atoms, which may contain an oxygen atom or a sulfur atom in the principal chain, or a single bond.

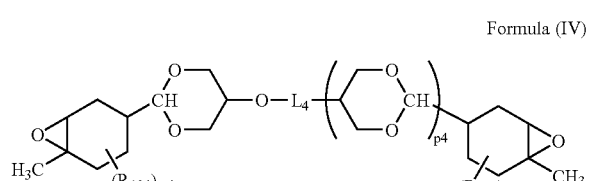

Formula (IV)

wherein $R_{104}$ is a substituent group, m4 is an integer of 0-2, p4 is 0 or 1, $L_4$ is a divalent linking group of 1-8 carbon atoms, which may contain an oxygen atom or a sulfur atom in the principal chain, or a single bond.

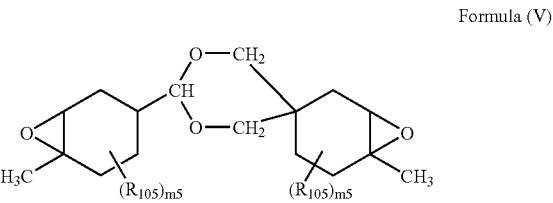

Formula (V)

wherein $R_{105}$ is a substituent group, and m5 is 1 or 2.

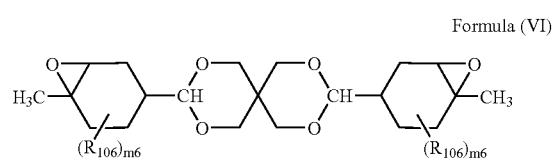

Formula (VI)

wherein $R_{106}$ is a substituent group, and m6 is an integer of 0-2.

Item 25. An active ray-curable ink-jet ink composition containing the active energy ray-curable composition described in any one of Items 22-24.

Based on the present invention, an object of this invention is to provide a triarylsulfonium salt compound, an active ray-curable ink-jet ink composition containing that compound, an active energy ray-curable composition, and an image forming method and an ink-jet recording apparatus both using the same, which are capable of stably reproducing a high-definition image onto most kinds of recording materials under various printing conditions without release of benzene, which is toxic to humans.

DETAILED DESCRIPTION OF THE PREFERRED EMBODIMENT

Figure 1:
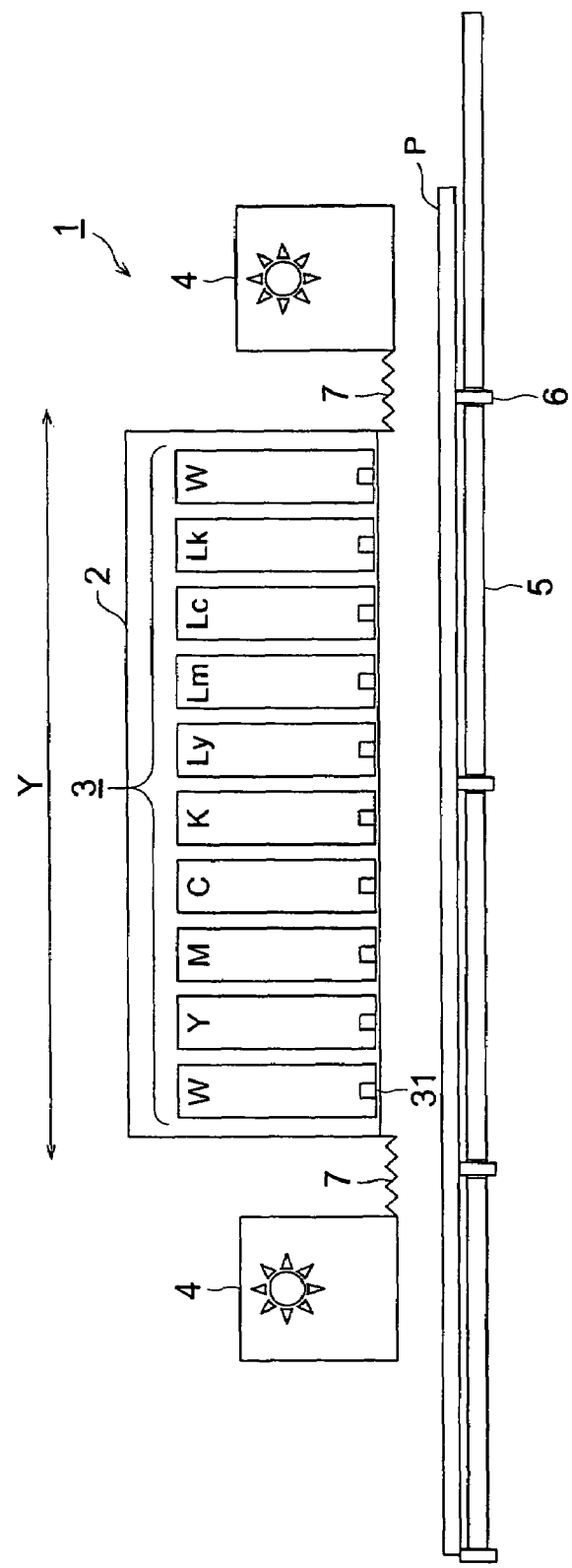
FIG. 1 is a front view showing an example of the constitution of substantial parts of an ink-jet recording apparatus employed in this invention.

The best mode to conduct this invention will be detailed below.

The inventors found that in an active energy ray-curable ink-jet ink composition (from now on, referred to as an active ray-curable ink or simply as an ink), ejection stability and curability are markedly improved by employing an active ray-curable ink-jet ink composition which contains an onium salt as a photo-induced acid generating agent, does not generate benzene by the active ray radiation, and also contains an oxetane containing compound as a photopolymerizable compound, resulting in excellent ejection stability and curability without any adverse effects of printing conditions (such as temperature and humidity). Thus, the inventors achieved this invention.

In the past, a cationic polymerizable ink composition was prepared employing a photo-induced acid generating agent which generated benzene as a resolvent by active ray radiation, examples of which typically included UV16992 (being a triarylsulfonium salt, produced by The Dow Chemical Company). However, this ink composition was hardly ever employed in the food industries due to generation of benzene, but also had the drawback of unstable ejection by environment (such as temperature and humidity) Therefore, it was impossible to form a high definition image with ink-jet recording using this ink composition. On the other hand, as an onium salt (being a photo-induced acid generating agent) which does not generate benzene, known are IRGACURE 250 (being a diaryliodonium, produced by Ciba Specialty Chemicals) and CI 5102 (being a diaryliodonium salt, produced by NIPPON SODA CO., LTD.). However, there have been no practical examples in use as an ink-jet ink composition which is capable of stable ejection employing an onium salt and not generating benzene by active ray radiation and including the above salts.

Specifically, in cases when the onium salt is employed in combination with an oxetane containing compound, ejection stability of the ink composition, which is considered to be a very important characteristics, is extremely enhanced, and the ink dot diameter after deposition onto a recording material can be easily controlled without influencing of curing conditions, resulting in formation of high definition images with good reproducibility. This is therefore a revolutionary constitution.

Further, in cases when the onium salt which does not generate benzene by active ray radiation is employed as a photo-induced acid generating agent, it is preferable that a basic compound or a nonionic surface active agent is simultaneously employed to further enhance ejection stability.

More preferable is for the ejection stability enhancement to contain, as photopolymerizable compounds, 25-90 weight % of an oxetane containing compound, 10-70 weight % of a compound having an oxyrane group, and 0-40 weight % of a vinyl ether compound, resulting in further enhancement of both the foregoing curability and ejecting stability.

Further, the inventors found that by employing an oxetane compound represented by foregoing Formula (E), curability and also ejection stability were favorably enhanced. In cases when only an oxetane compound is employed, it is more preferable to use a monofunctional oxetane compound together with a multifunctional oxetane compound having at least two oxetane rings.

The present invention will be detailed below.

Firstly, an onium salt (being a photo-induced acid generating agent), which does not generate benzene by active ray radiation, and which is contained in the ink of this invention, will be described.

The expression "does not generate benzene by active ray radiation" in this invention means that benzene is basically not generated, and specifically, it means that when a sufficient amount of active ray radiation, to decompose the photo-induced acid generating agent, is applied to the ink layer surface at 30° C., a layer of which is printed at a thickness of 15 µm in about 100 cm$^2$ using the ink containing the onium salt (being a photo-induced acid generating agent) in an amount of 5 weight % in the ink composition, the volume of generated benzene is infinitesimal, in the range of less than 5 µg or zero. As the onium salt, preferred is a sulfonium salt or an iodonium salt, and any compound containing a benzene ring, which bonds to S$^+$ or I$^+$ and has a substituent group, may satisfy the above requirements.

As a sulfonium salt, preferred are sulfonium salt compounds represented by foregoing Formulas (1)-(4), and any compound may containing a benzene ring which bonds to S$^+$ and has a substituent group, will satisfy the above requirements.

In foregoing Formulas (1)-(4), $R_1$-$R_{17}$ are each a hydrogen atom or a substituent group, $R_1$ and $R_3$ are not a hydrogen atom at the same time, $R_4$ and $R_7$ are not a hydrogen atom at the same time, $R_8$ and $R_{11}$ are not a hydrogen atom at the same time, $R_{12}$ and $R_{17}$ are not a hydrogen atom at the same time, and $R_1$-$R_3$ in Formula (1) are not a phenylthio group or a phenoxy group.

As substituent groups represented by $R_1$-$R_{17}$, preferably listed are an alkyl group such as a methyl group, ethyl group, propyl group, isopropyl group, butyl group, isobutyl group, t-butyl group, pentyl group, and hexyl group; an alkoxy group such as a methoxy group, ethoxy group, propoxy group, butoxy group, hexyloxy group, decyloxy group, and dodecyloxy group; a carbonyl group such as an acetoxy group, propionyloxy group, decylcarbonyloxy group, dodecylcarbonyloxy group, methoxycarbonyl group, ethoxycarbonyl group, and benzoyloxy group; a halogen atom such as fluorine, chlorine, bromine and iodine; a cyano group, a nitro group, or a hydroxyl group.

X is a non-nucleophillic anionic residue, for example, a halogen atom such as F, Cl, Br or I; $B(C_6F_5)$; $R_{18}COO$; $R_{19}SO_3$; $SbF_6$; $AsF_6$; $PF_6$; or $BF_4$, wherein R18 and R19 are each an alkyl group such as a methyl group, ethyl group, propyl group, and butyl group; a halogen atom such as fluorine, chlorine, bromine and iodine; a nitro group; a cyano group; or an alkyl group or phenyl group which may be substituted with an alkoxy group such as a methoxy group and ethoxy group. Of these, from the viewpoint of safety, preferred are $B(C_6F_5)$ and $PF_6$.

The foregoing compounds can be readily synthesized using the well-known methods, similar to the photo-induced acid generating agents described in The Chemical Society of Japan, vol. 71, No. 11, 1998, and "Imaging yo Yuki Zairyo" (Organic Materials for Imaging), edited by Yuki Electronics Zairyo Kenkyu-kai, published by Bunshin Shuppan (1993).

In this invention, it is specifically preferable that the sulfonium salts represented by foregoing Formulas (1)-(4) are at least one sulfonium salt selected from the ones represented by foregoing Formulas (5)-(13). X is the same as before, being a non-nucleophillic anionic residue.

As exemplified compounds including iodonium salts, listed are the following compounds, other than those represented by foregoing Formulas (5)-(13), wherein X is $B(C_6F_5)_4$, $PF_6$, Br, and $BF_4$.
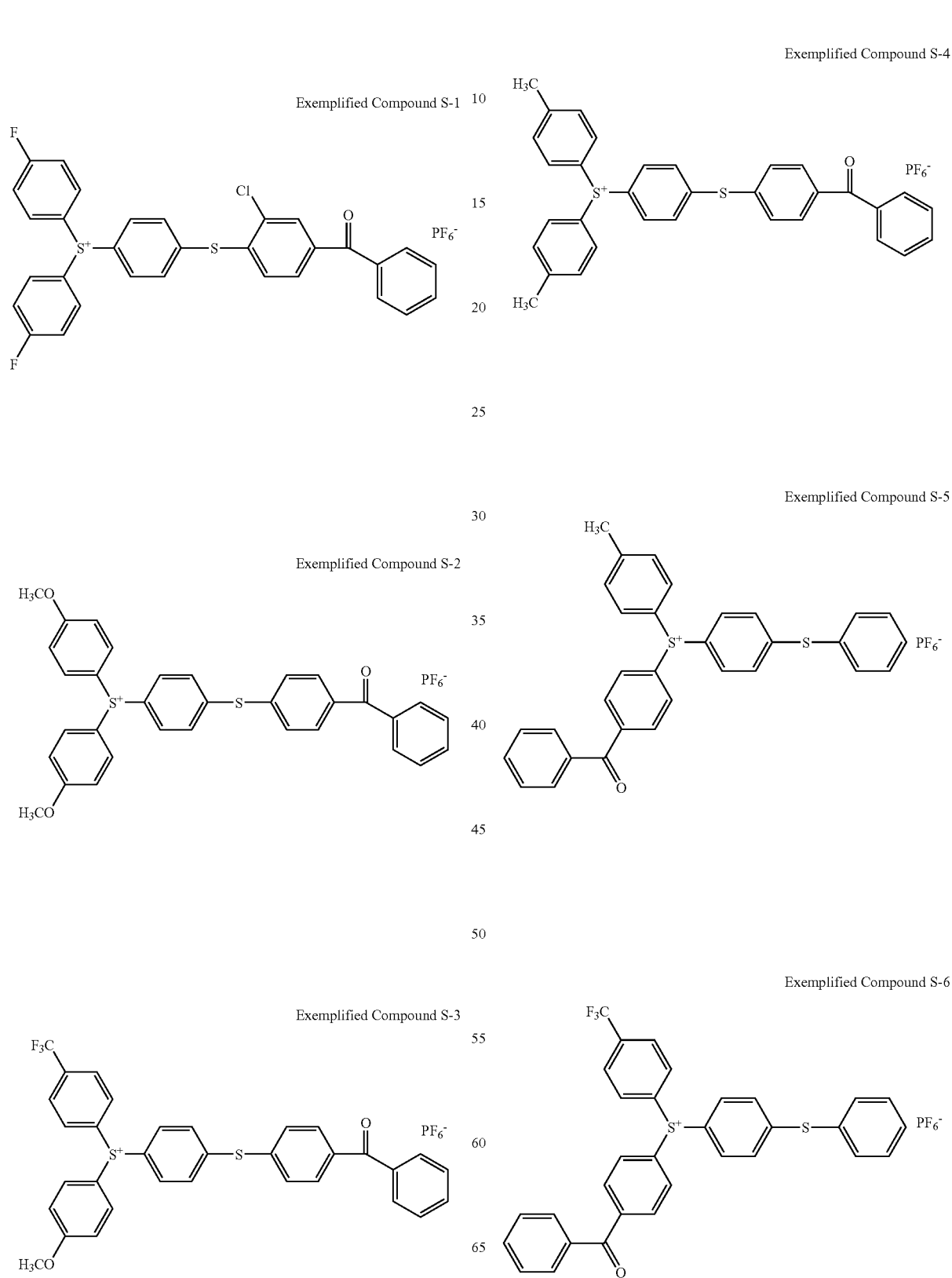

-continued
Exemplified Compound S-7
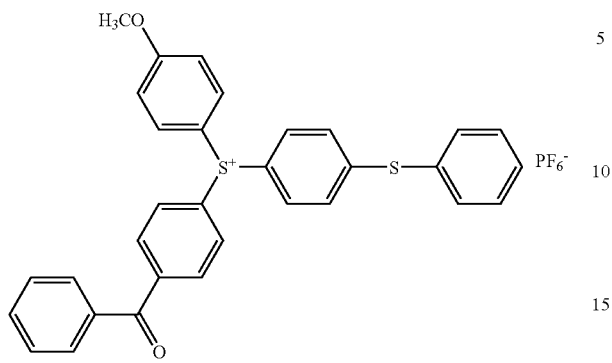
Exemplified Compound S-8
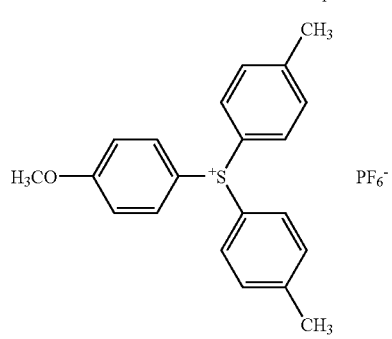
Exemplified Compound S-9
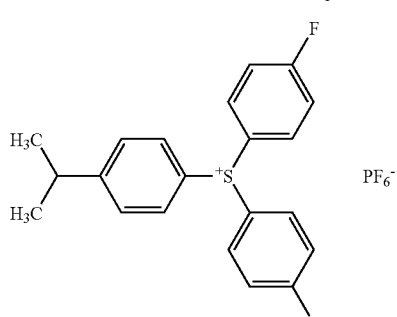
Exemplified Compound S-10
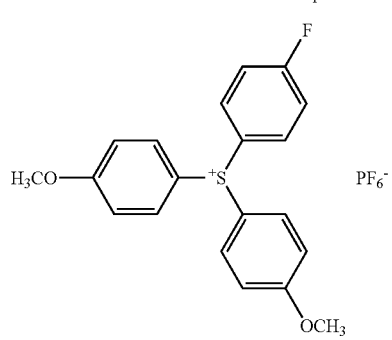
Exemplified Compound S-11
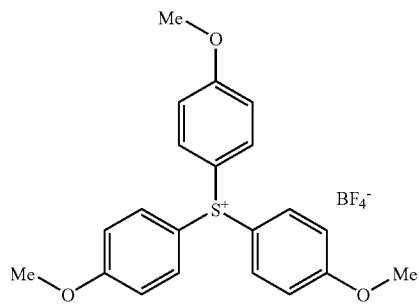
Exemplified Compound S-12
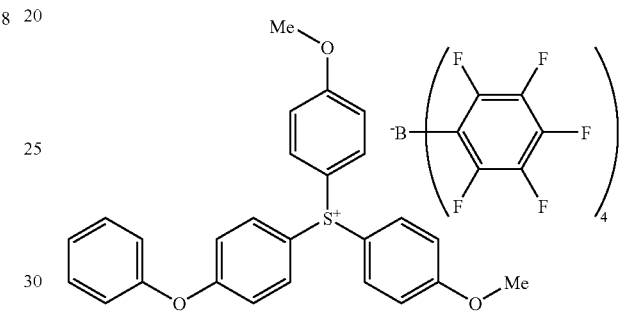
Exemplified Compound S-13
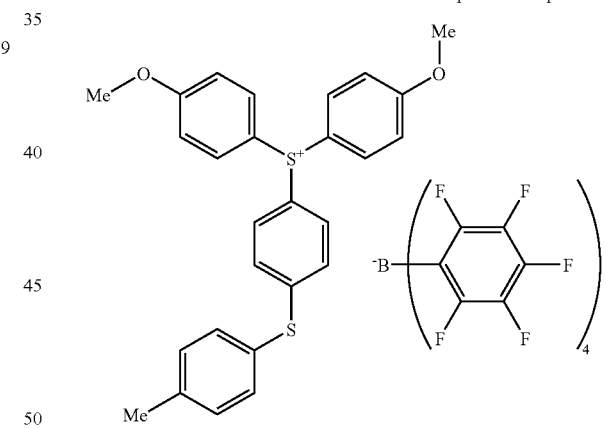
Exemplified Compound I-1
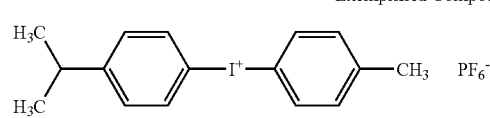
Exemplified Compound I-2
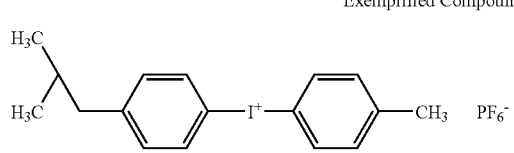

-continued

Exemplified Compound I-3

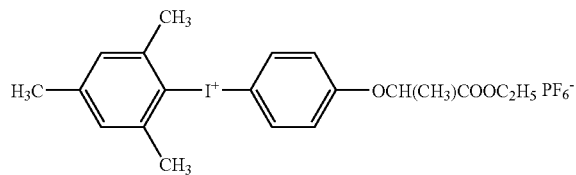

Exemplified Compound I-4

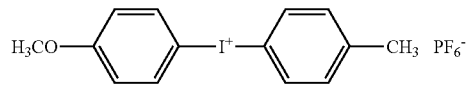

Exemplified Compound I-5

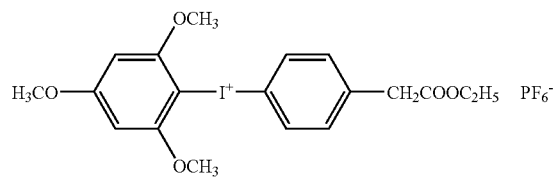

Triarylsulfonium Salt Compound

In this invention, an onium salt which does not generate benzene is characterized by being a triarylsulfonium salt compound represented by foregoing Formula (T-1). Further, in this invention, triarylsulfonium salts represented by foregoing Formulas (T-2)-(T-5) are specifically preferred, and of those, triarylsulfonium salts represented by Formula (T-3) are more preferably employed. These compounds are particularly superior in photocurability, operator safety and humidity resistance. Compounds represented by Formula (T-1)

$R^{T11}$ and $R^{T12}$ are an alkyl group or an aromatic group. The alkyl group may be a straight chain, a branched chain or a cyclic one, for example, a methyl group, ethyl group, propyl group, isopropyl group, tert-butyl group, pentyl group, hexyl group, octyl group, dodecyl group, tridecyl group, tetradecyl group, pentadecyl group, cyclopentyl group, or a cyclohexyl group. The aromatic group may be an aromatic hydrocarbon ring group or an aromatic heterocyclic ring group, or may have a condensed ring, for example, an aromatic hydrocarbon group such as a phenyl group or a naphthyl group; an aromatic heterocyclic ring group such as a furyl group, thienyl group, pyridyl group, pyridazyl group, pyrimidyl group, pyrazyl group, triazyl group, imidazolyl group, pyrazolyl group, thiazolyl group, benzoimidazolyl group, benzoxazolyl group, quinazolyl group, or a phthalazyl group.

The alkyl group or the aromatic group described above may further be substituted, and these substituent groups may be combined with each other to form a ring, and may also have a condensed ring. As examples of the substituent groups, other than the above alkyl group, listed are an alkenyl group (such as a vinyl group or an allyl group); an alkynyl group (such as an ethynyl group or a propargyl group); an aromatic hydrocarbon group (such as a phenyl group or a naphthyl group); a heteroaromatic group (such as a furyl group, thienyl group, pyridyl group, pyridazyl group, pyrimidyl group, pyrazyl group, triazyl group, imidazolyl group, pyrazolyl group, thiazolyl group, benzoimidazolyl group, benzoxazolyl group, quinazolyl group, or a phthalazyl group); a heterocyclic group (such as a pyrrolidyl group, imidazolidyl group, morpholyl group, or an oxazolidyl group); an alkoxy group (such as a methoxy group, ethoxy group, propyloxy group, pentyloxy group, hexyloxy group, octyloxy group, or a dodecyloxy group); a cycloalkoxy group (such as a cyclopentyloxy group, or a cyclohexyloxy group); an aryloxy group (such as a phenoxy group or naphthyloxy group); an alkylthio group (such as a methylthio group, ethylthio group, propylthio group, pentylthio group, hexylthio group, octylthio group, or a dodecylthio group); a cycloalkylthio group (such as a cyclopentylthio group or cyclohexylthio group); an arylthio group (such as a phenylthio group or anaphthylthio group); an alkoxycarbonyl group (such as a methyloxycarbonyl group, ethyloxycarbonyl group, butyloxycarbonyl group, octyloxycarbonyl group, or dodecyloxycarbonyl group); an aryloxycarbonyl group (such as a phenyloxycarbonyl group or naphthyloxycarbonyl group); a sulfamoyl group (such as an aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group, or 2-pyrizylaminosulfonyl group); an acyl group (such as an acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group, or piridylcarbonyl group); an acyloxy group (such as an acetyloxy group, ethylcarbonyloxy group, butylcarbonyloxy group, octylcarbonyloxy group, dodecylcarbonyloxy group, or phenylcarbonyloxy group); an amide group (such as a methylcarbonylamino group, ethylcarbonylamino group, dimethylcarbonylamino group, propylcarbonylamino group, pentylcarbonylamino group, cyclohexylcarbonylamino group, 2-ethylhexylcarbonylamino group, octylcarbonylamino group, dodecylcarbonylamino group, or naphthylcarbonylamino group); a carbamoyl group (such as an aminocarbonyl group, naphthylaminocarbonyl group, dimethylaminocarbonyl group, propylaminocarbonyl group, pentylaminocarbonyl group, cyclohexylaminocarbonyl group, octylaminocarbonyl group, 2-ethylhexylaminocarbonyl group, dodecylaminocarbonyl group, phenylaminocarbonyl group, naphthylaminocarbonyl group, or 2-pyridylaminocarbonyl group); a ureido group (such as a methylureido group, ethylureido group, pentylureido group, cyclohexylureido group, octylureido group, dodecylureido group, phenylureido group, naphthylureido group, or 2-pyridylaminoureido group); a sulfinyl group (such as a methylsulfinyl group, ethylsulfinyl group, butylsulfinyl group, cyclohexylsulfinyl group, 2-ethylhexylsulfinyl group, dodecylsulfinyl group, phenylsulfinyl group, naphthylsulfinyl group, or 2-pyridylsulfinyl group); an alkylsulfonyl group (such as methylsulfonyl group, ethylsulfonyl group, butylsulfonyl group, cyclohexylsulfonyl group, 2-ethylhexylsulfonyl group, or dodecylsulfonyl group); an arylsulfonyl group (such as a phenylsulfonyl group, naphthylsulfonyl group, or 2-pyridylsulfonyl group); an amino group (such as an amino group, ethylamino group, dimethylamino group, butylamino group, cyclopentylamino group, 2-ethylhexylamino group, dodecylamino group, anilino group, naphthylamino group, or 2-piridylamino group); a halogen atom (such as a fluorine atom, chlorine atom, or a bromine atom); a fluorocarbon group (such as a fluoromethyl group, trifluoromethyl group, pentafluoroethyl group, or pentafluorophenyl group); a cyano group; a nitro group; a hydroxyl group; a mercapto group; and a silyl group (such as a trimethylsilyl group, triisopropylsilyl group, triphenylsilyl group, or phenyldiethylsilyl group). These substituent groups may further be substituted by the above substituent groups, and these substituent groups may combine with each other to form a ring.

The alkyl group or the aromatic group represented by $R^{T11}$ or $R^{T12}$ may have or may have not a further substituent group, and those are preferably an unsubstituted alkyl or aromatic group, an alkyl group substituted with a haligen atom, or an aromatic group substituted with an alkoxy group, but more preferably an unsubstituted alkyl or aromatic group, an alkyl group substituted with a fluorine atom, or an aromatic group substituted with an alkoxy group. Examples of the alkyl groups substituted with a fluorine atom include a fluoromethyl group, trifluoromethyl group, pentafluoroethyl group, and pentafluorophenyl group.

$Z^{T1}$ is an oxygen atom or a sulfur atom, and preferably bonds at the ortho- or para-position to the benzene ring which is linked with a sulfonium ion, and more preferably bonds at the para-position.

$R^{T13}$ and $R^{T14}$ are each an alkyl group, aromatic group, alkoxy group, aryloxy group, alkylthio group, or an arylthio group. The alkyl group and an aromatic group are the same as in $R^{T11}$ or $R^{T12}$.

The alkoxy group and the aryloxy group are the groups in which the oxygen atom bonds to the group of the same as above $R^{T11}$ or $R^{T12}$ at only one location, examples of which are, for example, an alkoxy group (such as a methoxy group, ethoxy group, propyloxy group, pentyloxy group, hexyloxy group, octyloxy group, dodecyloxy group, fluoromethyl group, trifluoromethyl group, pentafluoroethyl group, or pentafluorophenyl group); a cycloalkoxy group (such as a cyclopentyloxy group, or cyclohexyloxy group); or an aryloxy group (such as a phenoxy group or naphthyloxy group).

The alkylthio group and the arylthio group are the groups in which the sulfur atom bonds to the same group as above $R^{T11}$ or $R^{T12}$ at only one location, examples of which are, for example, an alkilthio group (such as a methylthio group, ethylthio group, propylthio group, pentylthio group, hexylthio group, octylthio group, or dodecylthio group); a cycloalkylthio group (such as a cyclopentylthio group, or cyclohexylthio group); an arylthio group (such as a phenylthio group, or naphthylthio group). The above aromatic group, aryloxy group and arylthio group may have a condensed ring.

The above alkyl group, aromatic group, alkoxy group, aryloxy group, alkylthio group or arylthio group may further have a substituent group, and these substituent groups may combine with each other to form a ring, and further may have a condensed ring. As examples of those substituent groups, listed are synonymous groups as the substituent groups of above $R^{T11}$, and these groups may further be substituted with a substituent group, and still further these groups may combine with each other to form a ring. The alkyl group, aromatic group, alkoxy group, aryloxy group, alkylthio group, and arylthio group, represented by $R^{T13}$ and $R^{T14}$, may have a further substituent group, but are preferably an unsubstituted alkyl group, aromatic group, alkoxy group, aryloxy group, alkylthio group, or arylthio group; or an alkyl group substituted with a halogen atom; or an aromatic group substituted with an alkoxy group; and more preferably are an unsubstituted alkyl group, aromatic group, alkoxy group, aryloxy group, alkylthio group, or an arylthio group; or an alkyl group substituted with a fluorine atom; or an aromatic group substituted with an alkoxy group. Examples of alkyl groups substituted with a fluorine atom include a fluoromethyl group, trifluoromethyl group, pentafluoroethyl group, and pentafluorophenyl group.

mt1 is an integer of 0-4, preferably 0-3, and more preferably 0-2. nt1 and pt1 are each an integer of 1-5, preferably 1-3, and more preferably 1-2.

A plurality of $R^{T12}$, $R^{T13}$ and $R^{T14}$ each may be the same or different, and $R^{T11}$ and $R^{T12}$ or plural $R^{T12}$'s may combine with each other to form a ring, $R^{T12}$ and $R^{T13}$ or plural $R^{T13}$'s may combine with each other to form a ring, and $R^{T12}$ and $R^{T14}$ may also combine with each other to form a ring. At least one $R^{T13}$ preferably combines with the benzene ring bonded with a sulfonium ion at the ortho- or para-position, and more preferably at the para-position. At least one $R^{T14}$ preferably combines with the benzene ring bonded with a sulfonium ion at the ortho- or para-position, and more preferably at the para-position. $X^{T1}$ is $PF_6^-$.

Compounds Represented by Formula (T-2)

In Formula (T-2), $R^{T21}$, $R^{T22}$, $R^{T23}$ and $R^{T24}$ are an alkyl group or an aromatic group. The alkyl group and the aromatic groups are the same as above $R^{T11}$, and a plurality of $R^{T21}$, $R^{T22}$, $R^{T23}$ and $R^{T24}$ may each be the same or different, and $R^{T21}$ and $R^{T22}$ or plural $R^{T22}$'s may combine with each other to form a ring, and $R^{T23}$ and $R^{T25}$ or plural $R^{T23}$'s may also combine with each other to form a ring, and further $R^{T24}$ and $R^{T26}$ or plural $R^{T24}$'s may combine with each other to form a ring, and $R^{T22}$ and $R^{T23}$ may combine with each other to form a ring, also $R^{T23}$ and $R^{T24}$ may combine with each other to form a ring, and $R^{T22}$ and further $R^{T24}$ may also combine with each other to form a ring.

$Z^{T2}$ is an oxygen atom or a sulfur atom, $R^{T25}$ and $R^{T26}$ are each an alkyl group, aromatic group, alkoxy group, aryloxy group, alkylthio group, or arylthio group. The alkyl group, aromatic group, alkoxy group, aryloxy group, alkylthio group, or arylthio group is the same group of above $R^{T13}$; and mt2, nt2 and pt2 are each an integer of 0-4, preferably 0-2, and more preferably 0 or 1; while $X^{T2}$ is $PF_6^-$.

Compounds Represented by Formula (T-3)

In Formula (T-3), $R^{T31}$ is an alkyl group of 1-10 carbon atoms. The alkyl group may be a straight chain, a branched chain, or a cyclic form. Examples include a methyl group, ethyl group, propyl group, isopropyl group, tert-butyl group, pentyl group, hexyl group, heptyl group, octyl group, tert-amyl group, cyclopentyl group, and cyclohexyl group; and further these alkyl groups may have a substituent group. Examples of the substituent groups are the same as the above $R^{T11}$. $R^{T31}$ is preferably an alkyl group of 1-6 carbon atoms, and more preferably an alkyl group of 1-4 carbon atoms.

$R^{T32}$ and $R^{T33}$ are each an alkyl group of 1-10 carbon atoms or alkoxy group of 1-10 carbon atoms. The alkyl group is the same group of above $R^{T31}$, and the alkoxy group is, for example, a methoxy group, ethoxy group, propyloxy group, isopropyloxy group, tert-butyloxy group, pentyloxy group, octyloxy group, cyclopentyloxy group, or a cyclohexyloxy group. $R^{T32}$ and $R^{T33}$ are each preferably an alkyl group of 1-6 carbon atoms or an alkoxy group of 1-6 carbon atoms, more preferably are each an alkyl group of 1-4 carbon atoms or an alkoxy group of 1-4 carbon atoms, and still more preferably a methyl group or a methoxy group. $X^{T3}$ is $PF_6^-$.

Compounds Represented by Formula (T-4)

In Formula (T-4), $R^{T41}$ is an alkyl group of 1-10 carbon atoms. The alkyl group may be a straight chain, a branched chain or a cyclic form. As examples, listed are a methyl group, ethyl group, propyl group, isopropyl group, tert-butyl group, pentyl group, hexyl group, heptyl group, octyl group, tert-amyl group, cyclopentyl group, and a cyclohexyl group; and these alkyl groups may have a substituent group. Examples of such substituent groups are the same as the above $R^{T11}$. $R^{T41}$ is preferably an alkyl group of 1-6 carbon atoms, more preferably an alkyl group of 1-4 carbon atoms, and is still more preferably a methyl group.

$R^{T42}$ is a substituent group, and the substituent group is the same as the above $R^{T11}$.

mt4 is an integer of 0-4, preferably 0-2, and more preferably 0 or 1.

$R^{T43}$ and $R^{T44}$ are each an alkyl group of 1-10 carbon atoms, the alkyl group being the same substituent group as the above $R^{T31}$. $R^{T43}$ and $R^{T44}$ are each preferably an alkyl group of 1-6 carbon atoms, more preferably an alkyl group of 1-4 carbon atoms, and is still more preferably a methyl group. $X^{T4}$ is $PF_6^-$.

Compounds Represented by Formula (T-5)

In Formula (T-5), $R^{T51}$ is a hydrogen atom or an alkyl group of 1-10 carbon atoms, said alkyl group being the same substituent group as the above $R^{T31}$. $R^{T51}$ is preferably a hydrogen atom or an alkyl group of 1-6 carbon atoms, and more preferably a hydrogen atom or an alkyl group of 1-4 carbon atoms.

$R^{T52}$ is a substituent group, in which the substituent groups are the same as the above $R^{T11}$.

Mt5 is an integer of 0-4, preferably 0-2, and more preferably 0 or 1.

$R^{T53}$ and $R^{T54}$ are each an alkyl group of 1-10 carbon atoms, in which the alkyl group is the same substituent group as the above $R^{T31}$. $R^{T53}$ and $R^{T54}$ are each preferably an alkyl group of 1-6 carbon atoms, more preferably an alkyl group of 1-4 carbon atoms, and still more preferably is a methyl group. $X^{T5}$ is $PF_6^-$.

Specific examples of the triarylsulfonium salt compounds represented by foregoing Formulas (T-1)-(T-5), which are employable in this invention, are shown below, but the present invention is not limited to these examples.

-continued

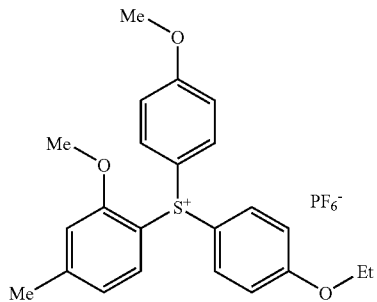

TAS-3

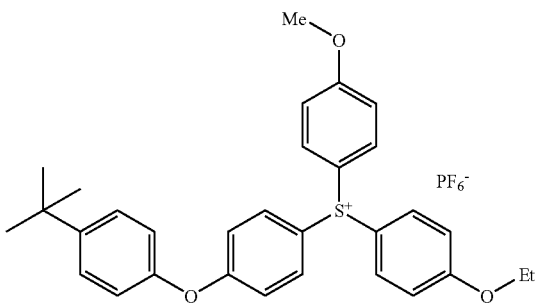

TAS-4

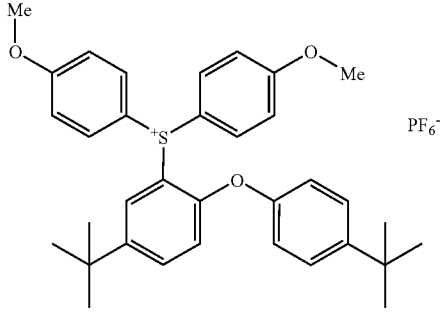

TAS-5

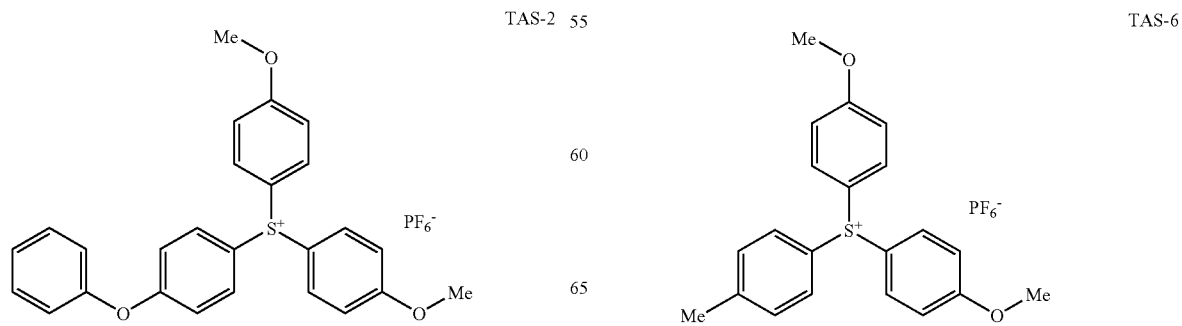

TAS-1

TAS-2

TAS-6

-continued
TAS-7
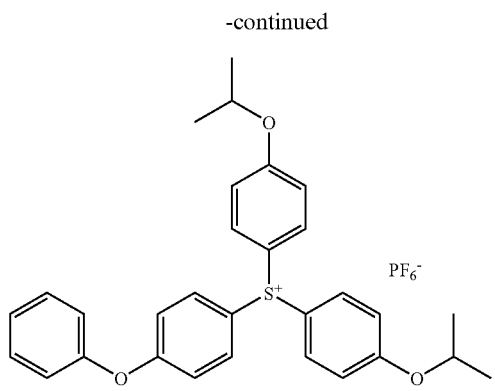
TAS-8
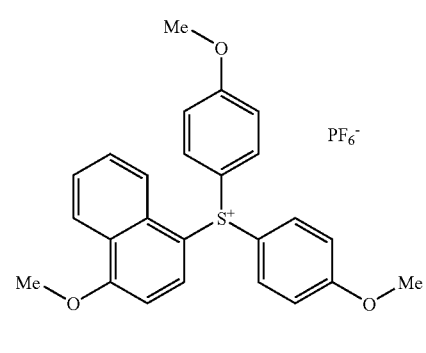
TAS-9
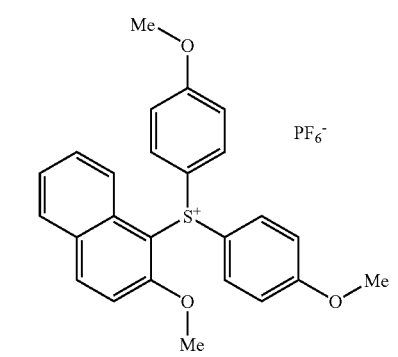
TAS-10
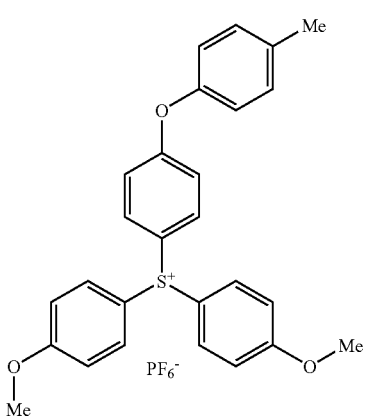
TAS-11
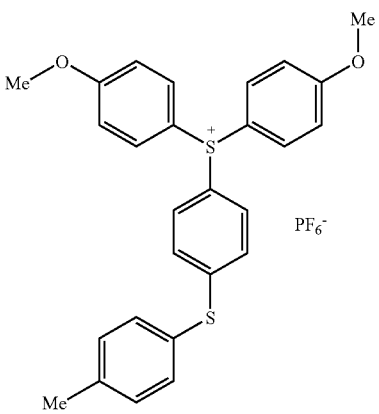
TAS-12
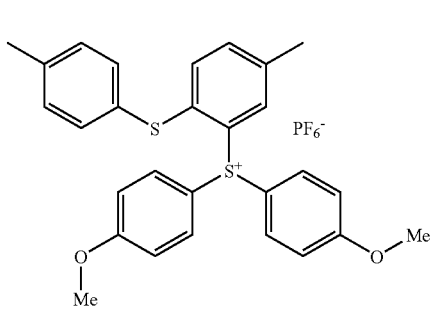
TAS-13
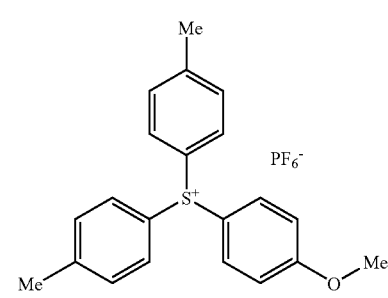
TAS-14
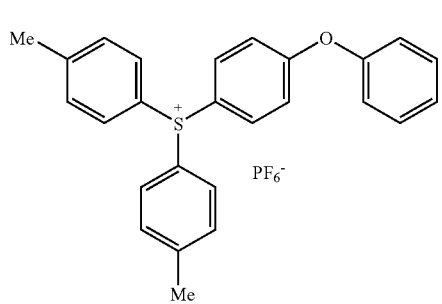

-continued
TAS-15
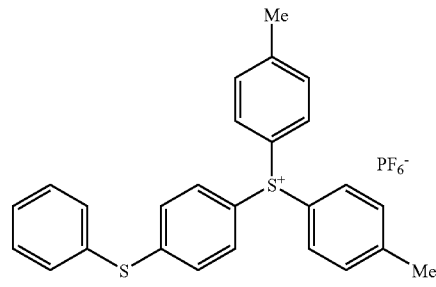
TAS-16
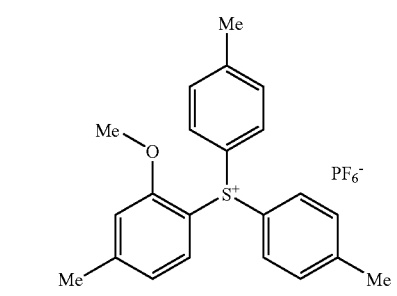
TAS-17
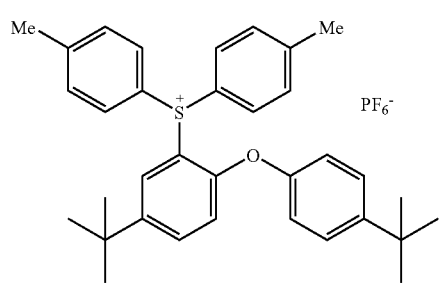
TAS-18
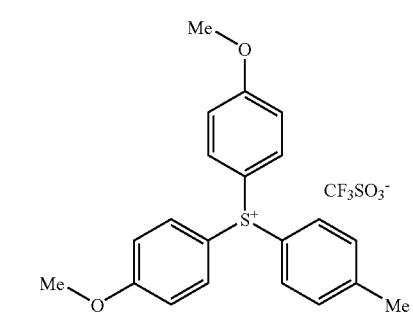
-continued
TAS-19
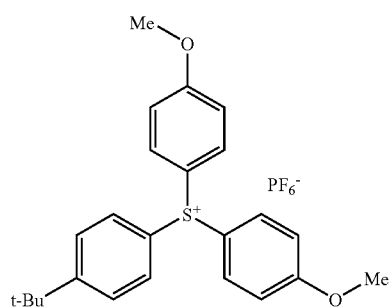
TAS-20
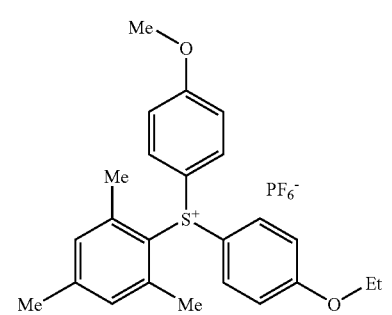
TAS-21
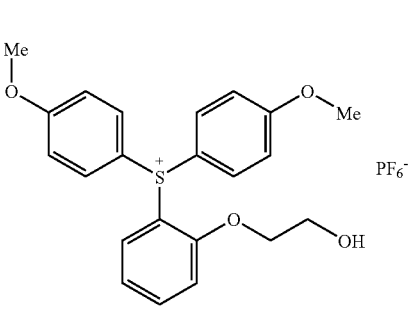
TAS-22
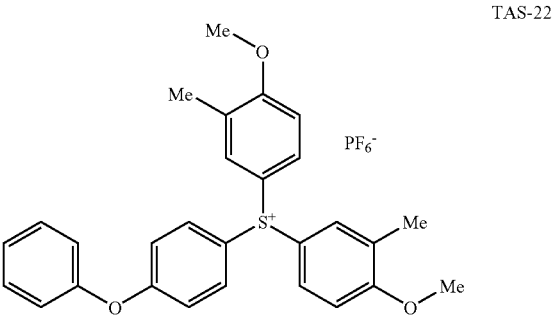

TAS-23
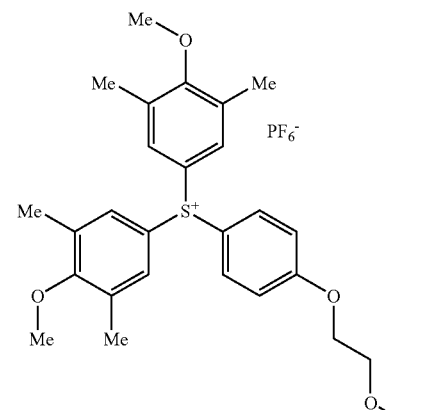
TAS-24
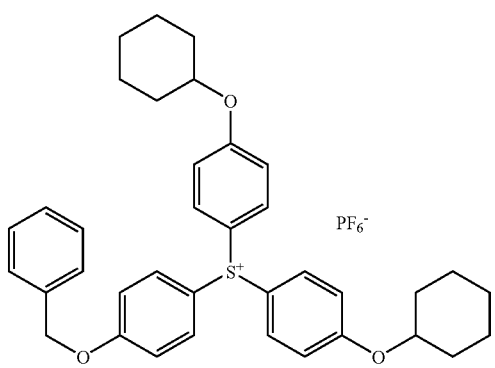
TAS-25
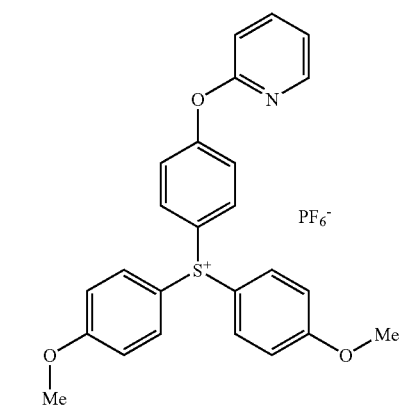
TAS-26
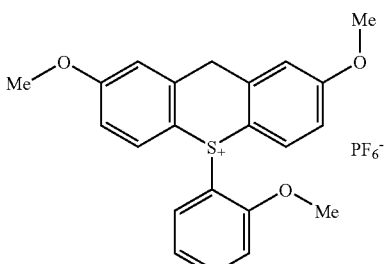
TAS-27
TAS-28
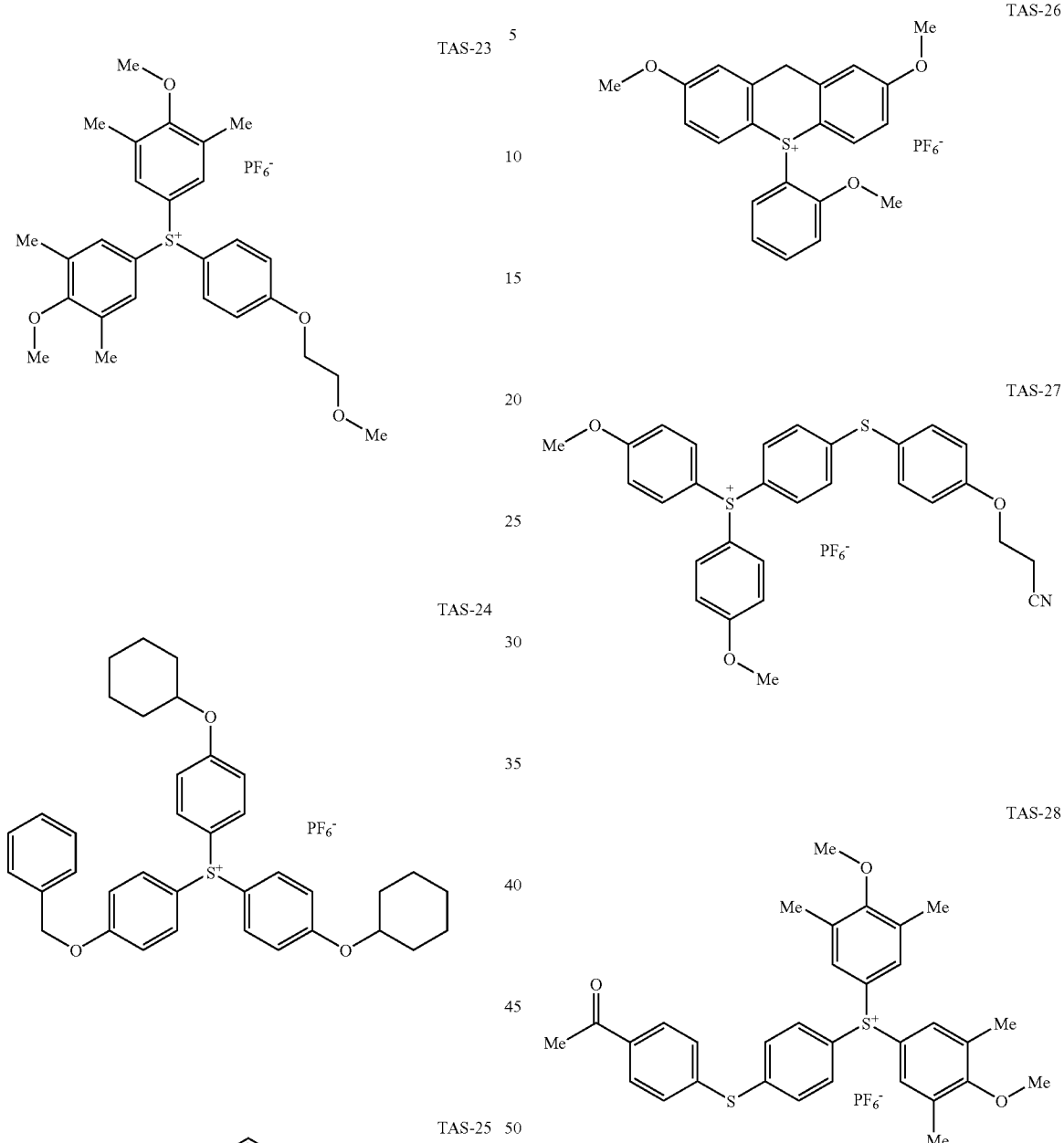
TAS-29
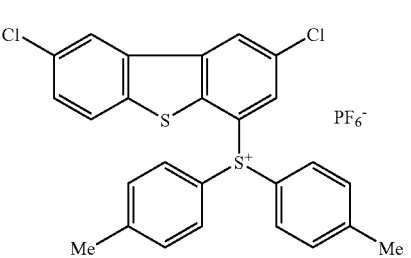

-continued
TAS-30
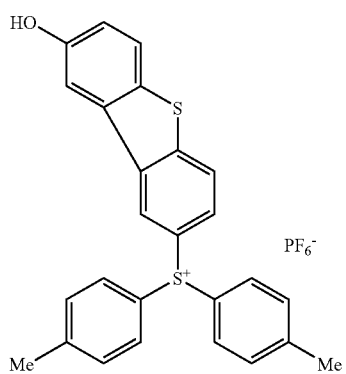
TAS-31
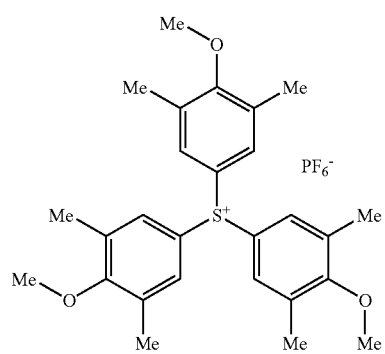
TAS-32
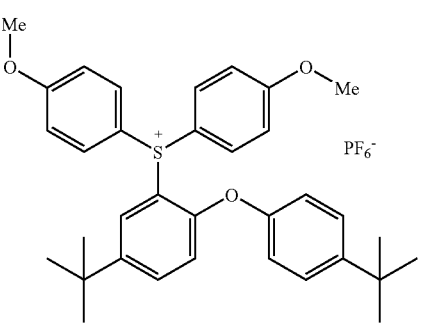
TAS-33
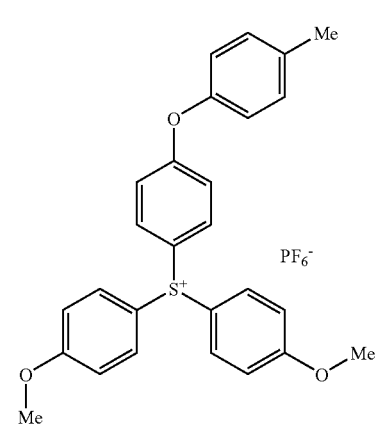
-continued
TAS-34
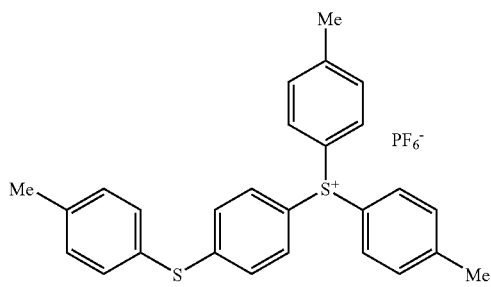
TAS-35
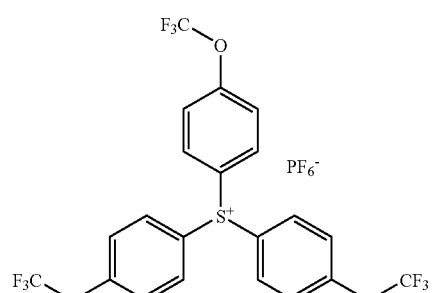
TAS-36
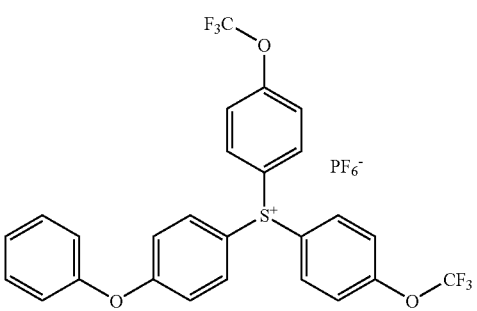
TAS-37
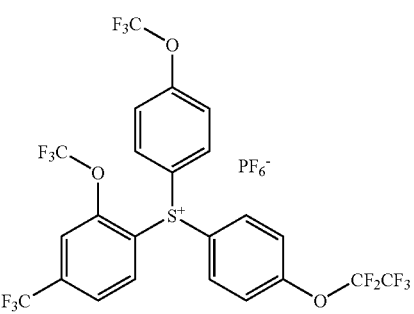

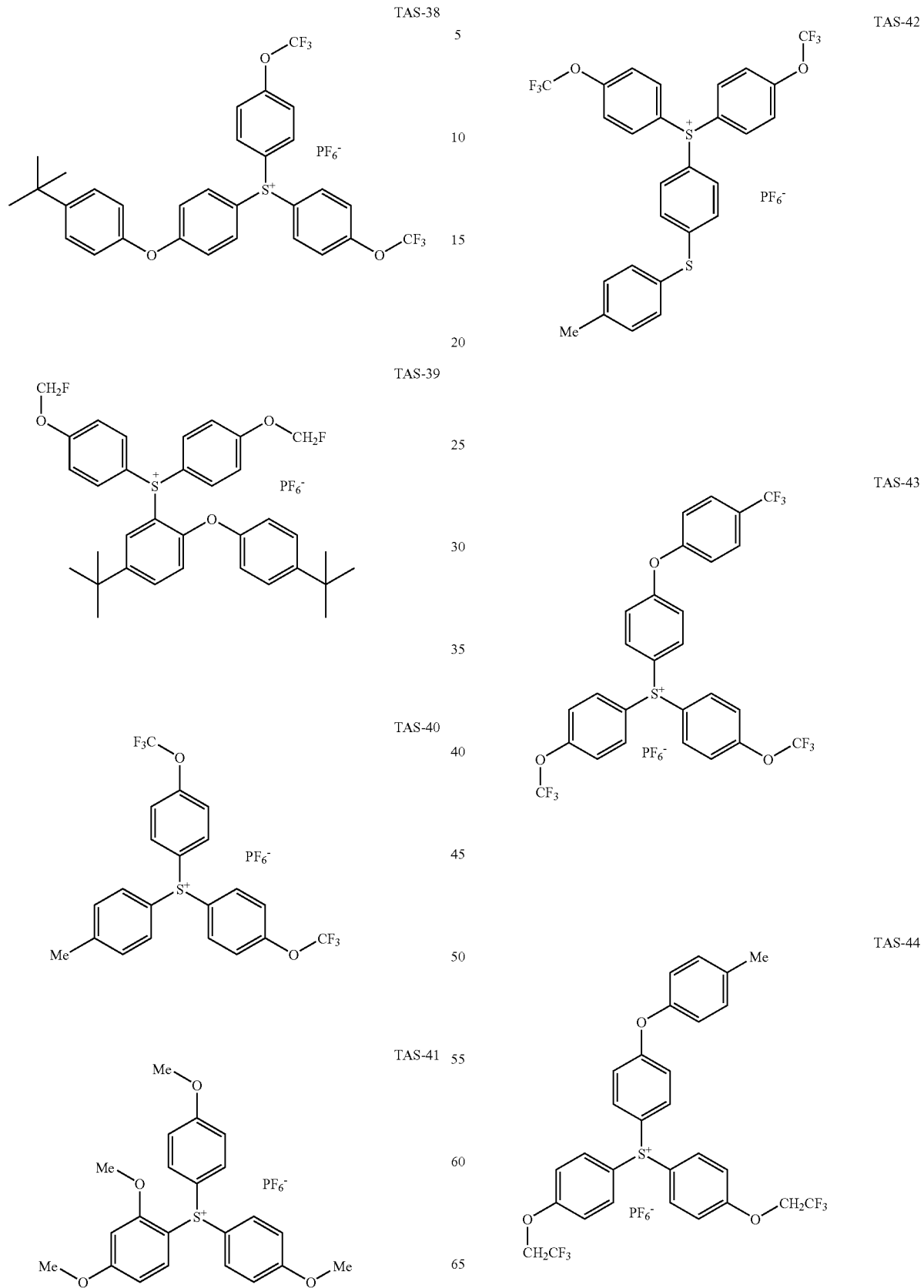

-continued

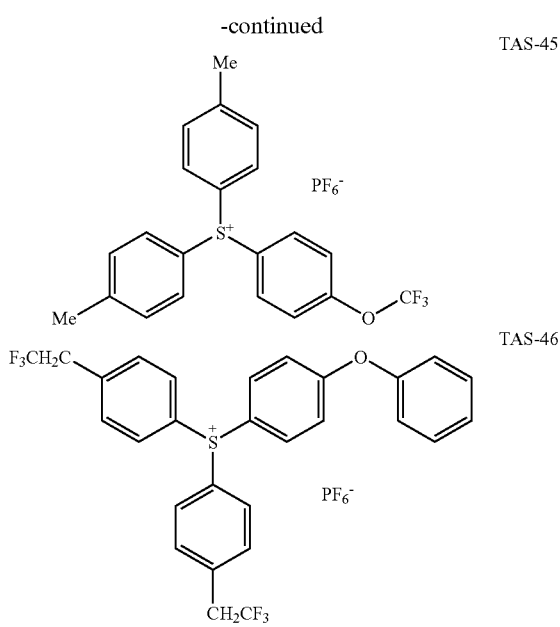

These compounds can be synthesized according to the methods described in Bull. Chem. Soc. Jpn., 42, 312 (1969); J. Polym. Sci., Poly. m. Chem. Ed., 17, 2877 (1979); JP-A 2002-241474; and U.S. Pat. No. 4,404,459. Examples of the synthesis of the exemplified compounds will be described below.

Synthesis of TAS-1

To a one liter flask provided with a calcium chloride cylinder, a thermometer and a mechanical stirrer, 209 g of anisole and 112 g of aluminum chloride were added and mixed while the flask was cooled with ice. 50 g of thionyl chloride was added by dripping over 3 hours, while the interior temperature of the flask was maintained at less than 10° C. with ice, after which the mixture was stirred for one hour, still under ice cooling, and then for three hours at room temperature. The reacted solution was poured into iced water, and 600 ml of ethyl acetate was added for precipitation, after which the aqueous layer was decanted. To the aqueous layer, a solution of 90 g of potassium hexafluorophosphate in 600 ml of purified water was added a little at a time, after which the generated crystals were filtered to obtain 222.7 g of raw crystals. To the raw crystals, 500 ml of methylene chloride was added to dissolve them, after which the solution was refined using a column of activated alumina. After vacuum concentration, 192.2 g of a transparent and viscous liquid was obtained. To the liquid, 600 ml of methanol was added to dissolve the liquid, and the resulted liquid was set aside to cool it to around room temperature, and further stirred for one hour, after which continued cooling with iced water, stirring was continued for two more hours. The crystals were filtered and washed with cold methanol, and then air dried to result in TAS-1. The yield goal was 168.3 g (at a yield of 80%). It was determined to be the specified substance using a $^1$H-NMR and a mass spectrometry.

Synthesis of TAS-2

To a one liter flask provided with a calcium chloride tube, a thermometer and a mechanical stirrer, 25 g of phosphorus oxide and 160 g of methanesulfonic acid were added, and stirred for three hours at an interior temperature at about 80° C. After being set aside to room temperature, 44 g of bis(4-methoxyphenyl)sulfoxide and 43 g of phenyl ether were added and stirred for three hours while cooling the flask with water. To a two liter conical beaker, 31 g of potassium hexafluorophosphate was added to dissolve into one liter of iced water, after which the above reacted solution was added a little at a time while mechanically stirred to obtain a soft white amorphous material. After stopping of stirring, the supernatant liquid was removed by decanting. To the residue, one liter of methylene chloride was added. After water washing, the methylene chloride layer was vacuum concentrated to obtain a crude product, which was refined using an activated alumina column treatment, and the solvent was vacuum concentrated to obtain a light brown, oily component. To the component, 1,000 ml of hexane was added and the resulting crystals were filtered to obtain TAS-2. The yield goal was 72.4 g (the yield being 77%). The crystals were identified as the specified substance using a $^1$H-NMR and a mass spectrometry.

Synthesis of TAS-4

To a one liter flask provided with a calcium chloride tube and a thermometer, 32 g of phosphorus oxide and 150 g of methanesulfonic acid were added, and stirred for three hours at an interior temperature of about 80° C. After being allowed to cool to room temperature, 54 g of bis(4-methoxyphenyl)sulfoxide and 46.8 g of 1-tert-butyl-4-phenoxybenzene were added and stirred for three hours while the flask was cooled with water. To a two liter conical beaker, 42 g of potassium hexafluorophosphate was added and mixed in one liter of iced water, and the above reacted solution was added a little at a time while mechanically stirred to obtain a soft, white amorphous material. After stirring, the supernatant liquid was removed by decanting. To the residue, one liter of methylene chloride was added. After water washing, the methylene chloride layer was vacuum concentrated to obtain a crude product, which was refined using an activated alumina column treatment, and the solvent was vacuum concentrated to obtain a light brown, oily component. To the component, about 100 ml of methanol was added and vacuum concentrated again to completely remove the methylene chloride, after which drying under reduced pressure was conducted using a rotary pump. The amorphous material which foamed to wheat gluten candy-like consistency was beaten to obtain TAS-4. The yield goal was 60.9 g (at a yield of 49%). It was determined to be the specified substance using a $^1$H-NMR and a mass spectrometry.

Synthesis of TAS-6

Added to a one liter flask provided with a calcium chloride tube and a thermometer were, 36 g of phosphorus oxide and 180 g of methanesulfonic acid, after which the contents were stirred and heated for three hours at a temperature of about 80° C. After allowed to cool to room temperature, 60.6 g of bis(4-methoxyphenyl)sulfoxide and 21.3 g of toluene were added. This resulted in a drastic temperature rise due to chemical reaction, so immediate cooling with water was conducted while stirring for another three hours. Added to a two liter conical beaker was, 49 g of potassium hexafluorophosphate and dissolved into one liter of ice cold water, after which the above reacted solution was added bit by bit while mechanically stirred to result in a liver colored, nougat-like amorphous material. After stirring, the supernatant liquid was decanted. Added to the residue, was 800 ml of methylene chloride, followed by a solution of 25 g of hexafluorophosphoric acid/500 ml of purified water, and dispersed for one hour. After draining off the water layer, the remaining methylene chloride layer was vacuum concentrated to obtain the crude product, which was refined using an activated alumina column treatment, after which the solvent was vacuum concentrated to obtain a light brown, oily compound. To the compound, about 100 ml of methanol was added and vacuum concentrated again to completely remove any remaining methylene chloride, after which drying under reduced pressure was conducted using a rotary pump. The amorphous material which foamed to a soft candy-like consistency, was beaten to result in TAS-6. The field goal was 78.5 g (at a yield of 70%). It was confirmed to be the specified substance using a $^1$H-NMR and a mass spectrometry.

Synthesis of TAS-11

Added to a one liter flask provided with a calcium chloride tube and a thermometer, were 32 g of phosphorus oxide and 288 g of methanesulfonic acid, stirred and heated for three hours to a temperature of 80° C.-90° C. After allowed to cool to room temperature, 78.7 g of bis(4-methoxyphenyl)sulfoxide and 60.1 g of 1-methyl-4-phenylsulfanyl-benzene were added and stirred for three hours at ambient temperature. Added to a five liter conical beaker, was 55.2 g of potassium hexafluorophosphate and dissolved into three liters of purified water, after which the above reacted solution was added bit by bit while mechanically stirred to obtain a soft, white amorphous paste. After stirring, the supernatant liquid was decanted. Added to the residue, was 600 ml of methylene chloride, and following that a solution of 25 g of hexafluorophosphoric acid in 500 ml of purified water was added and dispersed for one hour. After siphoning off the water layer, the methylene chloride layer was vacuum concentrated to obtain the crude product, which was refined using an activated alumina column treatment, after which the solvent was vacuum concentrated to obtain a light brown, oily component. Added to the component, was hexane and suspended, after reprecipitation under vigorous mechanically stirring, TAS-11 was obtained, yielding 166.0 g at a yield of 94%. TAS-11 was confirmed to be the specified substance using a $^1$H-NMR and a mass spectrometry.

Synthesis of TAS-13

Added to a one liter flask provided with a calcium chloride tube and a thermometer, were 32 g of phosphorus oxide and 288 g of methanesulfonic acid, stirred and heated for three hours at a temperature of 80° C.-90° C. After allowed to cool to room temperature, 69.1 g of p-toluylsulfoxide and 33 g of anisole were added and stirred for three hours at room temperature. Added to a five liter conical beaker, was 55.2 g of potassium hexafluorophosphate and dissolved into three liter of purified water, and the above reacted solution was added bit by bit while mechanically stirred to obtain a nougat-like amorphous substance. After stirring, the supernatant liquid was decanted. Added to the soft candy-like residue, was 600 ml of methylene chloride, and later a solution of 25 g of hexafluorophosphoric acid in 500 ml of purified water was added and dispersed for one hour. After siphoning off the water layer, activated carbon was added to decolor the methylene chloride layer, after which activated carbon was filtered off, and vacuum concentrated to obtain the crude product, which was refined using an activated alumina column treatment, and then the solvent was vacuum concentrated to obtain 132.6 g of raw crystals. To the crystals, 300 ml of isopropyl alcohol and 10-30 ml of methylene chloride were added, heated and dispersed in a water bath of 60-70° C., and after standing to cool to approximately room temperature, further added was 200 ml of isopropyl alcohol. After stirring for one hour under room temperature, crystals were filtered out to obtain TAS-13, the yield being 123.7 g at a yield of 88%. The crystals were confirmed to be the specified substance using a $^1$H-NMR and a mass spectrometry.

A triarylsulfonium salt (being a polymerization initiator) usable in this invention is preferably contained at a ratio of 0.2-20 weight parts to 100 weight parts of a compound being cationic polymerizable. When the content of the polymerization initiator is less than 0.2 weight parts it is difficult to obtain a hardened material. When more than 20 weight parts are incorporated, none of the desired effects of further hardening are obtained. One or more than two kinds of these triarylsulfonium salts may be employed.

In this invention, to further enhance ejection stability, basic compounds are preferably combined. When the foregoing iodonium salt is employed as a photo acid generator, it is especially effective.

As a basic compound, any well-known appropriate compound may be used, but typical examples include a basic alkali metal compound, a basic alkaline earth metal compound, and basic organic compounds such as amines.

As basic alkali metal compounds, listed are a hydroxide of alkali metals (such as lithium hydroxide, sodium hydroxide and potassium hydroxide), a carbonate of alkali metals (such as lithium carbonate, sodium carbonate and potassium carbonate), and an alcholate of alkali metals (such as sodium methoxide, sodium ethoxide, potassium methoxide and potassium ethoxide).

As basic alkaline earth metal compounds, listed are a hydroxide of alkaline earth metals (such as magnesium hydroxide and calcium hydroxide), a carbonate of an alkaline earth metal (such as magnesium carbonate and calcium carbonate), and an alcholate of an alkaline earth metal (such as magnesium methoxide).

As basic organic compounds, listed are nitrogen containing heterocyclic compounds such as an amine, a quinoline and a quinolizine. Of these, amine is preferable from the viewpoint of compatibility with a photo polymerizable monomer, for example, octylamine, naphthylamine, xylenediamine, dibenzylamine, diphenylamine, dibutylamine, trioctylamine, tetramethylethylenediamine, tetramethyl-1,6-hexamethylenediamine, hexamethylenetetramine, and triethanolamine.

The concentration, when a basic compound exists, is preferably 10-1,000 ppm compared to the total weight of the photo polymerizable monomer, and specifically preferable in the range of 20-500 ppm. These photo polymerizable compounds may be used alone or in combinations of a plurality of them.

In this invention, to enhance further ejection stability, a nonionic surface active agent is preferably used in combination with the triarylsulfonium salt.

As a nonionic surface active agent usable in this invention, there is no specific limitation, and exemplified is such as a polyoxyethylene-polyoxypropylene condensate, a polyoxyethylene laury ether, a secondary alcohol ethoxylate, a primary alcohol ethoxylate, a nonylphenol ethoxylate, an octylphenol ethoxylate, an oleyl alcohol ethoxylate, a lauryl alcohol ethoxylate, polyethylene glycol, polyoxyethylene glycol oleate, a sorbitan stearyl ester, a sorbitan oleyl ester, a polyoxyethylene sorbitan oleyl ester, a 2-hydroxyethyl methacrylate, a 4-hydroxybutyl acrylate, or an acrylic resin copolymerized of hydroxyl group containing unsaturated monomers such as a polyethylene glycol mono-methyl ether.

Further, as samples, listed are alcohols such as isopropyl alcohol, n-butyl alcohol, propylene glycol mono-methyl ether, and propylene glycol mono-butyl ether, or glycol ethers. Nonionic surface active agents may be used alone or a mixture of more than two kinds.

In this invention, a specifically preferable nonionic surface active agent is a fluorochemical surface active agent which has a perfluoroalkyl group in the molecule. Examples of a fluorochemical surface active agent which has a perfluoroalkyl group in the molecule usable in this invention include a perfluoroalkyl ethylene oxide addition product, a perfluoroalkylamine oxide, and a perfluoroalkyl containing oligomer, and specifically, for example, SURFLON S-141, SURFLON S-145, SURFLON S-381, SURFLON S-383, SURFLON S-393, SURFLON SC-101, SURFLON SC-105, SURFLON KH-40 ans SURFLON SA-100 (all being products of SEIMI CHEMICAL Co., Ltd.), and MEGAFACE F-171, MEGAFACE F-172, MEGAFACE F-173, MEGAFACE F-177, MEGAFACE F-178A, MEGAFACE F-178, MEGAFACE F-183, MEGAFACE F-184, MEGAFACE F-815, MEGAFACE F-470, and MEGAFACE F-471 (all being products of DAINIPPON INK AND CHEMICALS, INCORPORATED). [reference literature; Chemical Products 13,700, pp. 1,239-1,242, The Chemical Daily, Co., Ltd. (2000)]. In the ink of this invention, the fluorochemical surface active agents which have a perfluoroalkyl group in the molecule may be used alone or in combinations more than two kinds.

In the ink of this invention, the desired characteristic is to contain a compound having an oxetane ring as a photo polymerizable compound.

The oxetane compounds usable in the present invention refer to compounds having an oxetane ring. It is possible to employ any appropriate oxetane compound known in the art, such as those introduced in JP-A Nos. 2001-220526 and 2001-310937. Further, in this invention, from the viewpoint of enhancement of better curability and ejection stability, it is preferable to contain a compound having at least one oxilane group.

As a photo polymerizable monomer, a cationic photo polymerizable monomer, well known in the art, may be employed. For example, listed are epoxy compounds, vinyl ether compounds, and oxetane compounds which are described in JP-A Nos. 6-9714, 2001-31892, 2001-40068, 2001-55507, 2001-310938, 2001-310937, and 2001-220526.

Epoxy compounds include the following aromatic epoxides, alicyclic epoxides and aliphatic epoxides. Preferred aromatic epoxides include di- or polyglycidyl ethers prepared by allowing polyhydric phenols having at least one aromatic nucleus or alkylene oxide addition products thereof to react with epichlorohydrine. For example, listed are di- or polyglycidyl ethers of bisphenol A or alkylene oxide addition products thereof, di- or polyglycidyl ethers of hydrogenated bisphenol A or alkylene oxide addition products thereof, or novolak type epoxy resins. Herein, listed as alkylene oxides are ethylene oxides and propylene oxides.

Alicyclic epoxides are preferably compounds containing cyclohexene oxide or cyclopentene oxide which are prepared by epoxidizing compounds having at least one cycloalkene such as a cyclohexene or cyclopentene, employing suitable oxidizing agents such as hydrogen peroxide or peracids.

Preferred aliphatic epoxides include di- or polyglycidyl ethers of aliphatic polyhydric alcohols or alkylene oxide addition products thereof. Representative examples include diglycidyl ethers of alkylene glycol, such as diglycidyl ether of ethylene glycol, diglycidyl ether of propylene glycol, or diglycidyl ether of 1,6-hexnediol, and diglycidyl ethers of polyalkylene glycol, such as polyglycidyl ether of polyhydric alcohols such as di- or triglycidyl ethers of glycerin or alkylene oxide addition products thereof or diglycidyl ether of polyethylene glycol or alkylene oxide addition products thereof, as well as diglycidyl ether of polypropylene glycol or alkylene oxide addition products thereof. Herein, listed as preferable alkylene oxides are ethylene oxide and propylene oxide.

Of these epoxides, when considering curing rate, aromatic epoxides as well as alicyclic epoxides are preferred, of which alicyclic epoxides are specifically preferred. In the present invention, the foregoing epoxides may be employed individually or compatible combinations of at least two types.

In this invention, alicyclic epoxides are preferably compounds represented by foregoing Formulas (A) and (I)-(VI). In Formulas (A) and (I)-(VI), $R_{100}$, $R_{101}$, $R_{103}$, $R_{104}$, $R_{105}$ and $R_{106}$ are each substituent groups, which include, for example, a halogen atom (such as a chlorine atom, a bromine atom or a fluorine atom), an alkyl group of 1-6 carbon atoms (such as a methyl group, ethyl group, propyle group, isopropyle group and a butyl group), an alkoxyl group of 1-6 carbon atoms (such as a methoxy group, ethoxy group, n-propoxy group, iso-propoxy group, n-butoxy group and a tert-butoxy group), an acyl group (such as an acetyl group, propionyl group and a trifluoroacetyl group), an acyloxy group (such as an acetoxy group, propionyloxy group and a trifluoroacetoxy group), and an alkoxycarbonyl group (such as a methoxy carbonyl group, ethoxycarbonyl group and tert-butoxycarbonyl group). Of the foregoing substituent groups, preferred is an alkyl group, an alkoxyl group, or an alkoxycarbonyl group.

In foregoing Formulas (A) and (I)-(VI), m0, m1, m2, m3, m4 and m6 are each an integer of 0-2, and preferably 0 or 1, while m5 is 1 or 2.

In foregoing Formula (A), $L_0$ is a r0+1 valent combining group of 1-15 carbon atoms, in which main chain an oxygen atom or a sulfur atom may be contained, or also a single bond. In foregoing Formula (I), $L_1$ is a r1+1 valent combining group of 1-15 carbon atoms, in which main chain an oxygen atom or a sulfur atom may be contained, or also a single bond. In foregoing Formula (II), $L_2$ is a r2+1 valent combining group of 1-15 carbon atoms, in which main chain an oxygen atom or a sulfur atom may be contained, or also a single bond. In foregoing Formulas (III) and (IV), $L_3$ and $L_4$ are each divalent combining group of 8 carbon atoms, in which main chain an oxygen atom or a sulfur atom may be contained, or also a single bond.

As examples of the above divalent combining groups, in which main chain an oxygen atom or a sulfur atom may be contained, listed are the following groups, as well as groups which are completed by the plural combinations of an —O— group, an —S— group, a —CO— group, or a —CS— group, with the following groups.

A methylene group: [—CH$_2$—]
An ethylidene group: [>CHCH$_3$]
An isopropilidene group: [>C(CH$_3$)$_2$]
A 1,2-ethylene group: [—CH$_2$CH$_2$—]
A 1,2-propilene group: [—CH(CH$_3$)CH$_2$—]
A 1,3-propanediyl group: [—CH$_2$CH$_2$CH$_2$—]
A 2,2-dimethyl-1,3-propanediyl group: [—CH$_2$C(CH$_3$)$_2$CH$_2$—]
A 2,2-dimethoxy-1,3-propanediyl group: [—CH$_2$C(OCH$_3$)$_2$CH$_2$—]
A 2,2-dimethoxymethyl-1,3-propanediyl group: [—CH$_2$C(CH$_2$OCH$_3$)$_2$CH$_2$—]
A 1-methyl-1,3-propanediyl group: [—CH(CH$_3$)CH$_2$CH$_2$—]
A 1,4-buthanediyl group: [—CH$_2$CH$_2$CH$_2$CH$_2$—]
A 1,5-penthanediyl group: [—CH$_2$CH$_2$CH$_2$CH$_2$CH$_2$—]
An oxydiethylene group: [CH$_2$CH$_2$OCH$_2$CH$_2$—]
A thiodiethylene group: [—CH$_2$CH$_2$SCH$_2$CH$_2$—]
A 3-oxothiodiethylene group: [—CH$_2$CH$_2$SOCH$_2$CH$_2$—]
A 3,3-dioxothiodiethylene group: [—CH$_2$CH$_2$SO$_2$CH$_2$CH$_2$—]
A 1,4-dimethyl-3-oxa-1,5-pentanediyl group: [—CH(CH$_3$)CH$_2$OCH(CH$_3$)CH$_2$—]

A 3-oxopentanediyl group: [—CH$_2$CH$_2$COCH$_2$CH$_2$—]
A 1,5-dioxo-3-oxapentanediyl group: [—COCH$_2$OCH$_2$CO—]
A 4-oxa-1,7-heptanediyl group: [—CH$_2$CH$_2$CH$_2$OCH$_2$CH$_2$CH$_2$—]
A 3,6-dioxa-1,8-octanediyl group: [—CH$_2$CH$_2$OCH$_2$CH$_2$OCH$_2$CH$_2$—]
A 1,4,7-trimethyl-3,6-dioxa-1,8-octanediyl group: [—CH(CH$_3$)CH$_2$OCH(CH$_3$)CH$_2$OCH(CH$_3$)CH$_2$—]
A 5,5-dimethyl-3,7-dioxa-1,9-nonanediyl group: [—CH$_2$CH$_2$OCH$_2$C(CH$_3$)$_2$CH$_2$OCH$_2$CH$_2$—]
A 5,5-dimethoxy-3,7-dioxa-1,9-nonanediyl group: [—CH$_2$CH$_2$OCH$_2$C(CH$_3$)$_2$CH$_2$OCH$_2$CH$_2$—]
A 5,5-dimethoxymethyl-3,7-dioxa-1,9-nonanediyl group: [—CH$_2$CH$_2$OCH$_2$C(CH$_2$OCH$_3$)$_2$CH$_2$OCH$_2$CH$_2$—]
A 4,7-dioxo-3,8-dioxa-1,10-decanediyl group: [—CH$_2$CH$_2$O—COCH$_2$CH$_2$CO—OCH$_2$CH$_2$—]
A 3,8-dioxo-4,7-dioxa-1,10-decanediyl group: [—CH$_2$CH$_2$CO—OCH$_2$CH$_2$O—COCH$_2$CH$_2$—]
A 1,3-cyclopentanediyl group: [-1,3-C$_5$H$_8$—]
A 1,2-cyclohexanediyl group: [-1,2-C$_6$H$_{10}$—]
A 1,3-cyclohexanediyl group: [-1,3-C$_6$H$_{10}$—]
A 1,4-cyclohexanediyl group: [-1,4-C$_6$H$_{10}$—]
A 2,5-tetrahydrofrandiyl group: [2,5-C$_4$H$_6$O—]
A p-phenylene group: [-p-C$_6$H$_4$—]
A m-phenylene group: [-m-C$_6$H$_4$—]
A α,α'-o-xylylene group: [-o-CH$_2$—C$_6$H$_4$—CH$_2$—]
A α,α'-m-xylylene group: [-m-CH$_2$—C$_6$H$_4$—CH$_2$—]
A α,α'-p-xylylene group: [-p-CH$_2$—C$_6$H$_4$—CH$_2$—]
A furan-2,5-diyl-bismethylene group: [2,5-CH$_2$—C$_4$H$_2$S—CH$_2$—]
A thiophene-2,5-diyl-bismethylene group: [2,5-CH$_2$—C$_4$H$_2$S—CH$_2$—]
An isopropylidenebis-p-phenylene group: [-p-C$_6$H$_4$—C(CH$_3$)$_2$-p-C$_6$H$_4$—]

As combining groups of tri or higher valent groups, listed are groups which are completed by removing required numbers of hydrogen atoms from optional positions of the above divalent combining groups, and groups which are completed by plural combinations of an —O— group, an —S— group, a —CO— group, or a —CS— group, with the above groups of higher than tri-valent combining groups. L$_0$, L$_1$, L$_2$, L$_3$ and L$_4$ may each have substituent groups. Examples of substituent groups include a halogen atom (such as a chlorine atom, bromine atom or a fluorine atom), an alkyl group of 1-6 carbon atoms (such as a methyl group, ethyl group, propyle group, isopropyle group and a butyl group), an alkoxyl group of 1-6 carbon atoms (such as a methoxy group, ethoxy group, n-propoxy group, iso-propoxy group, n-butoxy group and a tert-butoxy group), an acyl group (such as an acetyl group, propionyl group and a trifluoroacetyl group), an acyloxy group (such as an acetoxy group, propionyloxy group and a trifluoroacetoxy group), as well as an alkoxycarbonyl group (such as a methoxy carbonyl group, ethoxycarbonyl group and a tert-butoxycarbonyl group). Of the foregoing substituent groups, preferred is an alkyl group, an alkoxyl group, or an alkoxycarbonyl group.

L$_0$, L$_1$ and L$_2$ are each preferably divalent combining groups of 1-8 carbon atoms, the main chain of which may contain an oxygen atom. While, L$_0$, L$_1$, L$_2$, L$_3$ and L$_4$ are each more preferably divalent combining groups of 1-5 carbon atoms, the main chain of which is composed of carbon atoms and hydrogen atoms.

p1 and q1 are each 0 or 1, and p1+q1 is preferably more than one. p2 and q2 are each 0 or 1, and are each preferably 1. p3 and p4 are each 0 or 1.

Specific examples of preferable alicyclic epoxy compounds will now be described. However, the present invention is not limited thereto.

EP-1
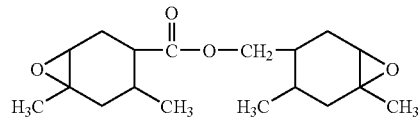

EP-2
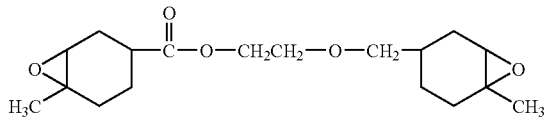

EP-3
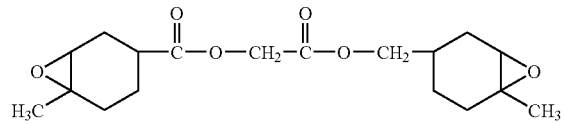

EP-4
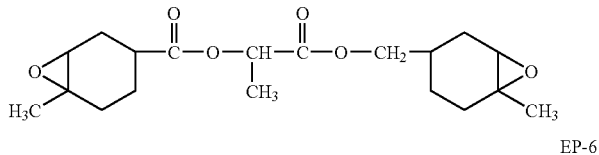

EP-5
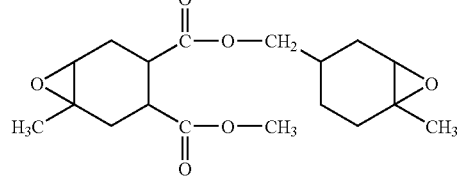

EP-6
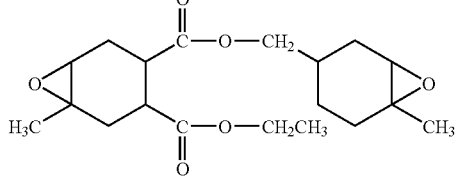

EP-7
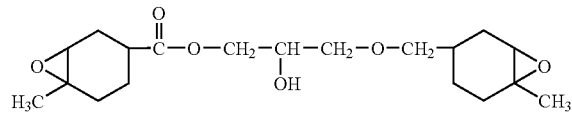

EP-8
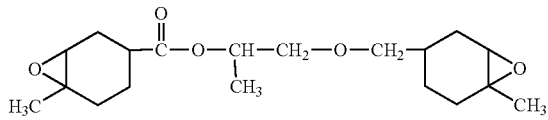

-continued
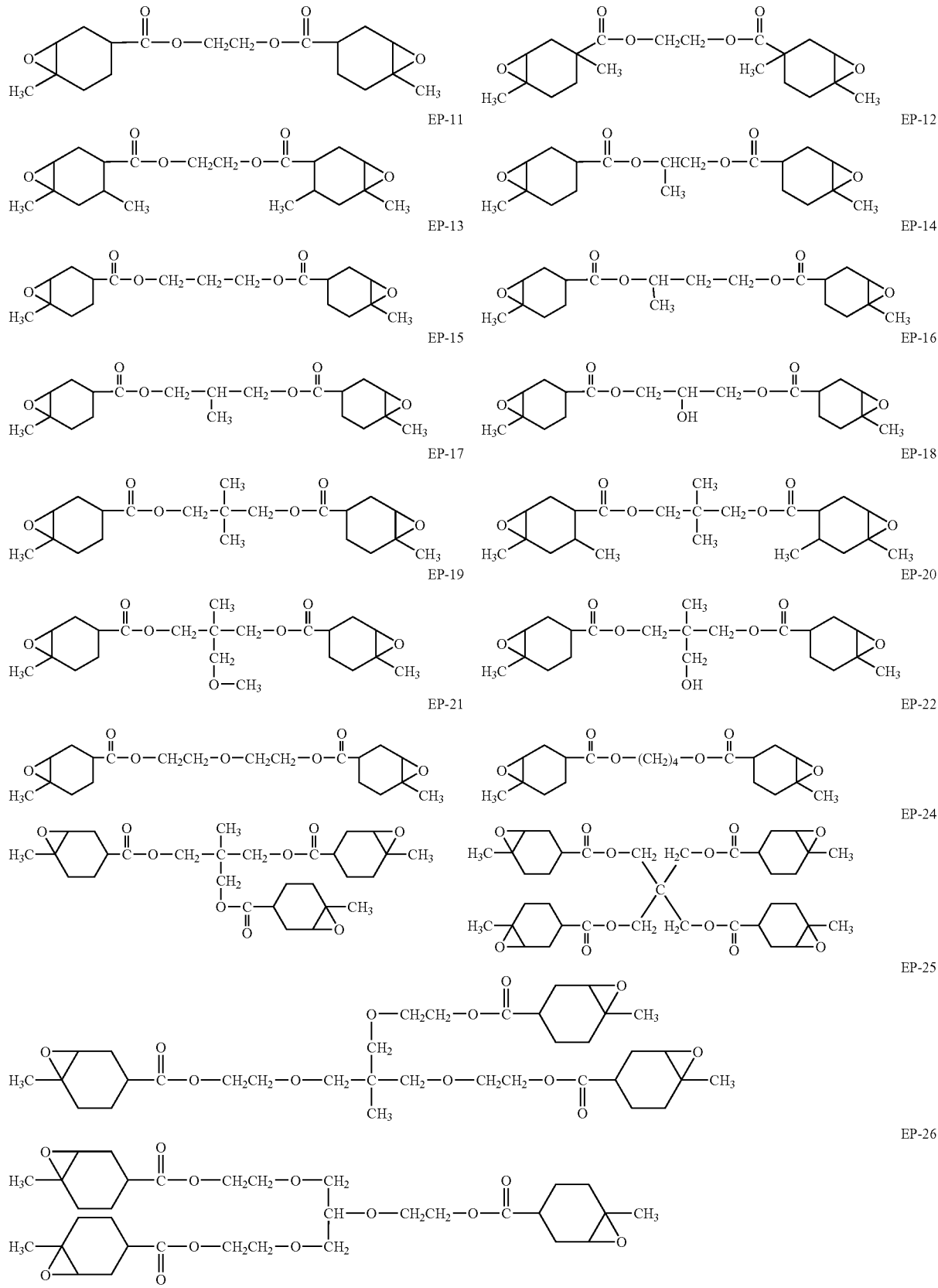

-continued
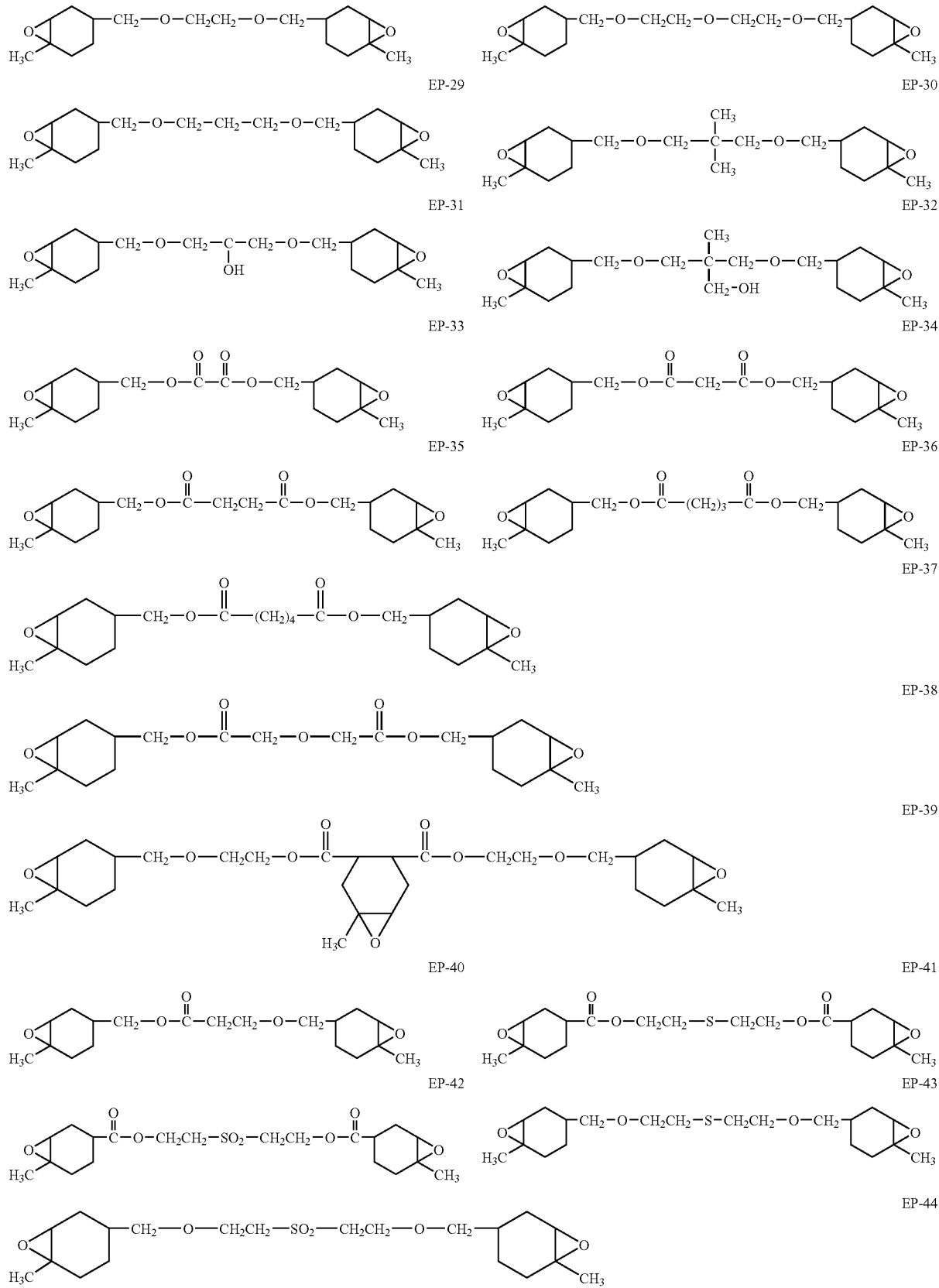

-continued
EP-45
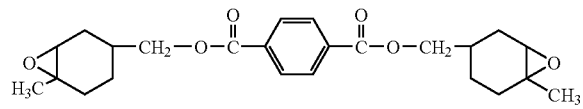
EP-46
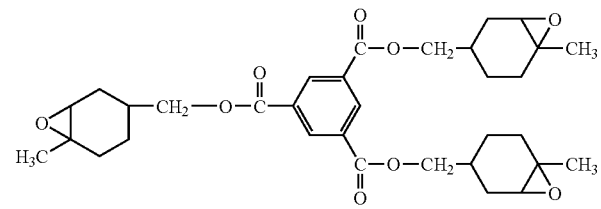
EP-47
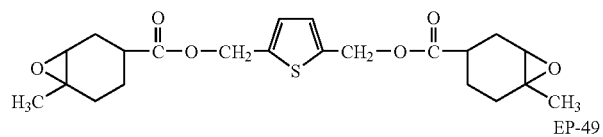
EP-48
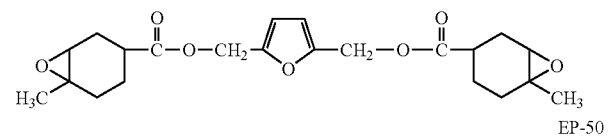
EP-49
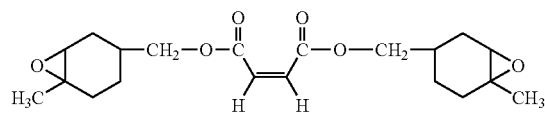
EP-50
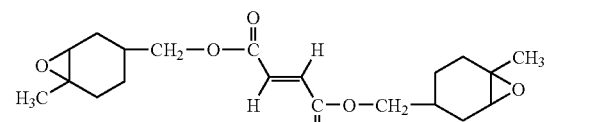
EP-51
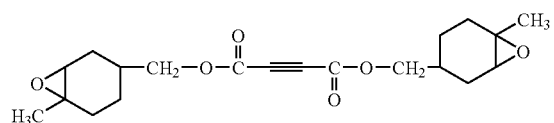
EP-52
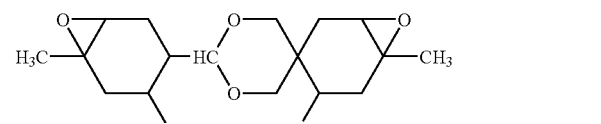
EP-53
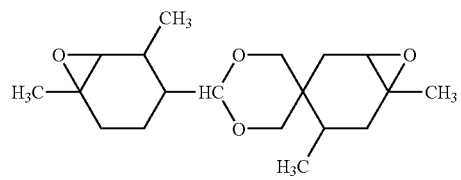
EP-54
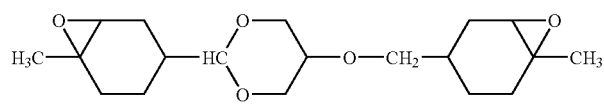
EP-55
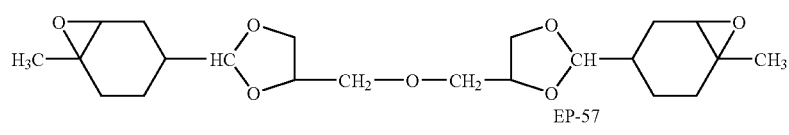
EP-56
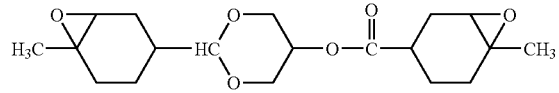
EP-57
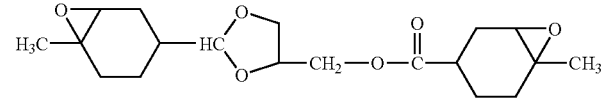
EP-58
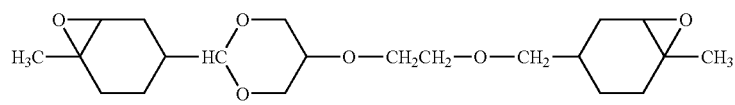
EP-59
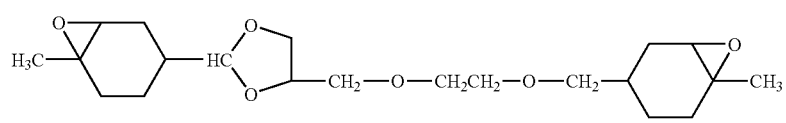
EP-60
EP-61
EP-62

-continued

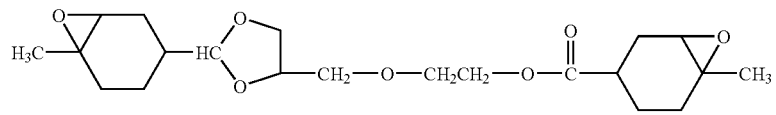
EP-63

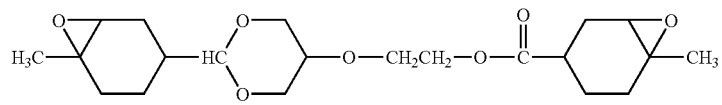
EP-64

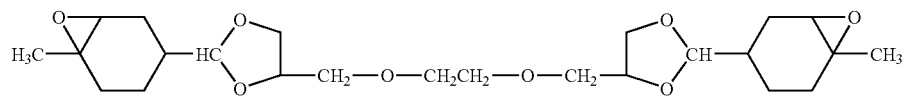
EP-65

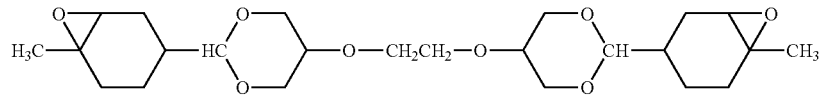
EP-66

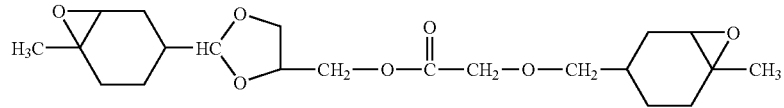
EP-67

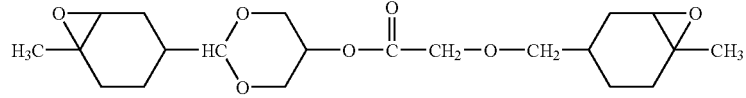
EP-68

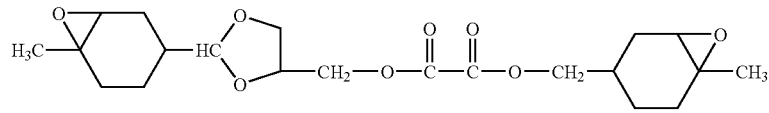
EP-69

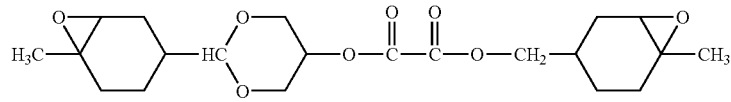
EP-70

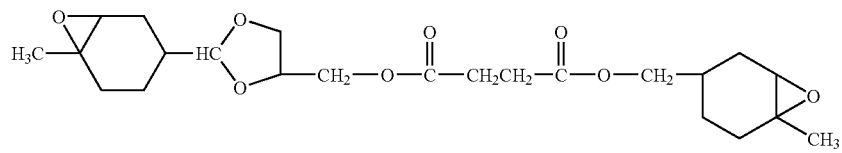
EP-71

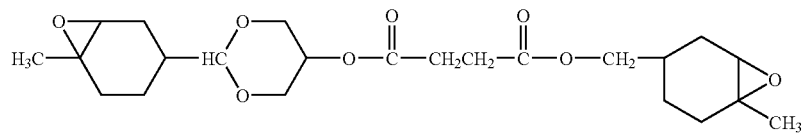
EP-72

In the above alicyclic epoxy compounds of this invention, the numerical value of the molecular weight divided by the total numbers of epoxy groups in the molecule is preferably in the range of 160-300.

Synthesis of alicyclic epoxy compounds represented by foregoing Formulas (A) and (I)-(VI) of this invention may be performed based on the methods described in the following patents listed below.

A: U.S. Pat. No. 2,745,847
B: U.S. Pat. No. 2,750,395
C: U.S. Pat. No. 2,853,498
D: U.S. Pat. No. 2,853,499
E: U.S. Pat. No. 2,863,881

The synthesis examples of the above exemplified compounds of the methods described in the above patents will be described below, but the present invention is not limited to these examples.

SYNTHESIS EXAMPLE 1

Synthesis of Exemplified Compound EP-9: Ethyleneglycol-bis-(4-methyl-3,4-epoxy-cyclohexanecarboxylate)

Synthesis of Methyl-(4-methyl-3-cyclohexenecarboxylate)

According to the well known Diels-Alder Reaction, using isoprene and methyl methacrylate as raw materials, methyl-(4-methyl-3-cyclohexenecarboxylate) was synthesized. The reaction was conducted under the conditions according to those described in the literary documents of J. Organomet. Chem., 285, 1985, 333-342; J. Phys. Chem., 95, 5, 1992, 2293-2297; and Acta. Chem. Scand., 47, 6, 1993, 581-591; or U.S. Pat. No. 1,944,731. A high yield of the objective compound was obtained.

Synthesis of Ethyleneglycol-bis-(4-methyl-3-cyclohexenecarboxylate)

Added to 340 g (2 mol) of methyl-(4-methyl-3-cyclohexenecarboxylate) and 62 g of ethylene glycol, was 1 g of toluenesulfonic acid monohydrate, for a reaction over 8 hours at 80-90° C. After the reacted solution was washed with sodium bicarbonate water, distillation under reduced pressure was conducted to obtain the objective compound at a yield of 92%.

Synthesis of Exemplified Compound EP-9

Fed into a two liter, three necked flask was 306 g of ethyleneglycol-bis-(4-methyl-3-cyclohexenecarboxylate), after which 770 g of an acetone solution, having a 25 weight % content of peracetic acid [being 192 g of peracetic acid (2.5 mol)], was dripped over 4 hours at a constant temperature of 35-40° C. After dripping was finished, the reaction was continued for further 4 hours under the same temperature range. After the reacted solution was stored at −11° C. overnight, it was confirmed by a check for peracetic acid residue that more than 98% of the theoretical quantity had reacted. Subsequently, the reacted solution was diluted with one liter of toluene, and under reduced pressure using a water-jet aspirator, the solution was heated to 50° C. to remove any low boiling point content until no distillant was observed. The residual reaction composition was distilled under reduced pressure to obtain the objective EP-9 exemplified compound, at a yield of 78%. The structure of exemplified compound EP-9 was confirmed using NMR and MASS analysis, being 1H NMR (CDCl3) δ (ppm): 1.31 (s, 6H, $CH_3$—), 1.45-2.50 (m, 14H, a cyclohexane ring), 3.10 (m, 2H, an epoxy ring), 4.10 (s, 4H, —$CH_2$—O—).

SYNTHESIS EXAMPLE 2

Synthesis of Exemplified Compound EP-12: Propane-1,2-diol-bis-(4-methyl-3,4-epoxy-cyclohexanecarboxylate)

Synthesis of Propane-1,2-diol-bis-(4-methyl-3-cyclohexenecarboxylate)

Added to 340 g (being 2 mol) of methyl-(4-methyl-3-cyclohexenecarboxylate) and 76 g (being 1 mol) of propane-1,2-diol, was 1 g of toluensulfonic acid monohydrate, reacted for 8 hours at 80-90° C. After the reacted solution was washed with sodium bicarbonate water, distillation under reduced pressure was conducted to obtain the objective compound, at a yield of 90%.

Synthesis of Exemplified Compound EP-12

Fed into a two liter, three necked flask was 320 g of propane-1,2-diol-bis-(4-methyl-3-cyclohexenecarboxylate), after which 770 g of an acetone solution having a 25 weight % content of peracetic acid [being 192 g of peracetic acid (2.5 mol)] was dripped over 4 hours at a constant temperature of 35-40° C. After dripping was finished, the reaction was continued for further 4 hours under the same temperature range. After the reacted solution was stored at −11° C. overnight, it was confirmed by a check for peracetic acid residue that more than 98% of the theoretical quantity had reacted. Subsequently, the reacted solution was diluted with one liter of toluene, and under reduced pressure using a water-jet aspirator, the solution was heated to 50° C. to remove any low boiling point content until no distillates were observed. The residual reaction composition was distilled under reduced pressure to obtain the objective EP-12 exemplified compound, at a yield of 75%. The structure of exemplified compound EP-12 was confirmed using NMR and MASS analysis, being 1H NMR (CDCl3) δ (ppm): 1.23 (s, 3H, $CH_3$—), 1.31 (s, 6H, $CH_3$—), 1.45-2.50 (m, 14H, a cyclohexane ring), 3.15 (m, 2H, an epoxy ring), 4.03 (m, 1H, —O—$CH_2$—), 4.18 (m, 1H, —O—$CH_2$—), 5.15 (m, 1H, >CH—O—).

SYNTHESIS EXAMPLE 3

Synthesis of Exemplified Compound EP-17: 2,2-Dimethyl-propane-1,3-diol-bis-(4-methyl-3,4-epoxy-cyclohexanecarboxylate)

Synthesis of 2,2-Dimethyl-propane-1,3-diol-bis-(4-methyl-3-cyclohexenecarboxylate)

Added to 340 g (being 2 mol) of 2,2-dimethyl-propane-1,3-diol-bis-(4-methyl-3-cyclohexenecarboxylate) and 104 g (being 1 mol) of 2,2-dimethyl-propane-1,3-diol, was 1 g of toluenesulfonic acid monohydrate and reacted for 12 hours at 80-90° C. After the reacted solution was washed with sodium bicarbonate water, distillation under reduced pressure was conducted to obtain the objective compound, at a yield of 86%.

Synthesis of Exemplified Compound EP-17

Fed into a two liter, three necked flask was 348 g of 2,2-dimethyl-propane-1,3-diol-bis-(4-methyl-3-cyclohexenecarboxylate), after which 770 g of an acetone solution, having a 25 weight % content of peracetic acid [being 192 g (2.5 mol) of peracetic acid], was dripped over 4 hours at a constant temperature of 40° C. After dripping was finished, the reaction was continued for further 4 hours under the same temperature range. After the reacted solution was stored at −11° C. overnight, it was confirmed by a check for peracetic acid residue that more than 98% of the theoretical quantity had reacted. Subsequently, the reacted solution was diluted with one liter of toluene, and under reduced pressure using a water-jet aspirator, the solution was heated to 50° C. to remove any low boiling point content until no distillates were observed. The residual reaction composition was distilled under reduced pressure to obtain the objective EP-17 exemplified compound, at a yield of 70%. The structure of exemplified compound EP-17 was confirmed using NMR and MASS analysis, being 1H NMR (CDCl3) δ (ppm): 0.96 (s, 6H; $CH_3$—), 1.31 (s, 6H, $CH_3$—), 1.45-2.50 (m, 14H, a cyclohexane ring), 3.00 (m, 2H, an epoxy ring), 3.87 (s, 4H, —O—$CH_2$—).

SYNTHESIS EXAMPLE 4

Synthesis of Exemplified Compound EP-31: 1,3-Bis-(4-methyl-3,4-epoxy-cyclohexylmethyloxy)-2-propanol Synthesis of 4-Methyl-3-cyclohexenylmethanol According to the well known Diels-Alder Reaction, using isoprene and acrolein as raw materials, 4-methyl-3-cyclohexenyl aldehyde was synthesized. The reaction was conducted under the conditions described in the literary documents of J. Amer, Chem. Soc., 119, 15, 1997, 3507-3512; and Tetrahedron Lett., 40, 32, 1999, 5817-5822. Subsequently, the compound was reduced to obtain 4-methyl-3-cyclohexenyl-methanol at a high yield.

Synthesis of 1,2-Bis-(4-methyl-3-cyclohexenylmethyloxy)-2-propanol

Added to 284 g (being 2 mol) of 4-methyl-3-cyclohexenyl-methanol and one liter acetone solution containing 92 g (being 1 mol) of epichlorohydrin, was 305 g (being 2.2 mol) of potassium carbonate, and reacted for 8 hours at 50° C. The precipitated salt was removed by filtration, and after the reacted solution was condensed under reduced pressure, the residual raw product was distilled under reduced pressure to obtain the objective compound, at a yield of 90%.

Synthesis of Exemplified Compound EP-31

Fed into a two liter, three necked flask was 308 g (being 1 mol) of 1,2-bis-(4-methyl-3-cyclohexenylmethyloxy)-2-propanol, after which 770 g of an acetone solution, having a 25 weight % content of peracetic acid [being 192 g (2.5 mol) of peracetic acid], was dripped over 4 hours at a constant temperature of 35-40° C. After dripping, the reaction was continued for further 4 hours under the same temperature range. After the reacted solution was stored at −11° C. overnight, it was confirmed by a check for peracetic acid residue that more than 98% of the theoretical quantity had reacted. Subsequently, the reacted solution was diluted with one liter of toluene, and under reduced pressure using a water-jet aspirator, the solution was heated to 50° C. to remove any low boiling point content until no distillates were observed. The residual reaction composition was distilled under reduced pressure to obtain the objective EP-31 exemplified compound, at a yield of 83%.

The structure of Exemplified Compound EP-31 was confirmed using NMR and MASS analysis, confirmed to be 1H NMR (CDCl3) δ (ppm): 1.31 (s, 6H, $CH_3$—), 1.4-2.0 (m, 14H, a cyclohexane ring), 2.7 (s, 1H, —OH), 3.10 (m, 2H, an epoxy ring), 3.45 (d, 4H, —$CH_2$—O—), 3.50 (m, 4H, —$CH_2$—O—), 3.92 (m, 1H, >CH—).

SYNTHESIS EXAMPLE 5

Synthesis of Exemplified Compound EP-35: Bis-(4-methyl-3,4-epoxy-cyclohexylmethyl)oxalate Synthesis of Bis-(4-methyl-3-cyclohexenylmethyl)succinate Added to 284 g (being 2 mol) of 4-methyl-3-cyclohexenyl-methanol and one liter toluene solution containing 10 g (being 1 mol) of succinic acid anhydride, was 5 g of toluene-sulfonic acid monohydrate, and allowed to react for 8 hours at 110-120° C., while any generated water was removed using a water separating apparatus. After the reacted solution was washed with sodium bicarbonate water, distillation under reduced pressure was conducted to remove any toluene. The residual crude product was distilled under reduced pressure to obtain the objective compound. The yield was 90%.

Synthesis of Exemplified Compound EP-35

Fed into a two liter, three necked flask was 335 g (being 1 mol) of bis-(4-methyl-3-cyclohexenylmethyl) succininate, after which 770 g of an acetone solution, having a 25 weight % content of peracetic acid [being 192 g (2.5 mol) of peracetic acid], was dripped over 4 hours at a constant temperature of 35-40° C. After dripping was finished, the reaction was continued for further 4 hours under the same temperature range. After the reacted solution was stored at −11° C. overnight, it was confirmed by a check for peracetic acid residue that more than 98% of the theoretical quantity had reacted. Subsequently, the reacted solution was diluted with one liter of toluene, and under reduced pressure using a water-jet aspirator, the solution was heated to 50° C. to remove any low boiling point content until no distillates were observed. The residual reaction composition was distilled under reduced pressure to obtain the objective EP-35 exemplified compound, at a yield of 75%.

The structure of Exemplified Compound EP-35 was confirmed using NMR and MASS analysis, being 1H NMR (CDCl3) δ (ppm): 1.31 (s, 6H, $CH_3$—), 1.4-2.0 (m, 14H, a cyclohexane ring), 3.10 (m, 2H, an epoxy ring), 3.62 (s, 4H, —$CH_2$—CO—), 4.05 (d, 4H, —$CH_2$—O—).

The other alicyclic epoxy compounds of this invention, which were listed above, can be similarly synthesized at a high yield.

Further, in this invention, from the viewpoint of operator safety, such as the AMES test and causing sensitivity to humans, the epoxy compound having an oxirane group is specifically preferable to be an epoxidized fatty acid ester or an epoxidized fatty acid glyceride. Any epoxidized fatty acid ester and an epoxidized fatty acid glyceride, in cases when an epoxy group is introduced into a fatty acid ester or a fatty acid glyceride, may be used without particular limitation.

As epoxidized fatty acid esters, the compounds produced by epoxidation of oleic acid ester such as methyl epoxystearate, butyl epoxystearate, and octyl epoxystearate, may be used. Further, epoxidized fatty acid glycerides are compounds produced by epoxidation of soybean oil, linseed oil or castor oil, such that epoxidized soybean oil, epoxidized linseed oil and epoxidized castor oil may be used. Further, in this invention, also usable may be well known vinyl ether compounds.

Examples of vinyl ether compounds include di- or trivinyl ether compounds such as ethylene glycol divinyl ether, diethylene glycol divinyl ether, triethylene glycol divinyl ether, propylene glycol divinyl ether, dipropylene glycol divinyl ether, butanediol divinyl ether, hexanediol divinyl ether, cyclohexanedimethanol divinyl ether, trimethylolpropane trivinyl ether, as well as monovinyl ether compounds such as ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexanedimethanol monovinyl ether, n-propyl vinyl ether, isopropyl vinyl ether, isopropenyl ether-o-propylene carbonate, dodecyl vinyl ether, diethylene glycol monovinyl ether, and octadecyl vinyl ether.

Of these vinyl ether compounds, when considering curability, adhesion property, and surface hardness, di- or trivinyl ether compounds are preferred, of which divinyl ether compounds are particularly preferred. In the present invention, the aforesaid vinyl ether compounds may be employed individually or in compatible combinations of at least two types.

The added amount of the aforesaid photopolymerizable monomers is preferably adjusted in such a manner that the compound having at least one type of the oxetane ring is in an amount of 60-95 percent by weight, the compound having at least one type of the oxirane group is in an amount of 5-40 weight %, and at least one type of the vinyl ether compound is in an amount of 0-40 weight %.

The oxetane ring containing compounds represented by Formula (E) of this invention will be described below.

In Formula (E), $R_1$-$R_6$ are each a hydrogen atom or a substituent group, and $R_1$-$R_6$ are not to be a hydrogen atom at the same time. Examples of the compounds containing one oxetane ring in the molecule include the compounds represented by following Formulas (2)-(5).

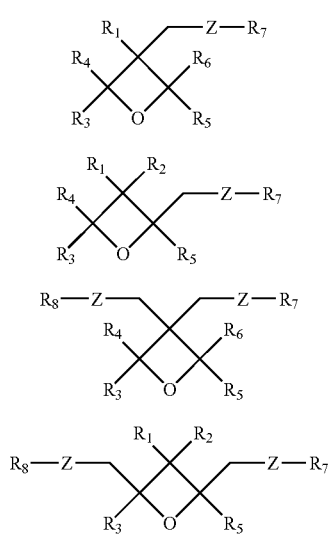

In above Formulas (2)-(5), each Z is independent and an oxygen atom, a sulfur atom or a divalent hydrocarbon group in the main chain, which may contain an oxygen atom or a sulfur atom; $R_1$-$R_6$ are each an alkyl group of 1-6 carbon atoms such as a hydrogen atom, fluorine atom, a methyl group, ethyl group, propyl group or a butyl group, a fluoroalkyl group of 1-6 carbon atoms, an allyl group, an aryl group, a furyl group or an ethynyl group; $R_7$ and $R_8$ are each an alkyl group of 1-6 carbon atoms such as a methyl group, ethyl group, propyl group or a butyl group, an alkenyl group of 1-6 carbon atoms such as a 1-propenyl group, 2-propenyl group, 2-methyl-1-propenyl group, 2-methyl-2-propenyl group, 1-butenyl group, 2-butenyl group or a 3-butenyl group; an aryl group such as a phenyl group, benzyl group, fluorobenzyl group, methoxybenzyl group, or a phenoxyethyl group; an alkylcarbonyl group of 1-6 carbon atoms such as a propylcarbonyl group, butylcarbonyl group, or a pentylcarbonyl group; an alkoxycarbonyl group of 1-6 carbon atoms such as an ethoxycarbonyl group, propoxycarbonyl group, or a buthoxycarbonyl group; an alkoxycarbamoyl group such as an ethoxycarbamoyl group, propylcarbamoyl group, or a butyl-pentylcarbamoyl group.

Preferred as oxetane incorporating compounds usable in this invention, in foregoing Formulas (2)-(5), are compounds of $R_1$ being a lower alkyl group, especially an ethyl group; $R_7$ and $R_8$ are a propyl group, a butyl group, a phenyl group or a benzyl group; Z is a hydrocarbon group containing no oxygen nor sulfur atom. Further, $R_3$-$R_6$ are not a hydrogen atom at the same time.

Listed as compounds containing more than two oxetane rings in the molecule, are the compounds represented by following Formulas (6), (7) and (13).

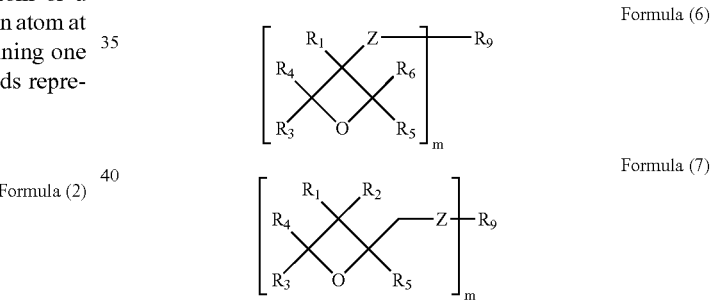

In above Formulas (6) and (7), "m" is 2, 3 or 4; Z is each independently an oxygen atom, a sulfur atom or a divalent hydrocarbon group which may contain an oxygen atom or a sulfur atom; $R_1$ is an alkyl group of 1-6 carbon atoms such as a hydrogen atom, fluorine atom, a methyl group, ethyl group, propyl group or a butyl group, a phenyl group, a fluoroalkyl group of 1-6 carbon atoms, an allyl group, an aryl group, or a furyl group; $R_9$ is, for example, a linear or branched alkylene group or a linear or branched poly(alkyleneoxy) group, having 1-12 carbon atoms and represented by following Formula (8).

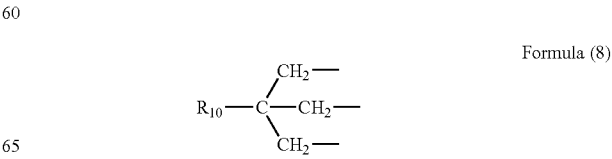

wherein $R_{10}$ is a lower alkyl group such as a methyl group, an ethyl group or a propyl group, or a multivalent group selected from the group consisting of following Formulas (9), (10) and (11).

Formula (9)

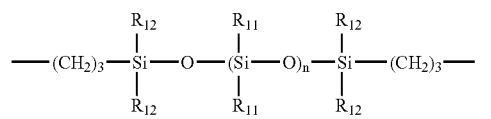

In Formula (9), "n" is an integer of 0-2,000, $R_{11}$ is an alkyl group of 1-10 carbon atoms such as a methyl group, ethyl group, propyl group or a butyl group, or a group selected from a group represented by following Formula (12).

Formula (12)

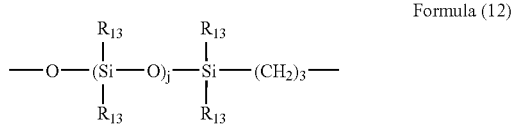

In above Formula (12), "j" is an integer of 0-100, $R_{13}$ is an alkyl group of 1-10 carbon atoms, and $R_{12}$ is an alkyl group of 1-10 carbon atoms such as a methyl group, ethyl group, propyl group or a butyl group.

Formula (10)

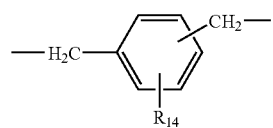

In above Formula (10), $R_{14}$ is a hydrogen atom, an alkyl group of 1-10 carbon atoms such as a methyl group, ethyl group, propyl group and a butyl group, an alkoxyl group of 1-10 carbon atoms, a halogen atom, a nitro group, a cyano group, a lower alkylcarboxylate group or a carboxyl group.

Formula (11)

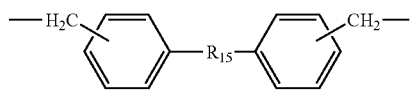

In above Formula (11), $R_{15}$ is an oxygen atom, a sulfur atom, NH, SO, $SO_2$, $CH_2$, $C(CH_3)_2$ or $C(CF_3)_2$.

Preferable as oxetane ring incorporating compounds usable in above Formulas (6) and (7) of this invention, $R_1$ is a lower alkyl group, especially an ethyl group; in Formula (9), $R_9$ is a group in which $R_{14}$ is a hydrogen atom, or a hexamethylene group; in Formula (8), $R_{10}$ is an ethyl group; in Formulas (9) and (12), $R_{12}$ and $R_{13}$ are each a methyl group; Z is a hydrocarbon group which does not contain an oxygen nor a sulfur atom; while $R_3$-$R_6$ are not a hydrogen atom at the same time.

Formula (13)

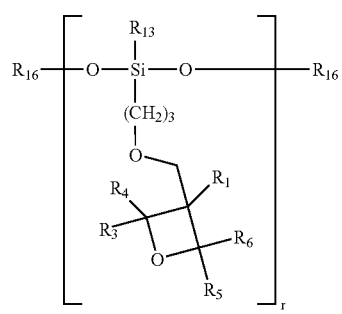

In Formula (13), "r" is an integer of 25-200, $R_{13}$ is the same as $R_{13}$ in above Formula (12), $R_{16}$ is an alkyl group of 1-4 carbon atoms or a trialkylsilyl group, while $R_4$-$R_6$ are not simultaneously a hydrogen atom.

Exemplified compounds represented by Formula (E) are described below, but the present invention is not limited to these examples.

E-1

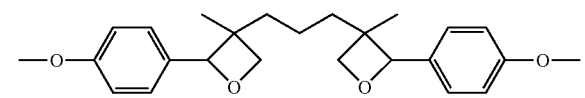

E-2

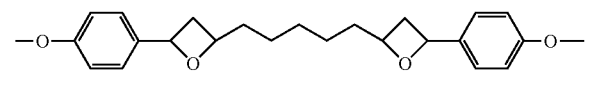

E-3

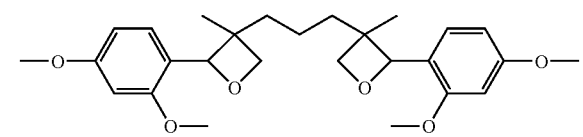

E-4

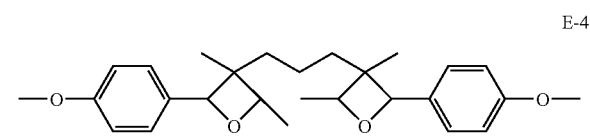

E-5

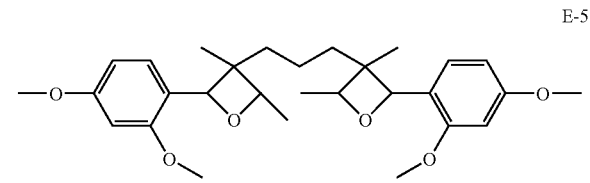

E-6

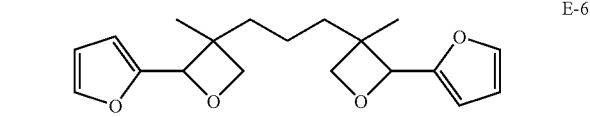

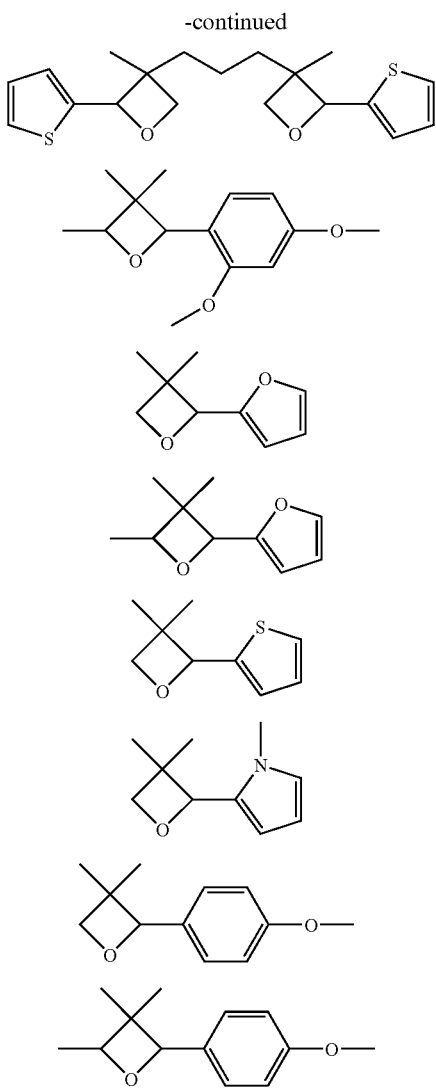

These compounds can be easily synthesized employing the methods described in "Kobunshikagaku to Yuukikagaku tono Cacchiboru (Pitch and Catch Between Polymer Science and Organic Chemistry)", the 4th session, or referring to the following documents.

1) Hu Xianming, Richard M. Kellogg, Synthesis, pp. 535-538, May (1995)

2) A. O. Fitton, J. Hill, D. Ejane, R. Miller, Synth., vol. 12, pg. 1140 (1987)

3) Toshiro Imai and Shinya Nishida, Can. J. Chem., Vol. 59, pp. 2503-2509 (1981)

4) Nobujiro Shimizu, Shintaro Yamaoka, and Yuho Tsuno, Bull. Chem. Soc. Jpn., vol. 56, pp. 3853-3854 (1983)

5) Walter Fisher and Cyril A. Grob, Helv. Chim. Acta., vol. 61, pp. 2336 (1978)

6) Chem., Ber., vol. 101, pg. 1850 (1968)

7) "Heterocyclic Compounds with Three- and Four-membered Rings", Part Two, Chapter IX, Interscience Publishers, John Wiley & Sons, New York (1964)

8) H. A. J. Curless, "Synthetic Organic Photochemistry", Plenum, New York (1984)

9) M. Braun, Nachr. Chem. Tech. Lab., vol. 33, pg. 213 (1985)

10) S. H. Schroeter, J. Org. Chem., vol. 34, No. 5, pg. 1181 (1969)

11) D. R. Arnold, Adv. Photochem., vol. 6, pg. 301 (1968)

Further, in the ink of this invention, the combination of a monofunctional oxetane compound containing one oxetane ring, and a multifunctional oxetane compound containing more than two oxetane rings, is more preferable to enhance film hardness and adhesion to a recording material after curing. However, when using a compound incorporating more than five oxetane rings, viscosity of the ink composition becomes excessive, resulting in difficulty in handling, and further, glass-transition temperature of the ink composition becomes excessive, resulting in insufficient adhesion of the cured material. The oxetane ring incorporating compound usable in this invention is preferably a compound containing 1-4 oxetane rings.

The active light curable ink of this invention contains the above mentioned active light curable composition and various well known dyes and/or pigments, pigments being preferable.

Pigments preferably employed in this invention are listed below.

C. I. Pigment Yellow-1, 3, 12, 13, 14, 17, 42, 81, 83, 87, 95, and 109

C.I. Pigment Orange-16, 36, and 38

C.I. Pigment Red-5, 22, 38, 48:1, 48:2, 48:4, 49:1, 53:1, 57:1, 63:1, 101, 144, 146, and 185

C.I. Pigment Violet-19 and 23

C.I. Pigment Blue-15:1, 15:3, 15:4, 18, 27, 29, and 60

C.I. Pigment Green-7 and 36

C.I. Pigment White-6, 18, and 21

C.I. Pigment Black-7

Further, in the present invention, in order to enhance covering power of color on transparent substrates such as plastic film, it is preferable to use a white ink. Specifically, in soft package printing and label printing, it is preferable to use a white ink. However, since the ejection amount needs to be increased, from the viewpoint of the foregoing ejection stability, and the likelihood of curling and wrinkling, the used amount needs to be limited.

The above pigments may be dispersed employing, for example, a ball mill, a sand mill, an attritor, a roller mill, an agitator, a Henschel mixer, a colloid mill, an ultrasonic homogenizer, a pearl mill, a wet type jet mill, or a paint shaker. Further, during dispersion of pigments, it is possible to add dispersing agents. Preferably employed as dispersing agents are polymer dispersing agents. Listed as polymer dispersing agents are any of the Solsperse-series available from Avecia Ltd. and any of the AJISPER PB-series available from Ajinomoto-Fine-Techno Co., Inc. Further, employed as dispersing aids may be synergists corresponding to each of the various types of pigments. The added amount of the aforesaid dispersing agents and dispersing aids is preferably 1-50 parts by weight with respect to 100 parts by weight of the pigments. Dispersion media are to be comprised of solvents or polymerizable compounds. In the radiation curable type ink employed in the present invention, in order to allow the aforesaid ink to undergo reaction and curing immediately after ink deposition, it is preferable to avoid solvents. When solvents remain in cured images, solvent resistance is degraded and VOC problems of remaining solvents also result. Therefore, it is preferable that in the dispersion media, polymerizable compounds are preferred instead of solvents. Of polymerizable compounds, from the viewpoint of appropriate dispersion, it is preferable to select monomers of the lowest viscosity.

Pigments are preferably dispersed to result in an average particle diameter of 0.08-0.5 μm. Suitable pigments, dispersing agents, dispersion media, dispersing conditions and filtering conditions are optionally selected and set so that the maximum particle diameter is controlled to be in the range of 0.3-10 μm and preferably 0.3-3 μm. By the foregoing particle diameter management, it is possible to minimize clogging of head nozzles, as well as to maintain storage stability of the ink, ink transparency and curing rate. Concentration of colorants in the photocurable ink of the present invention is preferably 1-10 weight % with respect to the total ink.

Other than those described above, employed in the active radiation curable ink of the present invention may be various additives. Listed, for example, are surface active agents, leveling additives, matting agents, polyester based resins, polyurethane based resins, vinyl based resins, acrylic based resins, rubber based resins, and waxes to adjust physical properties of the layers. Further, for the purpose of improving storage stability, it is possible to employ any of the effective basic compounds known in the art. Listed as representative compounds are basic alkali metal compounds, basic alkaline earth metal compounds, and basic organic compounds such as amines. Further it is possible to prepare a radical•cationic hybrid type curable ink by combining radically polymerizable monomers with initiators.

In order to achieve ejection stability as well as desired curability, irrespective of the curing ambience (temperature and humidity), the viscosity of the ink of the present invention is preferably 7-50 Pa·s at 25° C.

Other than common uncoated paper and coated paper, usable as recording materials in the present invention may be various types of non-absorptive plastics, and films thereof, which are employed in so-called soft packaging. Examples of various types of plastic films include polyethylene terephthalate (PET) film, oriented polystyrene (OPS) film, oriented polypropylene (OPP) film, oriented nylon (ONy) film, polyvinyl chloride (PVC) film, polyethylene (PE) film, and triacetyl cellulose (TAC) film. Employed as other plastics may be polycarbonates, acryl resins, ABSs, polyacetals, PVAs, and rubber materials. Further, metals and glass may also be employed. Of these recording materials, when images are formed, specifically on a PET film, an OPS film, an OPP film, an ONy film, or a PVC film all of which are thermally shrinkable, the effects of the embodiments of the present invention is more pronounced. These substrates tend to result in curling and deformation of the film due to contraction during ink curing and heat generated during the curing reaction. In addition, it is difficult for the ink layer to follow contraction of the foregoing substrate.

The surface energy of these various plastic films differs greatly. As a result, heretofore, problems have occurred in which dot diameter varies after ink deposition, depending largely on the recording materials. However, in the embodiment of the present invention, it is possible to form high-definition images on the recording materials having a surface energy ranging from 35-60 mN/m, including an OPP film as well as an OPS film having a relatively low surface energy and a PET film having a relatively high surface energy.

In the present invention, from the viewpoint of the cost of recording materials such as packaging cost as well as production cost, print production efficiency, and compatibility with various size prints, it is more advantageous to used rolled (web) recording materials.

Next, the image forming method of the present invention will be described.

In the image forming method of the present invention, a method is preferred in which the foregoing ink is ejected onto a recording material to form images, employing an ink-jet recording system, and subsequently the resulting ink is cured while exposed to active radiation, such as ultraviolet radiation.

In the present invention, the total ink layer thickness after curing, when ink is deposited on the recording material and exposed to active radiation, is preferably 2-20 μm. In the active radiation curable ink-jet recording of the screen-printing field, currently the total ink layer thickness exceeds 20 μm. However, in the soft package printing field, in which recording materials are comprised of relatively thin plastic materials, excessive ink ejection, which results in a thick ink layer, is not preferred because problems occur in which stiffness as well as the feel of quality of the entire printed materials varies, in addition to the foregoing problems of curling and wrinkling of recording materials.

Further, "total ink layer thickness", as described herein, refers to the maximum ink layer thickness of all images formed on a recording material. The foregoing total layer thickness is applied in the same manner, even though 2-color overprinting (secondary color), 3-color overprinting, or 4-color overprinting (with a white ink base) is carried out employing ink-jet recording systems.

Preferred ink ejection conditions are such that a recording head and the ejected ink are heated at 35-100° C. and ejection is performed to achieve ejection stability. The viscosity of the active radiation curable ink varies widely depending on the temperature. The resulting viscosity variation results in major effects to the liquid droplet size, as well as the liquid droplet ejection rate, which degrade image quality. As a result, it is necessary to maintain temperature at a constant value. The controlled temperature range of ink temperature is preferably the set temperature ±5° C., more preferably the set temperature ±2° C., and still more preferably the set temperature ±1° C.

Further, in the present invention, the volume of droplets ejected from each nozzle is preferably 2-15 pl. In order to form high-definition images, it is necessary to maintain the volume of a droplet in the foregoing range. However, when the foregoing droplet volume is ejected, it becomes more difficult to achieve the foregoing ejection stability. In the present invention, even though ejection is carried out at a small droplet volume of 2-15 pl, ejection stability is enhanced, whereby it is possible to consistently form high-definition images.

In the image forming method of the present invention, exposure to active radiation is preferably 0.001-2.0 seconds after ink deposition and more preferably 0.001-1.0 second. In order to form high-definition images, it is particularly critical that exposure timing is initiated as soon as possible.

A basic method for active radiation exposure is disclosed in JP-A 60-132767. According to the foregoing patent, light sources are arranged on both sides of a head unit and foregoing head and light sources are subjected to scanning, employing a shuttle system. Exposure is to be carried out a specifical time after ink deposition. Further, curing is completed employing another light source which is not driven. U.S. Pat. No. 6,145,979 discloses exposure methods in which optical fibers are employed and UV radiation is exposed to a recording section while collimated UV radiation is incident to a mirror surface provided on a side of the head unit surface. In the image forming method of the present invention, any of these exposure methods are effective.

Further, a preferred embodiment includes a method in which 2-step active radiation exposure is carried out in such a manner that first active radiation is exposed 0.001-2.0 seconds after ink deposition and after completion of printing, active radiation is further exposed onto the ink. By achieving the foregoing 2-step active radiation exposure, it is possible to minimize contraction of recording materials which occurs during ink curing.

Heretofore, in the UV ink-jet system, in order to minimize dot spread and bleeding after ink deposition, commonly employed are high illumination intensity light sources which consume at least 1 kW·hr. However, currently, it is practically impossible to use such light sources due to excessive contraction of recording materials, especially in shrink label printing.

In the present invention, it is preferable to use active radiation of the maximum illumination intensity in the wavelength region of 254 nm. Even when light sources at a total consumption of at least 1 kW·hr are employed, it is possible to form high-definition images and to control the contraction of recording materials within practical levels.

In the present invention, the total power consumption of light sources, which emit active radiation, is preferably less than 1 kW·hr. Examples of light sources at a total consumption of less than 1 kW·hr include, but are not limited to, fluorescent tubes, cold cathode tubes and LEDs.

The ink-jet recording apparatus (hereinafter referred simply to as the recording apparatus) will now be described.

The recording apparatus of the present invention will be described with reference to the drawing when considered as necessary. The recording apparatus in the drawing is one embodiment of the recording apparatus of the present invention, but the recording apparatus of the present invention is not limited thereto.

FIG. 1 is a front view showing the structure of the main section of the recording apparatus of the present invention. Recording apparatus 1 is comprised of head carriage 2, recording head 3, exposure means 4, and platen section 5. In recording apparatus 1, platen section 5 is arranged under recording material P. Platen section 5 exhibits an ultraviolet radiation absorbing function and absorbs excessive ultraviolet radiation which passes through recording material P, whereby it is possible to consistently reproduce high-definition images.

Recording material P is guided by guide member 6 and moves from the front to the rear of FIG. 1 by the operation of a conveying means (not shown). Head carriage 2 reciprocates in the Y direction in FIG. 1, whereby recording head 3, housed in head carriage 2, results in scanning.

Head carriage 2 is arranged above recording material P and houses a plurality of recording heads 3, described below, depending on the number of desired colors employed to print images. Ejection openings face downward. Head carriage 2 is arranged in recording apparatus 1 in such a manner that reciprocal motion is allowed in the Y direction in FIG. 1, driven by the head scanning means.

In FIG. 1, head carriage 2 houses recording heads 3 of white (W), yellow (Y), magenta (M), cyan (C), black (K), light yellow (Ly), light magenta (Lm), light cyan (Lc), light black (Lk), and white (W). However, in practice, the number of colors housed in carriage 2 is based on a need basis.

Recording heads 3 eject an active radiation curable ink (e.g., a UV curable ink) fed from an ink supply means (not shown) onto recording material P from the ejection openings by operation of a plurality of ejection means provided within the apparatus. The UV ink ejected from recording heads 3 is comprised of colorants, polymerizable monomers, and initiators, and exhibits curing properties to such a degree that when exposed to ultraviolet radiation, monomers undergo crosslinking and polymerization reaction, while the foregoing initiators function as a catalyst.

Recording head 3 is scans from one edge of recording material P to the other edge in the Y direction in FIG. 1, while driven by the head scanning means. During scanning, a UV ink is ejected in the form of ink droplets onto a definite region (ink droplet receivable region), whereby ink droplets are impinged onto the foregoing ink droplet receiving region.

The foregoing scanning is appropriately repeated and the UV ink is ejected within one of the ink droplet receivable regions. Subsequently, recording material P is appropriately conveyed from the front to the rear of FIG. 1, employing a conveying means and scanning is repeated employing the head scanning means. During the foregoing scanning, the UV ink is ejected onto the subsequent ink droplet receiving region in the rear of FIG. 1, adjacent to the foregoing ink droplet receivable region.

The foregoing operation is then repeated and an image comprised of UV ink droplets is formed on recording material P ejected from recording heads 3, in synchronization with the head scanning means and the conveying means.

Exposure means 4 is comprised of an ultraviolet radiation lamp which emits ultraviolet radiation of a specified wavelength region at a uniform exposure energy, and a filter which transmits the ultraviolet radiation of the specified wavelengths. Herein, employed as the ultraviolet radiation lamp may be a mercury lamp, a metal halide lamp, an excimer laser, an ultraviolet laser, a hot cathode tube, a cold cathode tube, a black-light lamp, and an LED (being a light emitting diode). Of these, preferred are a band-shaped metal halide lamp, a cold cathode tube, a mercury lamp, and a black-light lamp. Specifically preferred are a low-pressure mercury lamp, a hot cathode tube, a cold cathode tube and a sterilization lamp which emit ultraviolet radiation at a wavelength of 254 nm, whereby bleeding is minimized, and dot diameter is effectively controlled. By employment of a hot cathode tube as a radiation source of exposure means 4, it is possible to produce exposure means 4 to cure the UV ink at lower cost.

Exposure means 4 is structured to be nearly equal to the maximum size which can be housed in recording apparatus 1 (being a UV ink-jet printer) of the ink dot receiving region, in which the UV ink is ejected during one cycle of scanning, in which recording heads 3 are driven by the head scanning means, or is structured to be larger than the ink dot receiving region.

Exposure means 4 are arranged and fixed on both sides of head carriage 2, being nearly equidistant from recording material P.

As noted above, as a means to control illuminance in the ink ejection section, obviously, all recording heads 3 must be shielded from light. In addition, it is effective that distance h2 between ink ejection section 31 of recording heads 3 and recording material P is maintained to be greater than distance h1 between exposure means 4 and recording material P (i.e., h1<h2) and/or distance d between recording heads 3 and exposure means 4 increases (d increases). Further, it is more preferable that bellows structure 7 is arranged between recording heads 3 and exposure means 4.

Herein, it is possible to change to the suitable wavelength of ultraviolet radiation which is employed by exposure means 4, by replacing the ultraviolet radiation lamp or filters provided in exposure means 4.

The ink of this invention is very superior in ink ejection stability, so that it is effectively employed for image formation using a line head type recording apparatus.

Figure 2:
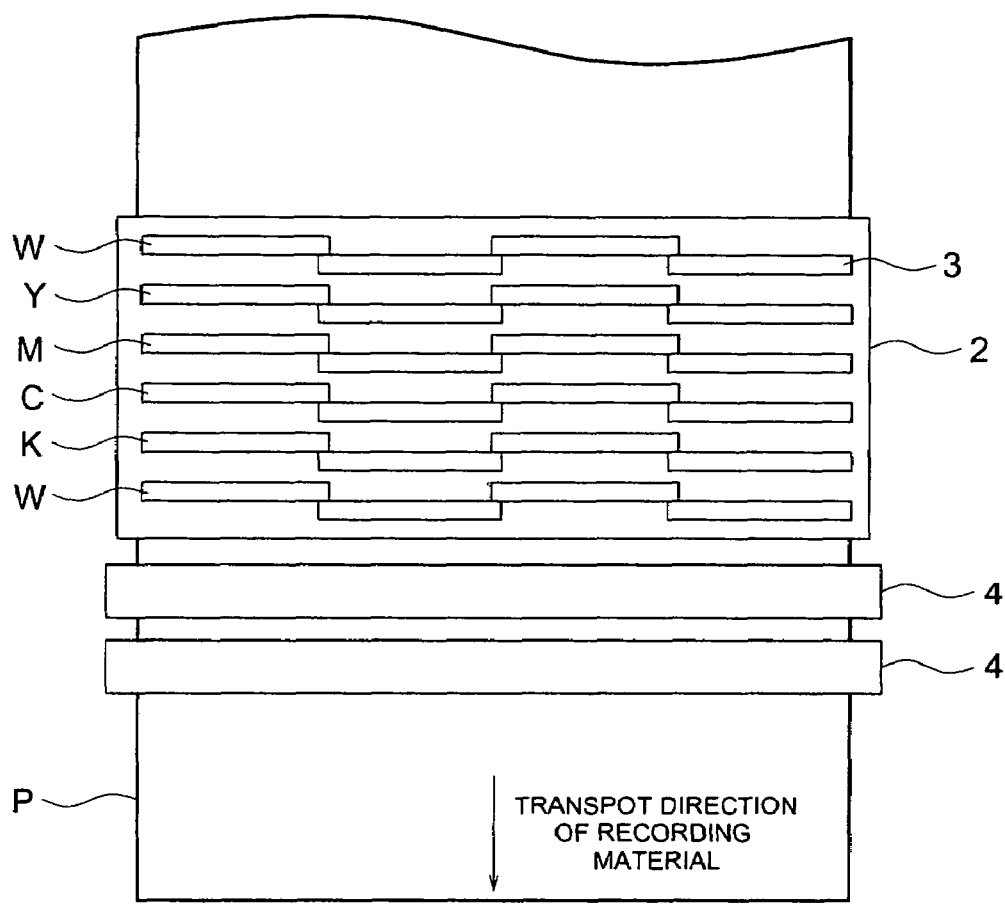
FIG. 2 is a top view showing an example of the constitution of substantial parts of an ink-jet recording apparatus employed in this invention.

FIG. 2 is a top view of another example showing the structure of the main section of the recording apparatus of the present invention.

The ink recording apparatus shown in FIG. 2 is a so-called line head method, in which a plurality of ink jet recording heads 3 for each color are arranged and fixed to head carriage 2 so as to eject onto the full width of recording material P.

Meantime, downstream of head carriage 2, exposure means 4 is provided to similarly enable ejection onto the total ink printing area, thereby enabling printing of the full width of recording material P. The UV lamp used in exposure means 4 is similar to the one described in FIG. 1.

In this line head method, head carriage 2 and exposure means 4 are fixed and only recording material P is conveyed, after which ink ejection and curing are conducted to form images.

EXAMPLE

The present invention is further described with the exemplified examples below, but the present invention is not limited to these examples.

Example 1

Preparation of Ink Composition Set

Based on the following methods, Ink Composition Sets 1-8 were prepared comprising components described in Tables 1-8.

Added to a stainless steel beaker were 3 weight parts of dispersing agent (being PB822, produced by Ajinomoto-Fine-Techno Co., Inc.) and each of photopolymerizable compound described in Tables 1-8, after which the mixture was heated on a hot plate to 65° C. and dissolved while stirring for one hour. Subsequently, to this solution, the colorant described in Tables 1-6 was added, after which the resulting solution was poured into a plastic bottle together with 200 g of 1 mm diameter zirconia beads, and then dispersion treatment was conducted over two hours using a paint shaker. After that, the zirconia beads were removed, and various additives such as a photo-induced acid generating agent, an Acid multiplying agent, and a surface active agent were added in the combinations described in Tables 1-8. The resulting solutions were filtered to prevent clogging of a printer, and Ink Composition Sets 1-8 were prepared. Herein, ink viscosity of each color of each Ink Composition Sets prepared above (at a temperature of 25° C.) is as follows. Viscosity was indicated by a viscosity range of the maximum and the minimum viscosity of each color.

Ink Composition Set 1: 28-33 mPa·s
Ink Composition Set 2: 31-34 mPa·s
Ink Composition Set 3: 24-27 mPa·s
Ink Composition Set 4: 22-26 mPa·s
Ink Composition Set 5: 28-33 mPa·s
Ink Composition Set 6: 24-27 mPa·s
Ink Composition Set 7: 25-28 mPa·s
Ink Composition Set 8: 27-31 mPa·s

TABLE 1

| | | | | Ink Composition (weight %) | | | | |
|---|---|---|---|---|---|---|---|---|
| | | Colorant | | Photopolymerizable compound | | Acid multiplying | Photo-induced acid generating | Dispersing |
| Ink kind | Kind | Added amount | | *E1 Celloxide 2021P | *O OXT-221 | agent Acpres 11M | agent UVI 16992 | agent PB822 |
| Ink Composition Set 1 (Comparative Example) | K | 1 | 4.0 | 27.0 | 60.0 | 1.0 | 5.0 | 3.0 |
| | C | 2 | 4.0 | 19.0 | 70.0 | 1.0 | 3.0 | 3.0 |
| | M | 3 | 5.0 | 18.0 | 70.0 | 1.0 | 3.0 | 3.0 |
| | Y | 4 | 5.0 | 18.0 | 70.0 | 1.0 | 3.0 | 3.0 |
| | W | 5 | 5.0 | 28.0 | 60.0 | 1.0 | 3.0 | 3.0 |
| | Lk | 1 | 1.0 | 22.0 | 70.0 | 1.0 | 3.0 | 3.0 |
| | Lc | 2 | 1.0 | 22.0 | 70.0 | 1.0 | 3.0 | 3.0 |
| | Lm | 3 | 1.3 | 21.8 | 70.0 | 1.0 | 3.0 | 3.0 |
| | Ly | 4 | 1.3 | 21.8 | 70.0 | 1.0 | 3.0 | 3.0 |

TABLE 2

| | | | | Ink Composition (weight %) | | | | | | | |
|---|---|---|---|---|---|---|---|---|---|---|---|
| | | Colorant | | Photopolymerizable compound | | Acid multiplying | Surface active agent | | | Photo-induced acid generating | Dispersing |
| Ink kind | Kind | Added amount | | *E1 Celloxide 2021P | *O Compound E-2 | agent Acpres 11M | OP-85R | F178k | *1 | agent Compound S-5 | agent PB822 |
| Ink Composition Set 2 (This Invention) | K | 1 | 4.0 | 34.4 | 50.0 | 1.0 | 0.10 | 0.02 | 5.0 | 2.5 | 3.0 |
| | C | 2 | 4.0 | 24.9 | 60.0 | 1.0 | 0.10 | 0.02 | 5.0 | 2.0 | 3.0 |
| | M | 3 | 5.0 | 23.9 | 60.0 | 1.0 | 0.10 | 0.02 | 5.0 | 2.0 | 3.0 |
| | Y | 4 | 5.0 | 23.9 | 60.0 | 1.0 | 0.10 | 0.02 | 5.0 | 2.0 | 3.0 |
| | W | 5 | 5.0 | 33.4 | 50.0 | 1.0 | 0.10 | 0.02 | 5.0 | 2.5 | 3.0 |
| | Lk | 1 | 1.0 | 27.9 | 60.0 | 1.0 | 0.10 | 0.02 | 5.0 | 2.0 | 3.0 |
| | Lc | 2 | 1.0 | 27.9 | 60.0 | 1.0 | 0.10 | 0.02 | 5.0 | 2.0 | 3.0 |
| | Lm | 3 | 1.3 | 27.6 | 60.0 | 1.0 | 0.10 | 0.02 | 5.0 | 2.0 | 3.0 |
| | Ly | 4 | 1.3 | 27.6 | 60.0 | 1.0 | 0.10 | 0.02 | 5.0 | 2.0 | 3.0 |

TABLE 3

Ink Composition (weight %)

| Ink kind | | Colorant | | Photopolymerizable compound | | | Acid multiplying agent Acpres 11M | Basic compound *2 | Surface active agent | | *3 | Photo-induced acid generating agent Compound S-2 | Dispersing agent PB822 |
|---|---|---|---|---|---|---|---|---|---|---|---|---|---|
| | | Kind | Added amount | *E2 D-55 | OXT-221 | *O Compound E-13 | | | F178k | F1405 | | | |
| Ink Composition Set 3 (This Invention) | K | 1 | 4.0 | 30.0 | 31.9 | 20.0 | 3.0 | 0.10 | 0.02 | 0.02 | 5.0 | 3.0 | 3.0 |
| | C | 2 | 4.0 | 30.0 | 32.4 | 20.0 | 3.0 | 0.10 | 0.02 | 0.02 | 5.0 | 2.5 | 3.0 |
| | M | 3 | 5.0 | 30.0 | 31.4 | 20.0 | 3.0 | 0.10 | 0.02 | 0.02 | 5.0 | 2.5 | 3.0 |
| | Y | 4 | 5.0 | 30.0 | 31.4 | 20.0 | 3.0 | 0.10 | 0.02 | 0.02 | 5.0 | 2.5 | 3.0 |
| | W | 5 | 5.0 | 30.0 | 30.9 | 20.0 | 3.0 | 0.10 | 0.02 | 0.02 | 5.0 | 3.0 | 3.0 |
| | Lk | 1 | 1.0 | 30.0 | 35.4 | 20.0 | 3.0 | 0.10 | 0.02 | 0.02 | 5.0 | 2.5 | 3.0 |
| | Lc | 2 | 1.0 | 30.0 | 35.4 | 20.0 | 3.0 | 0.10 | 0.02 | 0.02 | 5.0 | 2.5 | 3.0 |
| | Lm | 3 | 1.3 | 30.0 | 35.1 | 20.0 | 3.0 | 0.10 | 0.02 | 0.02 | 5.0 | 2.5 | 3.0 |
| | Ly | 4 | 1.3 | 30.0 | 35.1 | 20.0 | 3.0 | 0.10 | 0.02 | 0.02 | 5.0 | 2.5 | 3.0 |

TABLE 4

Ink Composition (weight %)

| Ink kind | Colorant | | Photopolymerizable compound | | | Acid multiplying agent | Photo-induced acid generating agent | Dispersing agent |
|---|---|---|---|---|---|---|---|---|
| | Kind | Added amount | *E1 CELLOXIDE 3000 | OXT-221 | *O OXT-211 | Compound 1 | UVI 6992 | PB 822 |
| Ink Composition Set 4 (This Invention) | K | 1 | 4.0 | 25.0 | 40.0 | 20.0 | 3.0 | 5.0 | 3.0 |
| | C | 2 | 4.0 | 18.5 | 50.0 | 20.0 | 1.5 | 3.0 | 3.0 |
| | M | 3 | 5.0 | 17.5 | 50.0 | 20.0 | 1.5 | 3.0 | 3.0 |
| | Y | 4 | 5.0 | 17.5 | 50.0 | 20.0 | 1.5 | 3.0 | 3.0 |
| | W | 5 | 5.0 | 25.5 | 40.0 | 20.0 | 1.5 | 5.0 | 3.0 |

TABLE 5

Ink Composition (weight %)

| Ink kind | | Colorant | | Photopolymerizable compound | | | | Acid multiplying agent | Basic compound *4 | Surface active agent | | *3 | Photo-induced acid generating agent Compound I-3 | Dispersing agent PB 822 |
|---|---|---|---|---|---|---|---|---|---|---|---|---|---|---|
| | | Kind | Added amount | *E1 CELLOXIDE 3000 | *E2 E-4030 | *O Compound E-4 | OXT-211 | Compound 2 | | OP-85R | F470 | | | |
| Ink Composition Set 5 (This Invention) | K | 1 | 4.0 | 11.7 | 15.0 | 40.0 | 15.0 | 3.0 | 0.20 | 0.10 | 0.02 | 5.0 | 3.0 | 3.0 |
| | C | 2 | 4.0 | 16.7 | 15.0 | 35.0 | 15.0 | 3.0 | 0.20 | 0.10 | 0.02 | 5.0 | 3.0 | 3.0 |
| | M | 3 | 5.0 | 15.7 | 15.0 | 35.0 | 15.0 | 3.0 | 0.20 | 0.10 | 0.02 | 5.0 | 3.0 | 3.0 |
| | Y | 4 | 5.0 | 15.7 | 15.0 | 35.0 | 15.0 | 3.0 | 0.20 | 0.10 | 0.02 | 5.0 | 3.0 | 3.0 |
| | W | 5 | 5.0 | 5.7 | 20.0 | 40.0 | 15.0 | 3.0 | 0.20 | 0.10 | 0.02 | 5.0 | 3.0 | 3.0 |

TABLE 6

Ink Composition (weight %)

| | | | Photopolymerizable compound *O | | Acid multiplying agent | Basic compound *4 | Surface active agent | | Photo-induced acid generating agent | Dispersing agent |
|---|---|---|---|---|---|---|---|---|---|---|
| | Colorant | | | | | | | | | |
| Ink kind | Kind | Added amount | Compound E-1 | Compound E-13 | Compound 1 | | TF 907 | *5 | Compound S-7 | PB 822 |
| Ink Composition Set 6 (This Invention) | K | 1 | 4.0 | 61.9 | 20.0 | 3.0 | 0.1 | 0.02 | 5.0 | 3.0 | 3.0 |
| | C | 2 | 4.0 | 63.4 | 20.0 | 1.5 | 0.1 | 0.02 | 5.0 | 3.0 | 3.0 |
| | M | 3 | 5.0 | 62.4 | 20.0 | 1.5 | 0.1 | 0.02 | 5.0 | 3.0 | 3.0 |
| | Y | 4 | 5.0 | 62.4 | 20.0 | 1.5 | 0.1 | 0.02 | 5.0 | 3.0 | 3.0 |
| | W | 5 | 5.0 | 62.4 | 20.0 | 1.5 | 0.1 | 0.02 | 5.0 | 3.0 | 3.0 |

TABLE 7

Ink Composition (weight %)

| | Colorant | | Photopolymerizable compound | | | Basic compound *2 | Surface active agent | | Photo-induced acid generating agent $PF_6^-$ salt of Formula (10) | Dispersing agent PB 822 |
|---|---|---|---|---|---|---|---|---|---|---|
| | | | *E3 | *E1 | *O | | | | | |
| Ink kind | Kind | Added amount | Vikoflex 7010 | CELLOXIDE 3000 | OXT-221 | Compound E-2 | F 470 | TF 907 | *3 | |
| Ink Composition Set 7 (This Invention) | K | 1 | 4.0 | 8.0 | 39.9 | 30.0 | 5.0 | 0.10 | 0.02 | 0.02 | 5.0 | 3.0 | 5.0 |
| | C | 2 | 4.0 | 8.0 | 40.4 | 30.0 | 5.0 | 0.10 | 0.02 | 0.02 | 5.0 | 2.5 | 5.0 |
| | M | 3 | 5.0 | 8.0 | 39.4 | 30.0 | 5.0 | 0.10 | 0.02 | 0.02 | 5.0 | 2.5 | 5.0 |
| | Y | 4 | 5.0 | 8.0 | 39.4 | 30.0 | 5.0 | 0.10 | 0.02 | 0.02 | 5.0 | 2.5 | 5.0 |
| | W | 5 | 5.0 | 8.0 | 38.9 | 30.0 | 5.0 | 0.10 | 0.02 | 0.02 | 5.0 | 3.0 | 5.0 |
| | Lk | 1 | 1.0 | 8.0 | 43.4 | 30.0 | 5.0 | 0.10 | 0.02 | 0.02 | 5.0 | 2.5 | 5.0 |
| | Lc | 2 | 1.0 | 8.0 | 43.4 | 30.0 | 5.0 | 0.10 | 0.02 | 0.02 | 5.0 | 2.5 | 5.0 |
| | Lm | 3 | 1.3 | 8.0 | 43.1 | 30.0 | 5.0 | 0.10 | 0.02 | 0.02 | 5.0 | 2.5 | 5.0 |
| | Ly | 4 | 1.3 | 8.0 | 43.1 | 30.0 | 5.0 | 0.10 | 0.02 | 0.02 | 5.0 | 2.5 | 5.0 |

TABLE 8

Ink Composition (weight %)

| | Colorant | | Photopolymerizable compound | | | | Basic compound *4 | Surface active agent | | Photo-induced acid generating agent $PF_6^-$ salt of Formula (13) | Dispersing agent PB 822 |
|---|---|---|---|---|---|---|---|---|---|---|---|
| | | | *E3 | *E1 | O* | | | | | | |
| Ink kind | Kind | Added amount | Vikoflex 9010 | LDO | OXT-221 | RSOX | Compound E-2 | | F4 75 | TF 907 | *5 | |
| Ink Composition Set 8 (This Invention) | K | 1 | 4.0 | 12.9 | 30.0 | 25.0 | 10.0 | 6.0 | 0.10 | 0.02 | 0.02 | 3.0 | 4.0 | 5.0 |
| | C | 2 | 4.0 | 12.9 | 30.0 | 25.0 | 10.0 | 6.0 | 0.10 | 0.02 | 0.02 | 3.0 | 4.0 | 5.0 |
| | M | 3 | 5.0 | 11.9 | 30.0 | 25.0 | 10.0 | 6.0 | 0.10 | 0.02 | 0.02 | 3.0 | 4.0 | 5.0 |
| | Y | 4 | 5.0 | 11.9 | 30.0 | 25.0 | 10.0 | 6.0 | 0.10 | 0.02 | 0.02 | 3.0 | 4.0 | 5.0 |
| | W | 5 | 5.0 | 11.9 | 30.0 | 25.0 | 10.0 | 6.0 | 0.10 | 0.02 | 0.02 | 3.0 | 4.0 | 5.0 |

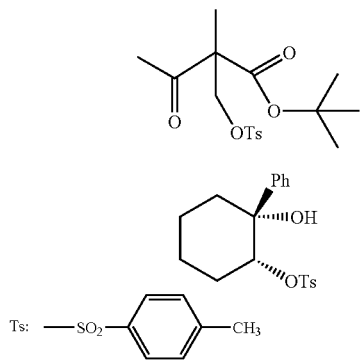

Compound 1

Compound 2

Ts: —SO₂—⟨C₆H₄⟩—CH₃

Each of the inks and compounds, and the details of indications described in Tables 1-8 are shown below.
- K: a dark black ink
- C: a dark cyan ink
- M: a dark magenta ink
- Y: a dark yellow ink
- W: a white ink
- Lk: a light black ink
- Lc: a light cyan ink
- Lm: a light magenta ink
- Ly: a light yellow ink
- Colorant 1: C. I. Pigment Black 7
- Colorant 2: C. I, Pigment Blue 15:3
- Colorant 3: C. I. Pigment Red 57:1
- Colorant 4: C. I. Pigment Yellow 13
- Colorant 5: Titanium oxide (being an anatase type at an average particle diameter of 0.20 μm)

Photopolymerizable Compound
*E1: an alicyclic epoxy compound
CELLOXIDE 2021P: produced by DAI CEL CHEMICALS, LTD.
CELLOXIDE 3000: produced by DAI CEL CHEMICALS, LTD.
LDO: produced by ATOFINA Chemicals, Inc.
*E2: epoxidized fatty acid isobutyl
D-55: ADEKACIZER D-55 (produced by ASAHIDENKA CO., LTD., being an epoxidized fatty acid butyl epoxy compound)
E-4030: SANSOCIZER E-4030 (produced by New Japan Chemical Co., Ltd., being an epoxidized fatty acid butyl)
*E3: epoxidized soybean oil
Vikoflex 7010: produced by ATOFINA Chemicals, Inc.
Vikoflex 9010: produced by ATOFINA Chemicals, Inc.
*O: an oxetane compound
OXT-211: 3-ethyl-3 (phenoxymethyl)oxetane (produced by TOAGOSEI CO., LTD.)
OXT-221: di[1-ethyl(3-oxetanyl)]methyl ether (produced by TOAGOSEI CO., LTD.)
RSOX: produced by TOAGOSEI CO., LTD.

Acid Multiplying Agent
Acpres 11M: produced by Japan Chemix Ltd.

Photo-induced Acid Generating Agent
UVI 6992: triphenylsulfonium salt (CYRACURE UVI 6992, produced by Union Carbide Corp.) 50% solution of propioncarbonate.

Surface Active Agent
F 178k: MEGAFACE F 178k (being an acryl oligomer containing a perfluoroalkyl group) produced by DAINIPPON INK AND CHEMICALS, INCORPORATED
OP-85R: Nonion OP-85R (being a sorbitan ester type nonionic surface active agent); sorbitantrioleate (HLB=1.8), produced by NOF CORPORATION)
F 1405: Megaface F 1405, being an ethylene oxide addition product containing a perfluoroalkyl group, produced by DAINIPPON INK AND CHEMICALS, INCORPORATED
F 470: MEGAFACE F 470, being an acryl oligomer containing a perfluoroalkyl group, produced by DAINIPPON INK AND CHEMICALS, INCORPORATED
TF 907: MEGAFACE EXP TF 907: being an ethylene oxide addition product containing a perfluoroalkyl group, produced by DAINIPPON INK AND CHEMICALS, INCORPORATED Dispersion Agent
PB 822: produced by Ajinomoto-Fine-Techno Co., Inc.

Others
*1: γ-caprolactone (being a reagent, produced by KANTO KAGAKU
*2: N-ethyldiethanolamine (being a basic compound)
*3: propylene carbonate (being a reagent, produced by KANTO KAGAKU
*4: tributylamine (being a basic compound)
*5: γ-butyrolactone (being a reagent, produced by KANTO KAGAKU Ink-jet Image Forming Method To the ink-jet recording apparatus comprised of the compositions as described in FIG. 1, which is provided with piezo type ink-jet nozzles, each of Ink Composition Sets 1-3 and 7 prepared as above was loaded, and the following image recording was continuously conducted onto the recording material of a web roll of 600 mm width and 500 m length, which had the surface energy listed in Tables 9 and 10. The ink supply system consisted of an ink tank, a supply pipe, an anterior chamber ink tank immediately preceding a head, piping provided with a filter, and a piezo head. The portion from the anterior chamber to the head was thermally insulated and heated to 50° C. The piezo head was driven to eject multi-sized dots of 2-15 pl at resolution of 720×720 dpi, and each of inks was continuously ejected. After deposition of each ink, ultraviolet radiation, from lamp units provided on both sides of the carriage, was instantaneously conducted (being less than two seconds after ink deposition) using radiation light source A of a hot cathode tube, whereby the inks were cured. After image recording, the total ink layer thickness was measured, and the thickness was within the range of 2.3-13 μm. Herein, "dpi" in this invention is dots per inch (being 2.54 cm).

Subsequently, using a line head method ink-jet recording apparatus described in FIG. 2, Ink Composition Sets 4-6 and 8 were employed similarly to form images by UV radiation to cure the inks, by using two low pressure mercury lamps (being a linear light source) as radiation light source B.

Employing the above two methods, printing was conducted under the three conditions of at 10° C., 20% RH; 25° C., 50% RH and 30° C., 80% RH.

The details of the radiation light sources described in Tables 9 and 10 are as follows.

Radiation light source A: a hot cathode tube (being a U-tube, produced by NIPPO ELECTRIC CO., LTD., and light source power consumption being less than 1 kW·hr.)

Radiation light source B: a low-pressure mercury vapor lamp (being a special order item, produced by IWASAKI ELECTRIC Co., Ltd.)

Further, illuminance of each radiation light source described in Tables 9 and 10 was indicated by measurement of the accumulated illuminance at 220-420 nm, using URS 40 manufactured by USHIO INC.

The details of the radiation locations described in Tables 9 and 10 are shown below.
*1: both sides of the recording head (being the method of FIG. 1)
*2: downstream of the conveyance direction of the recording material (being the method of FIG. 2)

The details of the abbreviated name of each recording material are shown below.
OPP: oriented polypropylene
PET: polyethylene terephthalate
PVC: polyvinyl chloride

TABLE 9

| | | Recording material | | Radiation condition | | | | | |
|---|---|---|---|---|---|---|---|---|---|
| | | | | | Radiation method (area) | Radiation | | On surface of recording material | |
| Sample No. | Ink set No. | Kind | Surface energy mN/m | Radiation light source | Radiation location | Light source | timing (after deposition) | Peak wavelength (nm) | Maximum illuminance (mW/cm$^2$) | Remarks |
| 1 | 1 | OPP | 38 | A | *1 | *5 | After 0.2 sec. | 254 | 12 | Comp. |
| 2 | 1 | PET | 53 | A | *1 | *5 | After 0.2 sec. | 254 | 12 | Comp. |
| 3 | 1 | PVC | 45 | A | *1 | *5 | After 0.2 sec. | 254 | 12 | Comp. |
| 4 | 1 | *3 | *4 | A | *1 | *5 | After 0.2 sec. | 254 | 12 | Comp. |
| 5 | 2 | OPP | 38 | A | *1 | *5 | After 0.2 sec. | 254 | 12 | Inv. |
| 6 | 2 | PET | 53 | A | *1 | *5 | After 0.2 sec. | 254 | 12 | Inv. |
| 7 | 2 | PVC | 45 | A | *1 | *5 | After 0.2 sec. | 254 | 12 | Inv. |
| 8 | 2 | *3 | *4 | A | *1 | *5 | After 0.2 sec. | 254 | 12 | Inv. |
| 9 | 3 | OPP | 38 | A | *1 | *5 | After 0.2 sec. | 254 | 12 | Inv. |
| 10 | 3 | PET | 53 | A | *1 | *5 | After 0.2 sec. | 254 | 12 | Inv. |
| 11 | 3 | PVC | 45 | A | *1 | *5 | After 0.2 sec. | 254 | 12 | Inv. |
| 12 | 3 | *3 | *4 | A | *1 | *5 | After 0.2 sec. | 254 | 12 | Inv. |
| 13 | 4 | OPP | 38 | B | *2 | *5 | After 0.1 sec. | 254 | 40 | Comp. |
| 14 | 4 | PET | 53 | B | *2 | *5 | After 0.1 sec. | 254 | 40 | Comp. |
| 15 | 4 | PVC | 45 | B | *2 | *5 | After 0.1 sec. | 254 | 40 | Comp. |
| 16 | 4 | *3 | *4 | B | *2 | *5 | After 0.1 sec. | 254 | 40 | Comp. |

*1: both sides of the recording head (FIG. 1 method)
*2: downstream of the conveyance direction of the recording material (FIG. 2 method)
*3: Cast coated paper
*4: Absorptive recording material
*5: Linear light source
Note:
Comp.; Comparative example
Inv.; This invention

TABLE 10

| | | Recording material | | Radiation condition | | | | | |
|---|---|---|---|---|---|---|---|---|---|
| | | | | | Radiation method (area) | Radiation | | On surface of recording material | |
| Sample No. | Ink set No. | Kind | Surface energy (mV/m) | Radiation light source | Radiation location | Light source | timing (after deposition) | Peak wavelength (nm) | Maximum illuminance (mW/cm$^2$) | Remarks |
| 17 | 5 | OPP | 38 | B | *2 | *5 | After 0.1 sec. | 254 | 40 | Inv. |
| 18 | 5 | PET | 53 | B | *2 | *5 | After 0.1 sec. | 254 | 40 | Inv. |
| 19 | 5 | PVC | 45 | B | *2 | *5 | After 0.1 sec. | 254 | 40 | Inv. |
| 20 | 5 | *3 | *4 | B | *2 | *5 | After 0.1 sec. | 254 | 40 | Inv. |
| 21 | 6 | OPP | 38 | B | *2 | *5 | After 0.1 sec. | 254 | 40 | Inv. |
| 22 | 6 | PET | 53 | B | *2 | *5 | After 0.1 sec. | 254 | 40 | Inv. |
| 23 | 6 | PVC | 45 | B | *2 | *5 | After 0.1 sec. | 254 | 40 | Inv. |
| 24 | 6 | *3 | *4 | B | *2 | *5 | After 0.1 sec. | 254 | 40 | Inv. |
| 25 | 7 | OPP | 38 | A | *1 | *5 | After 0.2 sec. | 254 | 12 | Inv. |
| 26 | 7 | PET | 53 | A | *1 | *5 | After 0.2 sec. | 254 | 12 | Inv. |
| 27 | 7 | PVC | 45 | A | *1 | *5 | After 0.2 sec. | 254 | 12 | Inv. |
| 28 | 7 | *3 | *4 | A | *1 | *5 | After 0.2 sec. | 254 | 12 | Inv. |
| 29 | 8 | OPP | 38 | B | *2 | *5 | After 0.1 sec. | 254 | 40 | Inv. |

TABLE 10-continued

| Sample No. | Ink set No. | Recording material Kind | Surface energy (mV/m) | Radiation light source | Radiation method (area) Radiation loca-tion | Light source | Radiation timing (after deposition) | On surface of recording material Peak wavelength (nm) | Maximum illuminance (mW/cm$^2$) | Remarks |
|---|---|---|---|---|---|---|---|---|---|---|
| 30 | 8 | PET | 53 | B | *2 | *5 | After 0.1 sec. | 254 | 40 | Inv. |
| 31 | 8 | PVC | 45 | B | *2 | *5 | After 0.1 sec. | 254 | 40 | Inv. |
| 32 | 8 | *3 | *4 | B | *2 | *5 | After 0.1 sec. | 254 | 40 | Inv. |

*1: both sides of recording head (FIG. 1 method)
*2: downstream of conveyance direction of recording material (FIG. 2 method)
*3: Cast coated paper
*4: Absorptive recording material
*5: Linear light source
Inv.; This invention Evaluation of Ink-jet Recorded Image Each of the images recorded with the above recording methods, was evaluated for the following characteristics.

Evaluation of Text Quality

MS Ming-style characters of 6 points at the targeted density were printed using the Y, M, C and K inks, and roughness of characters was observed via magnification using a loupe to evaluate text quality based on the following criteria.

A: No roughness was observed.

B: Slight roughness was observed.

C: Roughness was observed, but each character was identifiable, and at a barely acceptable level.

D: Severe roughness was observed, and the characters were faint and patchy, at an unacceptable level.

Evaluation of Color Mixing (Bleeding)

Dots of each color of Y, M, C and K were printed so as to be adjacent, and each color dot next to other color dots was visually observed under magnification using a loupe to evaluate color mixing, being bleeding, based on the following criteria.

A: Adjacent dots maintained perfect circularity, and no bleeding was observed.

B: Adjacent dots maintained nearly perfect circularity, and only slight bleeding was observed.

C: Adjacent dots bled slightly with noticeable loss of circularity, but still at a barely usable level.

D: Adjacent dots bled and obviously mixed with each other, resulting in at an unacceptable level.

The evaluation results of the above tests are shown in Table 11.

TABLE 11

| | 10° C., 20% RH | | 25° C., 50% RH | | 30° C., 80% RH | | |
|---|---|---|---|---|---|---|---|
| Sample No. | Text quality | Color mixing (Bleeding) | Text quality | Color mixing (Bleeding) | Text quality | Text quality | Remarks |
| 1 | C | C | D | C | D | D | Comp. |
| 2 | B | D | D | D | D | D | Comp. |
| 3 | B | C | D | D | D | D | Comp. |
| 4 | B | C | C | D | C | D | Comp. |
| 5 | B | A | B | A | B | B | Inv. |
| 6 | A | B | A | B | B | B | Inv. |
| 7 | A | A | A | B | B | B | Inv. |
| 8 | A | A | A | B | B | B | Inv. |
| 9 | B | A | B | A | B | B | Inv. |
| 10 | A | B | A | B | A | B | Inv. |
| 11 | A | A | A | B | A | B | Inv. |
| 12 | A | A | A | A | A | A | Inv. |
| 13 | B | B | D | D | D | D | Comp. |
| 14 | B | B | C | D | D | D | Comp. |
| 15 | B | B | C | D | D | D | Comp. |
| 16 | B | B | C | D | C | D | Comp. |
| 17 | B | A | B | B | B | B | Inv. |
| 18 | B | B | B | B | B | B | Inv. |
| 19 | B | B | B | B | B | B | Inv. |
| 20 | A | A | A | A | A | A | Inv. |
| 21 | B | A | B | A | B | A | Inv. |
| 22 | A | B | A | B | A | B | Inv. |
| 23 | B | A | B | B | B | B | Inv. |
| 24 | A | A | A | A | A | A | Inv. |
| 25 | B | A | B | A | B | B | Inv. |
| 26 | B | B | B | B | B | B | Inv. |
| 27 | B | A | B | B | B | B | Inv. |
| 28 | A | A | A | A | A | A | Inv. |
| 29 | B | A | B | A | B | B | Inv. |

TABLE 11-continued

| | 10° C., 20% RH | | 25° C., 50% RH | | 30° C., 80% RH | | |
|---|---|---|---|---|---|---|---|
| Sample No. | Text quality | Color mixing (Bleeding) | Text quality | Color mixing (Bleeding) | Text quality | Text quality | Remarks |
| 30 | A | A | A | A | B | A | Inv. |
| 31 | B | B | B | B | B | B | Inv. |
| 32 | A | A | A | A | A | A | Inv. |

As is apparent from Table 11, it was proven that an image forming method comprising the compositions of the present invention, enable recording of a high definition image which was superior in text quality and exhibited no color mixing (being bleeding) on any kind of a recording material under various printing conditions.

Example 2

Preparation of Active Ray Curable Ink-Jet Ink Composition

Active Ray Curable Ink-jet Ink Composition 101 comprised of the following compositions was prepared.

| | |
|---|---|
| Triarylsulfonium salt compound: TAS-1 | 5 weight parts |
| Epoxy compound: EP-17 | 95 weight parts |

Active Ray Curable Ink-jet Ink Compositions 102-126 were prepared, as was Ink 101 except that the above triarylsulfonium salt compound and epoxy compound were replaced by the compounds described in Table 12. The details of the compounds in Table 12 were shown below.

UVI 6990: triphenylsulfonium salt (being CYRACURE UVI 6990, produced by Union Carbide Corp.)

CELLOXIDE 3000: alicyclic epoxy (produced by DAI CEL UCB.)

CELLOXIDE 2021P: alicyclic epoxy (produced by DAI CEL UCB.)

1 ml of the respective Active Ray Curable Ink-jet Ink Compositions was coated onto 157 $cm^2$ PET film, after which the PET film was sealed in a 6.1 l transparent airtight container, and UV radiation was conducted at 10 $mJ/cm^2$ of radiation energy over 20 sec. using a high-pressure mercury lamp, maintaining 30° C. by heating.

After that, gases in the airtight container were collected, and quantitative determination of benzene was conducted using gas chromatography. Identification of benzene was conducted using GS-MS, and quantitative determination of said benzene was conducted using a calibration curve prepared by analysis of a given quantity of benzene using gas chromatography. The detected quantity of benzene was indicated by generated weight (μg) per $m^2$ of the contents in the airtight container. The results are shown in Table 12.

Further, the viscosity changes of the obtained ray curable compositions is also shown. Viscosity change was determined by manually by touch of an experimenter before and after UV radiation with a metal spatula. "Gelation" in Table 12 means that a gelled film was formed, "thickening" means that viscosity after radiation was higher than before radiation, "slight thickening" means that viscosity after radiation was slightly higher than that of before radiation, and "no thickening" means that no significant differences of film viscosity before and after radiation.

TABLE 12

| Active ray curable composition No. | Triarylsulfonium salt compound | Epoxy compound | Benzene generated weight (μg/m²) | Viscosity change of curable composition | Remarks |
|---|---|---|---|---|---|
| 101 | TAS-1 | EP-17 | Not detected | Gelation | Inv. |
| 102 | TAS-4 | EP-17 | Not detected | Gelation | Inv. |
| 103 | TAS-5 | EP-17 | Not detected | Gelation | Inv. |
| 104 | TAS-6 | EP-17 | Not detected | Gelation | Inv. |
| 105 | TAS-10 | EP-17 | Not detected | Gelation | Inv. |
| 106 | TAS-11 | EP-17 | Not detected | Gelation | Inv. |
| 107 | TAS-13 | EP-17 | Not detected | Gelation | Inv. |
| 108 | TAS-15 | EP-14 | Not detected | Gelation | Inv. |
| 109 | TAS-17 | EP-14 | Not detected | Gelation | Inv. |
| 110 | TAS-18 | EP-14 | Not detected | Gelation | Inv. |
| 111 | TAS-26 | EP-14 | Not detected | Gelation | Inv. |
| 112 | TAS-39 | EP-14 | Not detected | Gelation | Inv. |
| 113 | TAS-40 | EP-14 | Not detected | Gelation | Inv. |
| 114 | TAS-47 | EP-14 | Not detected | Gelation | Inv. |
| 115 | TAS-54 | EP-14 | Not detected | Gelation | Inv. |
| 116 | TAS-1 | CELLOXIDE 3000 | Not detected | Gelation | Inv. |
| 117 | TAS-11 | CELLOXIDE 3000 | Not detected | Gelation | Inv. |
| 118 | TAS-13 | CELLOXIDE 2021P | Not detected | Gelation | Inv. |
| 119 | TAS-18 | CELLOXIDE 2021P | Not detected | Gelation | Inv. |
| 120 | UVI-6990 | EP-17 | 61 | Thickening | Comp. |
| 121 | UVI-6990 | CELLOXIDE 3000 | 72 | Thickening | Comp. |
| 122 | UVI-6990 | CELLOXIDE 2021P | 71 | Thickening | Comp. |

TABLE 12-continued

| Active ray curable composition No. | Triarylsulfonium salt compound | Epoxy compound | Benzene generated weight (μg/m²) | Viscosity change of curable composition | Remarks |
|---|---|---|---|---|---|
| 123 | UVI-6990 | EP-14 | 64 | Thickening | Comp. |
| 124 | None | None | Not detected | No thickening | Comp. |
| 125 | None | CELLOXIDE 3000 | Not detected | No thickening | Comp. |
| 126 | UVI-6990 | None | 67 | Slight thickening | Comp. |

Comp.; Comparative example
Inv.; This invention

As is apparent from Table 12, it was proven that the active ray curable ink-jet ink compositions comprising the triarylsulfonium salt and the epoxy compound of the present invention exhibited gelation and advance of polymerization without generation of benzene, when irradiated by ultraviolet rays.

Example 3

Preparation of Ink for Ink-jet

Preparation of Ink 201

Ink 201 comprising the following compositions was prepared. The following compositions, except for the photo-induced acid generating agent, were dispersed for four hours using a sand grinder, after which the photo-induced acid generating agent was added, the resulting mixture was filtered using a 0.8 μm membrane, and dehydration under reduced pressure was conducted at 50° C. under heat to prepare Ink 201.

| | |
|---|---|
| C.I. Pigment Red 184 | 3 weight parts |
| UVI 6990 | 5 weight parts |
| Aronoxetane OXT-221 | 70 weight parts |
| CELLOXIDE 3000 | 30 weight parts |
| Solsperse 24000 (produced by Avecia Limited) | 1 weight part |

Preparation of Inks 202-238

Ink 202-238 were prepared in the same manner as Ink 201, except that the pigment, photo-induced acid generating agent, epoxy compound and the oxetane compound were changed to the compositions described in following Table 13.

TABLE 13

| | Pigment | | Photo-induced acid generating agent | | Epoxy compound | | Oxetane compound | |
|---|---|---|---|---|---|---|---|---|
| Ink No. | Kind | Added amount (weight part) | Kind | Added amount (weight part) | Kind | Added amount (weight part) | Kind | Added amount (weight part) |
| 201 | P1 | 3 | UVI6990 | 4 | CELLOXIDE 3000 | 30 | OXT221 | 70 |
| 202 | P1 | 3 | UVI6990 | 4 | CELLOXIDE 3000 | 20 | OXT221 | 80 |
| 203 | P0 | 3 | UVI6990 | 4 | CELLOXIDE 2021P | 30 | OXT221 | 70 |
| 204 | P0 | 3 | UVI6990 | 4 | CELLOXIDE 2021P | 20 | OXT221 | 80 |
| 205 | P2 | 3 | PI-1 | 4 | CELLOXIDE 2021P | 30 | OXT221 | 70 |
| 206 | P2 | 3 | PI-1 | 4 | CELLOXIDE 2021P | 20 | OXT221 | 80 |
| 207 | P0 | 3 | PI-2 | 4 | CELLOXIDE 2021P | 30 | OXT221 | 70 |
| 208 | P0 | 3 | PI-2 | 4 | CELLOXIDE 2021P | 20 | OXT221 | 80 |
| 209 | P1 | 3 | TAS-1 | 4 | CELLOXIDE 3000 | 30 | OXT221 | 70 |
| 210 | P1 | 3 | TAS-1 | 4 | CELLOXIDE 3000 | 20 | OXT221 | 80 |
| 211 | P1 | 3 | TAS-4 | 4 | CELLOXIDE 2021P | 30 | OXT221 | 70 |
| 212 | P1 | 4 | TAS-4 | 4 | CELLOXIDE 2021P | 20 | OXT221 | 80 |
| 213 | P0 | 4 | TAS-6 | 4 | EP-14 | 30 | OXT221 | 70 |
| 214 | P0 | 4 | TAS-6 | 4 | EP-14 | 20 | OXT221 | 80 |
| 215 | P2 | 4 | TAS-10 | 4 | EP-17 | 30 | OXT221 | 70 |
| 216 | P2 | 4 | TAS-10 | 4 | EP-17 | 20 | OXT221 | 80 |
| 217 | P1 | 4 | TAS-11 | 4 | EP-17 | 30 | OXT221 | 70 |
| 218 | P1 | 4 | TAS-11 | 4 | EP-17 | 20 | OXT221 | 80 |
| 219 | P2 | 4 | TAS-13 | 4 | EP-14 | 30 | OXT221 | 70 |
| 220 | P2 | 4 | TAS-13 | 4 | EP-14 | 20 | OXT221 | 80 |
| 221 | P1 | 4 | TAS-15 | 4 | EP-14 | 30 | OXT221 | 70 |
| 222 | P1 | 4 | TAS-15 | 4 | EP-14 | 20 | OXT221 | 80 |
| 223 | P2 | 4 | TAS-18 | 4 | EP-17 | 30 | OXT221 | 70 |
| 224 | P2 | 4 | TAS-18 | 4 | EP-17 | 20 | OXT221 | 80 |
| 225 | P0 | 4 | TAS-26 | 4 | EP-17 | 30 | OXT221 | 70 |
| 226 | P0 | 4 | TAS-26 | 4 | EP-17 | 20 | OXT221 | 80 |
| 227 | P1 | 4 | TAS-39 | 4 | EP-14 | 30 | OXT221 | 70 |
| 228 | P1 | 4 | TAS-39 | 4 | EP-14 | 20 | OXT221 | 80 |
| 229 | P1 | 4 | TAS-40 | 4 | EP-14 | 30 | OXT221 | 70 |

TABLE 13-continued

| Ink No. | Pigment Kind | Pigment Added amount (weight part) | Photo-induced acid generating agent Kind | Photo-induced acid generating agent Added amount (weight part) | Epoxy compound Kind | Epoxy compound Added amount (weight part) | Oxetane compound Kind | Oxetane compound Added amount (weight part) |
|---|---|---|---|---|---|---|---|---|
| 230 | P1 | 4 | TAS-40 | 4 | EP-14 | 20 | OXT221 | 80 |
| 231 | P2 | 4 | TAS-47 | 4 | EP-14 | 30 | OXT221 | 70 |
| 232 | P2 | 4 | TAS-47 | 4 | EP-14 | 20 | OXT221 | 80 |
| 233 | P1 | 4 | TAS-54 | 4 | EP-17 | 30 | OXT221 | 70 |
| 234 | P1 | 4 | TAS-54 | 4 | EP-17 | 20 | OXT221 | 80 |
| 235 | P0 | 4 | TAS-1 | 4 | EP-17 | 30 | OXT221 | 70 |
| 236 | P0 | 4 | TAS-1 | 4 | EP-17 | 20 | OXT221 | 80 |
| 237 | P0 | 4 | TAS-4 | 4 | EP-17 | 30 | OXT221 | 70 |
| 238 | P0 | 4 | TAS-4 | 4 | EP-17 | 20 | OXT221 | 80 |

The details of compounds described in Table 13 are shown below.

Pigment

P0: C. I. Pigment Red 184

P1: crude copper phthalocyanine

Placed into a 4.55 l (1 U.K. Gallon) stainless steel kneader (manufactured by INOUE MFG., INC.) were 250 parts of copper phthalocyanine (produced by TOYO INK MFG. CO., LTD.), 2,500 parts of sodium chloride, and 160 parts of polyethylene glycol (being "polyethylene glycol 300", produced by Tokyo Kasei Kogyo Co., Ltd.), and kneaded for three hours. After which, the mixture was poured into 2.5 l of warm water, and stirred to form a slurry for about one hour using a high speed mixer, while heated to about 80° C., after which filtration and washing was repeated five times to remove sodium chloride and the solvents. Subsequently, spray drying was conducted to obtain pigment P1.

P2: quinacridone type red pigment

Placed into a 4.55 l (1 U.K. Gallon) stainless steel kneader were 250 parts of "CINQUASIA Magenta RT-355-D" (produced by Ciba Geigy Limited), 2,500 parts of sodium chloride, and 160 parts of "polyethylene glycol 300", after which P2 was obtained similarly to P1.

Epoxy Compound

CELLOXIDE 3000: alicyclic epoxy (produced by DAI CEL UCB.)

CELLOXIDE 2021P: alicyclic epoxy (produced by DAI CEL UCB.)

Photo-induced Acid Generating Agent

UVI 6990: triphenylsulfonium salt (being CYRACURE UVI 6990, produced by Union Carbide Corp.)

PI-1: triphenylsulfonium salt (being a compound described in German Patent No. 2061280, pg. 2.)

PI-2: triphenylsulfonium salt (being a compound described in U.S. Pat. No. 2,061,280, Table III.)

Oxetane Compound

OXT-221: di[1-ethyl(3-oxetanyl)]methyl ether (produced by TOAGOSEI CO., LTD.)

Ink-jet Image Recording and Evaluation

Using each of the inks prepared above, image recording and evaluation of resulting images were conducted based on the following methods.

Image Evaluation A

Image Recording

Each of the obtained inks was ejected onto a base material of a corona treated polyethylene terephthalate film, while the nozzle portion was heated to 50° C., using piezo type ink-jet nozzles capable of ejecting droplets of 7 pl, nozzle pitch being 360 dpi, (hereby, "dpi" in this invention indicated a number of dots per inch or per 2.54 cm), to print a solid magenta image and 6 point, MS Ming-style characters. The light source was a fluorescent tube peaking at 308 nm, and exposure was initiated at 0.3 sec. after ink deposition and completed 0.8 sec. after ink deposition, under the conditions of illuminance of 10 mW/cm$^2$ on the surface of the base material being directly below the light source, at an exposure energy of 5 mJ/cm$^2$. Image printing was conducted under low humidity condition (being 25° C. and 20% RH) and high humidity condition (being 25° C. and 85% RH).

Evaluation of Images

Each of the images obtained as above was evaluated for the following characteristics.

Evaluation of Curability

Printed images formed under each set of conditions were evaluated for ink curability based on the following criteria.

A: Immediately after exposure, images exhibited no tackiness.

B: Immediately after exposure, images exhibited slight tackiness, but after one minute, no tackiness.

C: One min. after exposure, images still exhibited some tackiness.

Evaluation of Adhesiveness onto Base Material

Onto the solid images formed under each set of printing conditions, 25 mm wide Sellotape® was adhered via strong pressure, after which the tape was ripped off quickly at a peeling angle of 90 degree, and then the status of the images after peeling was visually observed to evaluate adhesiveness onto the base material, with the following results.

A: No image peeling was observed.

B: Slight image peeling was observed.

C: All the image was peeled off.

Evaluation of Bleeding Resistance 6 point, MS Ming-style characters formed under each set of printing conditions were observed using a loupe on the status of adjacent dots, to evaluate bleeding resistance based on the following criteria.

A: Bleeding between adjacent dots was rarely observed.
B: Slight bleeding between adjacent dots was observed.
C: Obvious bleeding was observed.

Results of the above evaluation are shown in Tables 14 and 15.

TABLE 14

| Ink No. | Printing condition (% RH) | Ink curability | Adhesiveness onto base material | Image bleeding resistance | Remarks |
|---|---|---|---|---|---|
| 201 | 20 | A | A | A | Comp. |
| 201 | 80 | A | A | B | Comp. |
| 202 | 20 | A | A | A | Comp. |
| 202 | 80 | B | B | B | Comp. |
| 203 | 20 | A | A | A | Comp. |
| 203 | 80 | B | A | B | Comp. |
| 204 | 20 | A | A | A | Comp. |
| 204 | 80 | B | B | B | Comp. |
| 205 | 20 | A | A | A | Comp. |
| 205 | 80 | B | A | A | Comp. |
| 206 | 20 | A | A | A | Comp. |
| 206 | 80 | B | A | A | Comp. |
| 207 | 20 | A | A | A | Comp. |
| 207 | 80 | B | A | A | Comp. |
| 208 | 20 | A | A | A | Comp. |
| 208 | 80 | B | A | A | Comp. |
| 209 | 20 | A | A | A | Inv. |
| 209 | 80 | A | A | A | Inv. |
| 210 | 20 | A | A | A | Inv. |
| 210 | 80 | A | A | A | Inv. |
| 211 | 20 | A | A | A | Inv. |
| 211 | 80 | A | A | A | Inv. |
| 212 | 20 | A | A | A | Inv. |
| 212 | 80 | A | A | A | Inv. |
| 213 | 20 | A | A | A | Inv. |
| 213 | 80 | A | A | A | Inv. |
| 214 | 20 | A | A | A | Inv. |
| 214 | 80 | A | A | A | Inv. |
| 215 | 20 | A | A | A | Inv. |
| 215 | 80 | A | A | A | Inv. |
| 216 | 20 | A | A | A | Inv. |
| 216 | 80 | A | A | A | Inv. |
| 217 | 20 | A | A | A | Inv. |
| 217 | 80 | A | A | A | Inv. |
| 218 | 20 | A | A | A | Inv. |
| 218 | 80 | A | A | A | Inv. |
| 219 | 20 | A | A | A | Inv. |
| 219 | 80 | A | A | A | Inv. |

TABLE 15

| Ink No. | Printing condition (% RH) | Ink curability | Adhesiveness onto base material | Image bleeding resistance | Remarks |
|---|---|---|---|---|---|
| 220 | 20 | A | A | A | Inv. |
| 220 | 80 | A | A | A | Inv. |
| 221 | 20 | A | A | A | Inv. |
| 221 | 80 | A | A | A | Inv. |
| 222 | 20 | A | A | A | Inv. |
| 222 | 80 | A | A | A | Inv. |
| 223 | 20 | A | A | A | Inv. |
| 223 | 80 | A | A | A | Inv. |
| 224 | 20 | A | A | A | Inv. |
| 224 | 80 | A | A | A | Inv. |
| 225 | 20 | A | A | A | Inv. |
| 225 | 80 | A | A | A | Inv. |
| 226 | 20 | A | A | A | Inv. |
| 226 | 80 | A | A | A | Inv. |
| 227 | 20 | A | A | A | Inv. |
| 227 | 80 | A | A | A | Inv. |
| 228 | 20 | A | A | A | Inv. |
| 228 | 80 | A | A | A | Inv. |
| 229 | 20 | A | A | A | Inv. |
| 229 | 80 | A | A | A | Inv. |
| 230 | 20 | A | A | A | Inv. |
| 230 | 80 | A | A | A | Inv. |
| 231 | 20 | A | A | A | Inv. |
| 231 | 80 | A | A | A | Inv. |
| 232 | 20 | A | A | A | Inv. |
| 232 | 80 | A | A | A | Inv. |
| 233 | 20 | A | A | A | Inv. |
| 233 | 80 | A | A | A | Inv. |
| 234 | 20 | A | A | A | Inv. |
| 234 | 80 | A | A | A | Inv. |
| 235 | 20 | A | A | A | Inv. |
| 235 | 80 | A | A | A | Inv. |
| 236 | 20 | A | A | A | Inv. |
| 236 | 80 | A | A | A | Inv. |
| 237 | 20 | A | A | A | Inv. |
| 237 | 80 | A | A | A | Inv. |
| 238 | 20 | A | A | A | Inv. |
| 238 | 80 | A | A | A | Inv. |

Image Evaluation B

In Image Evaluation A above, image recording and evaluation were conducted similarly, except that radiation initiation after printing using evaluated inks was changed to 0.4 sec., and radiation duration was changed to 0.9 sec. Exposure time and exposure energy were the same as those of Image Evaluation A, being 0.5 sec. and 5 mJ/cm2. The obtained results are shown in Tables 16 and 17.

TABLE 16

| Ink No. | Printing condition (% RH) | Ink curability | Adhesiveness onto base material | Image bleeding resistance | Remarks |
|---|---|---|---|---|---|
| 201 | 20 | B | B | B | Comp. |
| 201 | 80 | B | B | C | Comp. |
| 202 | 20 | B | B | B | Comp. |
| 202 | 80 | B | B | C | Comp. |
| 203 | 20 | B | B | B | Comp. |
| 203 | 80 | B | B | C | Comp. |
| 204 | 20 | B | B | B | Comp. |
| 204 | 80 | C | C | C | Comp. |
| 205 | 20 | B | B | B | Comp. |
| 205 | 80 | C | B | C | Comp. |
| 206 | 20 | B | B | B | Comp. |
| 206 | 80 | C | B | C | Comp. |
| 207 | 20 | B | B | B | Comp. |
| 207 | 80 | C | B | C | Comp. |
| 208 | 20 | B | B | B | Comp. |
| 208 | 80 | C | C | C | Comp. |
| 209 | 20 | A | A | A | Inv. |
| 209 | 80 | B | A | B | Inv. |
| 210 | 20 | A | A | A | Inv. |
| 210 | 80 | A | B | B | Inv. |
| 211 | 20 | A | A | A | Inv. |
| 211 | 80 | A | B | A | Inv. |
| 212 | 20 | A | A | A | Inv. |
| 212 | 80 | A | A | B | Inv. |
| 213 | 20 | A | A | A | Inv. |
| 213 | 80 | A | A | A | Inv. |
| 214 | 20 | A | A | A | Inv. |
| 214 | 80 | A | A | A | Inv. |
| 215 | 20 | A | A | A | Inv. |
| 215 | 80 | A | A | A | Inv. |

TABLE 16-continued

| Ink No. | Printing condition (% RH) | Ink curability | Adhesiveness onto base material | Image bleeding resistance | Remarks |
|---|---|---|---|---|---|
| 216 | 20 | A | A | A | Inv. |
| 216 | 80 | A | A | A | Inv. |
| 217 | 20 | A | A | A | Inv. |
| 217 | 80 | A | A | A | Inv. |
| 218 | 20 | A | A | A | Inv. |
| 218 | 80 | A | A | A | Inv. |
| 219 | 20 | A | A | A | Inv. |
| 219 | 80 | A | A | A | Inv. |

TABLE 17

| Ink No. | Printing condition (% RH) | Ink curability | Adhesiveness onto base material | Image bleeding resistance | Remarks |
|---|---|---|---|---|---|
| 220 | 20 | A | A | A | Inv. |
| 220 | 80 | A | A | A | Inv. |
| 221 | 20 | A | A | A | Inv. |
| 221 | 80 | A | A | A | Inv. |
| 222 | 20 | A | A | A | Inv. |
| 222 | 80 | A | A | A | Inv. |
| 223 | 20 | A | A | A | Inv. |
| 223 | 80 | A | A | A | Inv. |
| 224 | 20 | A | A | A | Inv. |
| 224 | 80 | A | A | A | Inv. |
| 225 | 20 | A | A | B | Inv. |
| 225 | 80 | B | A | B | Inv. |
| 226 | 20 | A | A | A | Inv. |
| 226 | 80 | A | A | A | Inv. |
| 227 | 20 | A | A | A | Inv. |
| 227 | 80 | A | B | A | Inv. |
| 228 | 20 | A | A | A | Inv. |
| 228 | 80 | A | B | A | Inv. |
| 229 | 20 | A | A | A | Inv. |
| 229 | 80 | A | B | A | Inv. |
| 230 | 20 | A | A | A | Inv. |
| 230 | 80 | A | A | B | Inv. |
| 231 | 20 | A | A | A | Inv. |
| 231 | 80 | A | A | B | Inv. |
| 232 | 20 | A | A | A | Inv. |
| 232 | 80 | A | A | B | Inv. |
| 233 | 20 | A | A | A | Inv. |
| 233 | 80 | A | B | A | Inv. |
| 234 | 20 | A | A | A | Inv. |
| 234 | 80 | A | B | A | Inv. |
| 235 | 20 | A | A | A | Inv. |
| 235 | 80 | A | A | A | Inv. |
| 236 | 20 | A | A | A | Inv. |
| 236 | 80 | A | A | A | Inv. |
| 237 | 20 | A | A | A | Inv. |
| 237 | 80 | A | A | A | Inv. |
| 238 | 20 | A | A | A | Inv. |
| 238 | 80 | A | A | A | Inv. |

As is apparent from Table 11, it was proven that an image forming method comprising the compositions of the present invention, enabled recording of high definition images which were superior in text quality and exhibited no color mixing (being no bleeding) on any kind of recording material under various printing conditions.

What is claimed is:

1. A triarylsulfonium salt compound represented by Formula (T-3):

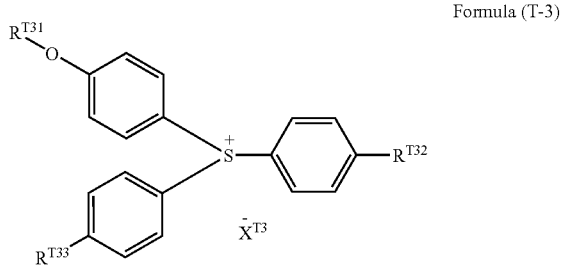

Formula (T-3)

wherein $R^{T31}$ is methyl or ethyl; $R^{T32}$ and $R^{T33}$ are each methyl or ethyl; and $X^{T3}$ is $PF_6$.

2. A triarylsulfonium salt compound represented by Formula (T-4):

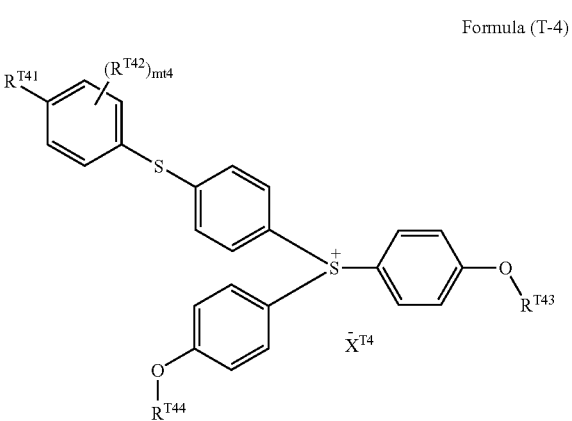

Formula (T-4)

wherein $R^{T41}$ is methyl or ethyl, $R^{T42}$ is a straight-chained branched or cyclic alkyl group or an aromatic hydrocarbon ring or an aromatic heterocyclic ring or condensed ring aromatic group, mt4 is an integer of 0-4, $R^{T43}$ and $R^{T44}$ are each methyl or ethyl, and $X^{T4}$ is $PF_6$.

3. A triarylsulfonium salt compound represented by Formula (T-5):

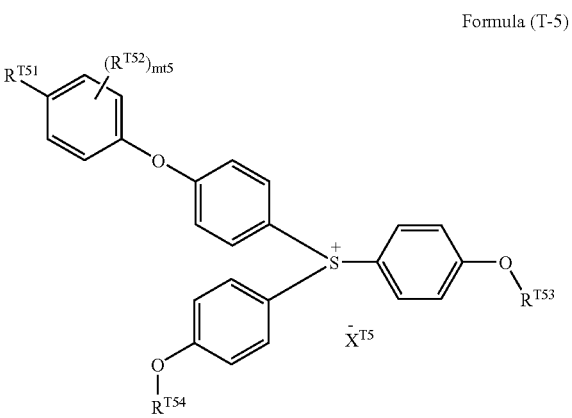

Formula (T-5)

wherein $R^{T51}$ is methyl or ethyl, $R^{T52}$ is a straight-chained, branched or cyclic alkyl group, or an aromatic hydrocarbon ring or an aromatic heterocyclic ring or condensed ring aromatic group, mt5 is an integer of 0-4, $R^{T53}$ and $R^{T54}$ are each an alkyl group of 1-10 carbon atoms with the proviso that at least one of $R^{T53}$ and $R^{T54}$ is methyl, and $X^{T5}$ is $PF_6$.

4. An active ray curable composition comprising:
 (a) a triarylsulfonium compound described in claim 1, 2 or 3; and
 (b) an epoxy compound.

5. The active ray curable composition according to claim 4, wherein the epoxy compound is an alicyclic epoxy compound represented by Formula (A):

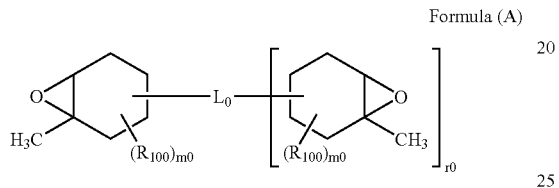

Formula (A)

wherein $R_{100}$ is a substituent group; m0 is an integer of 0-2; r0 is an integer of 1-3; $L_0$ is a r0+1 valent linking group of 1-15 carbon atoms, which may contain an oxygen atom or a sulfur atom in the principal chain, or a single bond.

6. The active ray curable composition according to claim 4, wherein the epoxy compound is one selected from the alicyclic compounds represented by one of the following Formulas;

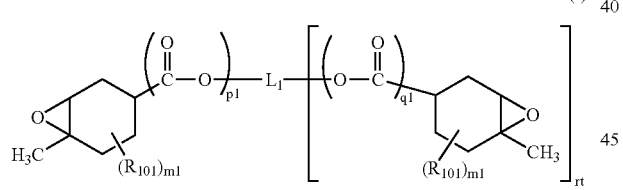

Formula (I)

wherein $R_{101}$ is a substituent group, m1 is an integer of 0-2, p1 and q1 are each 0 or 1, r1 is an integer of 1-3, and $L_1$ is a r1+1 valent linking group of 1-15 carbon atoms, which may contain an oxygen atom or a sulfur atom in the principal chain, or a single bond;

wherein, p2 and q2 are each 0 or 1, $L_2$ is a r2+1 valent linking group of 1-15 carbon atoms, which may contain an oxygen atom or a sulfur atom in the principal chain, or a single bond;

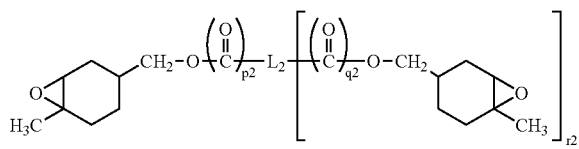

Formula (III)

wherein $R_{103}$ is a substituent group, m3 is an integer of 0-2, p3 is 0 or 1, L3 is a divalent linking group of 1-8 carbon atoms, which may contain an oxygen atom or a sulfur atom in the principal chain, or a single bond;

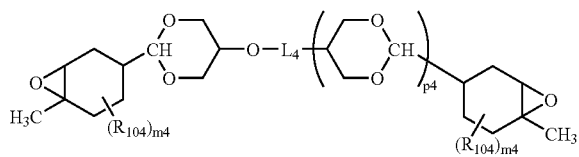

Formula (IV)

wherein $R_{104}$ is a substituent group, m4 is an integer of 0-2, p4 is 0 or 1, L4 is a divalent linking group of 1-8 carbon atoms, which may contain an oxygen atom or a sulfur atom in the principal chain, or a single bond;

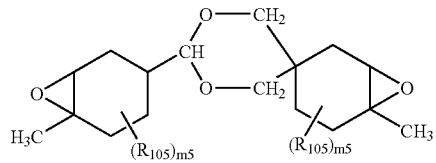

Formula (V)

wherein $R_{105}$ is a substituent group, and m5 is 1 or 2; and

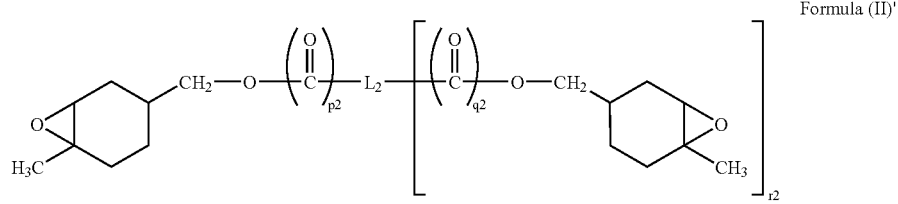

Formula (II)'

Formula (VI)

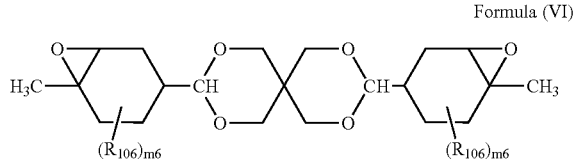

wherein $R_{106}$ is a substituent group, and m6 is an integer of 0-2.

7. An active ray curable ink-jet ink composition containing the active ray curable composition according to claim 4.

8. The ink-jet composition of claim 7 wherein the epoxy compound is an alicyclic epoxy compound represented by Formula (A):

Formula (A)

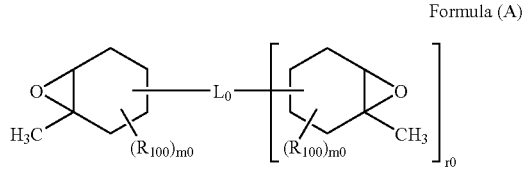

wherein $R_{100}$ is a substituent group; m0 is an integer of 0-2; r0 is an integer of 1-3; $L_0$ is a r0+1 valent linking group of 1-15 carbon atoms, which may contain an oxygen atom or a sulfur atom in the principal chain, or a single bond.

9. The active ray curable composition according to claim 4, wherein the epoxy compound is one selected from the alicyclic compounds represented by one of the following Formulas:

Formula (I)

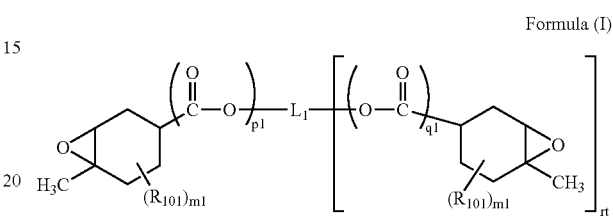

wherein $R_{101}$ is a substituent group, m1 is an integer of 0-2, p1 and q1 are each 0 or 1, r1 is an integer of 1-3, and $L_1$ is a r1+1 valent linking group of 1-15 carbon atoms, which may contain an oxygen atom or a sulfur atom in the principal chain, or a single bond;

Formula (II)'

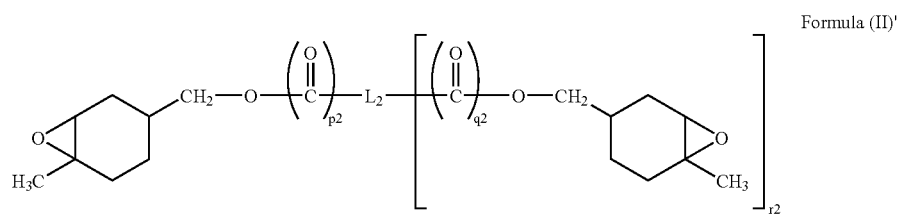

wherein p2 and q2 are each 0 or 1, $L_2$ is a r2+1 valent linking group of 1-15 carbon atoms, which may contain an oxygen atom or a sulfur atom in the principal chain, or a single bond;

Formula (III)

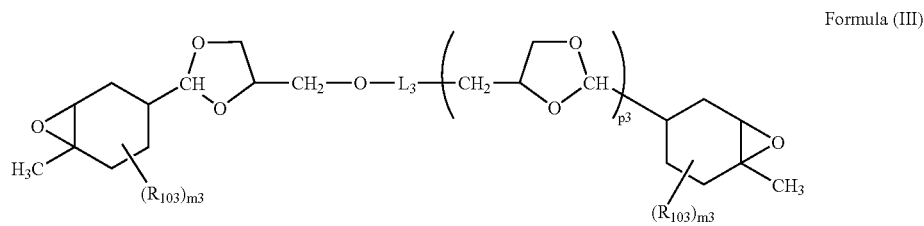

wherein $R_{103}$ is a substituent group, m3 is an integer of 0-2, p3 is 0 or 1, $L_3$ is a divalent linking group of 1-8 carbon atoms, which may contain an oxygen atom or a sulfur atom in the principal chain, or a single bond;

Formula (IV)

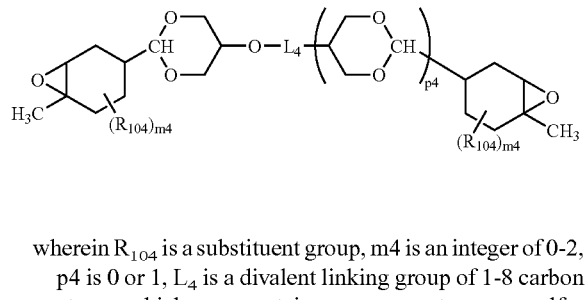

wherein $R_{104}$ is a substituent group, m4 is an integer of 0-2, p4 is 0 or 1, $L_4$ is a divalent linking group of 1-8 carbon atoms, which may contain an oxygen atom or a sulfur atom in the principal chain, or a single bond;

Formula (V)

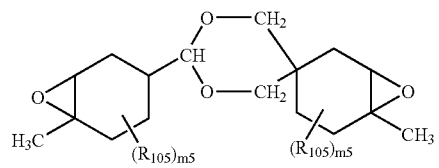

wherein $R_{105}$ is a substituent group, and m5 is 1 or 2; and

Formula (VI)

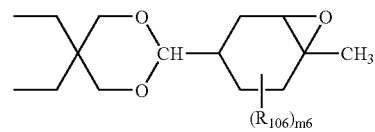

wherein $R_{106}$ is a substituent group, and m6 is an integer of 0-2.

* * * * *